United States Patent
Young et al.

(10) Patent No.: US 12,054,733 B2
(45) Date of Patent: Aug. 6, 2024

(54) UNIVERSAL SELF-REGULATING MAMMALIAN CELL LINE PLATFORM FOR THE PRODUCTION OF BIOLOGICS

(71) Applicant: LONZA LTD, Visp (CH)

(72) Inventors: Robert Young, Visp (CH); Peter Michael O'Callaghan, Visp (CH); Thomas Payne, Visp (CH)

(73) Assignee: LONZA LTD, Visp (CH)

( * ) Notice: Subject to any disclaimer, the term of this patent is extended or adjusted under 35 U.S.C. 154(b) by 956 days.

(21) Appl. No.: 16/622,509

(22) PCT Filed: Jun. 15, 2018

(86) PCT No.: PCT/US2018/037792
§ 371 (c)(1),
(2) Date: Dec. 13, 2019

(87) PCT Pub. No.: WO2018/232265
PCT Pub. Date: Dec. 20, 2018

(65) Prior Publication Data
US 2020/0208171 A1    Jul. 2, 2020

Related U.S. Application Data

(60) Provisional application No. 62/521,005, filed on Jun. 16, 2017.

(51) Int. Cl.
*C12N 15/85* (2006.01)
*C12N 9/22* (2006.01)
*C12N 15/11* (2006.01)
*A61K 39/00* (2006.01)

(52) U.S. Cl.
CPC .............. *C12N 15/85* (2013.01); *C12N 9/22* (2013.01); *C12N 15/11* (2013.01); *A61K 39/00* (2013.01); *C12N 2800/80* (2013.01)

(58) Field of Classification Search
CPC ........... C12N 9/22; C12N 15/11; A61K 39/00
See application file for complete search history.

(56) References Cited

U.S. PATENT DOCUMENTS

| | | |
|---|---|---|
| 5,656,491 A | 8/1997 | Cassani et al. |
| 6,326,193 B1 | 12/2001 | Liu et al. |
| 6,703,199 B1 | 3/2004 | Koide et al. |
| 7,629,167 B2 | 12/2009 | Hodge et al. |
| 8,298,054 B2 | 10/2012 | Hodge et al. |
| 2009/0305626 A1 | 12/2009 | Hope et al. |
| 2011/0280797 A1 | 11/2011 | Mohtadi et al. |
| 2012/0077429 A1 | 3/2012 | Wernimont et al. |
| 2013/0280797 A1 | 10/2013 | Rao et al. |
| 2016/0097074 A1 | 4/2016 | Collins et al. |

FOREIGN PATENT DOCUMENTS

| | | |
|---|---|---|
| WO | 2001/029058 A1 | 4/2001 |
| WO | 2001/096584 A2 | 12/2001 |
| WO | 2004/009823 A1 | 1/2004 |
| WO | 2006/111387 A2 | 10/2006 |
| WO | 2014/044845 A1 | 3/2014 |
| WO | 2015/157070 A2 | 10/2015 |
| WO | 2017/064566 A2 | 4/2017 |
| WO | 2017075294 A1 | 5/2017 |

OTHER PUBLICATIONS

Thakore et al., "Highly Specific Epigenome Editing by CRISPR/Cas9 Repressors for Silencing of Distal Regulatory Elements", Nature Methods, 2015, 12(12): 1143-1149. doi:10.1038/nmeth.3630.*
Young et al (Advances in stem cells, induced pluripotent stem cells, and engineered cells: delivery vehicles for anti-glioma therapy. Expert Opin Drug Deliv., vol. 11, Jul. 2014) (Year: 2014).*
Adamson et al (A Multiplexed Single-Cell CRISPR Screening Platform Enables Systematic Dissection of the Unfolded Protein Response. Cell, vol. 167, Dec. 2016) (Year: 2016).*
CRISPick (sgRNA design tool from Broad Institute). (Year: 2023).*
Gazit et al (Use of the Stress-inducible grp78/BiP Promoter in Targeting High Level Gene Expression in Fibrosarcoma in Vivo. Cancer Research, vol. 55, Apr. 1995). (Year: 1995).*
Jinek et al (A Programmable Dual-RNA-Guided DNA Endonuclease in Adaptive Bacterial Immunity. Science, vol. 337, 2012) (Year: 2012).*
Mandegar et al (CRISPR Interference Efficiently Induces Specific and Reversible Gene Silencing in Human iPSCs. Cell Stem Cell, vol. 18, Apr. 2016) (Year: 2016).*
Sundaresan et al (RNA-Independent DNA Cleavage Activities of Cas9 and Cas12a. Cell Rep, vol. 21, Dec. 2017) (Year: 2017).*
Adamson et al., A multiplexed single-cell CRISPR screening platform enables systematic dissection of the unfolded protein response, Cell, 2016, 167(7):1867-1882.
Sheng et al., Systematic optimization of protein secretory pathways in Saccharomyces cerevisiae to increase expression of Hepatitis B small antigen, 2017, Frontiers in Microbiology, 8:article 875.
Anders et al., "Structural Basis of PAM-dependent Target DNA Recognition by the Cas9 Endonuclease," Nature, 513(7519): 569-573 (2014).
Bae et al., "Cas-OFFinder: A Fast and Versatile Algorithm That Searches for Potential Off-Target Sites of Cas9 RNA-guided Endonucleases," Bioinformatics, 30(10): 1473-1475 (2014).

(Continued)

*Primary Examiner* — Valarie E Bertoglio
*Assistant Examiner* — Matasha Dhar
(74) *Attorney, Agent, or Firm* — MEDLER FERRO WOODHOUSE & MILLS PLLC

(57) ABSTRACT

Disclosed are genetic control circuits, cells, and methods that use a repressor polypeptide to reduce the transcription rate of an exogenous therapeutic polypeptide encoding gene in response to a change in condition.

12 Claims, 9 Drawing Sheets

Specification includes a Sequence Listing.

(56) References Cited

OTHER PUBLICATIONS

Batzer et al., "Enhanced evolutionary PCR using oligonucleotides with inosine at the 3'-terminus," Nuc. Acids Res., 19(18): 6081.
Bisht et al., "A lentivirus-free inducible CRISPR-Cas9 system for efficient targeting of human genes," Analytical Biochemistry, 530: 40-49 (2017).
Borth et al., "Effect of Increased Expression of Protein Disulfide Isomerase and Heavy Chain Binding Protein on Antibody Secretion in a Recombinant CHO Cell Line," Biotechnol. Prog., 21(1): 106-111 (2005).
Brown et al., "Synthetic Promoters for CHO Cell Engineering," Biotechnology and Bioengineering (2014), 111(8): 1638-1647.
Bultmann et al., "Targeted Transcriptional Activation of Silent oct4 Pluripotency Gene by Combining Designer TALEs and Inhibition of Epigenetic Modifiers," Nucleic Acids Res. 40(12): 5368-5377 (2012).
Cain et al., "A Cho Cell Line Engineered to Express XBP1 and ERO1-Lalpha Has Increased Levels of Transient Protein Expression," Biotechnol. Prog., 29(3): 697-706 (2013).
Carvel et al., "On-line Measurements and Control of Viable Cell Density in Cell Culture Manufacturing Processes using Radio-frequency Impedance," Cytotechnology, 50: 35-48 (2006).
Cermak et al., "Efficient Design and Assembly of Custom TALEN and Other TAL Effector-based Constructs for DNA Targeting," Nucleic Acids Res., 39(12): e82 (2011).
Chakravarthi et al., "Glutathione is Required to Regulate the Formation of Native Disulfide Bonds within Proteins Entering the Secretory Pathway," J. Biol. Chem., 279(38): 39872-39879 (2004).
Chernajovsky et al., "Efficient Constitutive Production of Human Fibroblast Interferon by Hamster Cells Transformed with the IFN-beta 1 Gene Fused to an SV40 Early Promoter," DNA, 3(4): 297-308 (1984).
Chung et al., "Effect of doxycycline-regulated calnexin and calreticulin expression on specific thrombopoetin productivity of recombinant chinese hamster ovary cells," Biotechnol. and Bioeng., 85(5): 539-546 (2004).
Chylinski et al., "The tracrRNA and Cas9 Families of Type II CRISPR-Cas Immunity Systems," RNA Biology 10(5): 727-73 (2013).
Cong et al., "Comprehensive Interrogation of Natural TALE DNA-binding Modules and Transcriptional Repressor Domains," Nat Commun., 3(968), (2012).
Davis et al., "The Unfolded Protein Response Regulates Multiple Aspects of Secretory and Membrane Protein Biogenesis and Endoplasmic Reticulum Quality Control," J. Cell Biol., 2000.
Deer et al., "High-Level Expression of Proteins in Mammalian Cells Using Transcription Regulatory Sequences from the Chinese Hamster EF-1alpha Gene," Biotechnol. Progress, 20(3): 880-889 (2004).
Fan et al., "The use of glutamine synthetase as a selection marker: recent advances in Chinese hamster ovary cell line generation processes," Pharm. Bioprocess., 1(5): 487-502 (2013).
Fu et al., "Improving CRISPR-Cas Nuclease Specificity Using Truncated Guide RNAs," Nat Biotechnol., 32(3): 279-284 (2014).
Gao et al., "Self-processing of Ribozyme-Flanked RNAs to Guide RNAs in Vitro and in Vivo for CRISPR-mediated Genome Editing," J. Integr. Plant Biol., 56(4): 343-349 (2014).
Gaillet et al., "High-Level Recombinant Protein Production in CHO Cells Using an Adenoviral Vector and the Cumate Gene-Switch," Biotechnol. Prog., 23(1): 200-209 (2007).
Geissler et al., "Transcriptional Activators of Human Genes with Programmable DNA-Specificity," PLoS One, 6(5): e19509 (2011).
Genga et al., "Controlling transcription in human pluripotent stem cells using CRISPR-effectors," Methods, 101: 36-42 (2016).
Guo et al., "An Inducible CRISPR-ON System for Controllable Gene Activation in Human Pluripotent Stem Cells," Protein & Cell, 8(5): 379-393 (2017).
Garg et al., "Engineering synthetic TAL effectors with orthogonal target sites," Nucleic Acids Res., 40(15): 7584-7595 (2012).
Greisman, "A General Strategy for Selecting High-Affinity Zinc Finger Proteins for Diverse DNA Target Sites," Science, 275(5300): 657-661 (1997).
Holliger et al., "Engineered Antibody Fragments and the Rise of Single Domains," Nature Biotechnology, 23(9): 1126-1136 (2005).
Ham, "Clonal Growth of Mammalian Cells in a Chemically Defined, Synthetic Medium," PNAS, 53: 288-293 (1965).
Hou et al., "Efficient genome engineering in human pluripotent stem cells using Cas9 from Neisseria meningitidis," PNAS 110(39): 15644-15649 (2013).
Heigwer et al., "E-CRISP: fast CRISPR target site identification," Nature Methods, 11(2): 122-123 (2014).
Hsu et al., "DNA Targeting Specificity of RNA-guided Cas9 Nucleases," Nat. Biotechnol. 31(9): 827-832 (2013).
Indra et al., "Temporally-controlled site-specific mutagenesis in the basal layer of the epidermis: comparison of the recombinase activity of the tamoxifen-inducible Cre-ERT and Cre-ERT2 recombinases," Nucleic Acids Research, 27(22): 4324-4327 (1999).
Isalan, et al. "Synergy between adjacent zinc finger in sequence-specific DNA recognition," PNAS 94: 5617-5621 (1997).
Iscove et al., "Complete replacement of serum by albumin, transferrin, and soybean lipid in culture of lipopolysaccharide-reactive B lymphocytes," J. Exp. Med. 1, 147: 923-933 (1978).
Jinek et al., "A programmable dual RNA-guided DNA endonuclease in adaptive bacterial immunity," Science, 337(6096): 816-821 (2012).
Jinek et al., "Structures of Cas9 Endonucleases Reveal RNA-Mediated Conformational Activation," Science, 343(6176): 1247997-1247997 (2014).
Juillerat et al., "Optimized tuning of TALEN specificity using non-conventional RVDs," Sci Rep., 5(8150) (2015).
Krishna et al., "Structural classifications of zinc fingers: Survey and Summary," Nucl. Acids Res. 31(20): 532-550 (2003).
Ku et al., "Genomewide Analysis of PRC1 and PRC2 Occupancy Identifies Two Classes of Bivalent Domains," PLoS Genetics, 4(10): e1000242 (2008).
Leader et al., "Protein Therapeutics: A Summary and Pharmacological Classification," Nat. Rev. Drug Discovery, 7(1): 21-39 (2008).
Leibovitz et al., "The Growth and Maintenance of Tissue-Cell Cultures in Free Gas Exchange with the Atmosphere," Amer. J. of Hygiene, 78:173-180 (1963).
Lindsey et al., "Multiplex polymerase chain reaction for identification of *Escherichia coli*, *Escherichia albertii* and *Escherichia fergusonii*," J. of Microbiol. Meth., 140: 1-4 (2017).
Maeder et al., "Rapid 'Open-Source' Engineering of Customized Zinc-Finger Nucleases for Highly Efficient Gene Modification," Mol. Cell, 31(2): 294-301 (2008).
Makarova et al., "A putative RNA-interference-based immune system in prokaryotes: computational analysis of the predicted enzymatic machinery, functional analogies with eukaryotic RNAi, and hypothetic mechanisms of action," Biology Direct 1(7) (2006).
Makarova et al., "Evolution and classification of the CRISPR-Cas systems," Nat Rev Microbiol. 9(6): 467-477 (2011).
Makarova et al., "Unification of Cas protein families and a simple scenario for the origin and evolution of CRISPR-Cas systems," Biology Direct 6(38) (2011).
Mali et al., "RNA-guided Human Genome Engineering via Cas9," Science, 339(6121) 823:826 (2013).
Martick et al., "A Discontinuous Hammerhead Ribozyme Embedded in a Mammalian Messenger RNA," Nature, 454(7206): 899-902 (2008).
Mason et al., "Identifying Bottlenecks in Transient and Stable Production of Recombinant Monoclonal-Antibody Sequence Variants in Chinese Hamster Ovary Cells," Biotechnology Progress, 28(3): 846-855 (2012).
Meng X et al., "Targeted Gene Inactivation in Zebrafish Using Engineered Zinc-Finger Nucleases," Nat. Biotechnol., 26(6): 695-701 (2008).
Miller et al., "A TALE Nuclease Architecture for Efficient Genome Editing," Nat. Biotechnol. 29(2): 143-148 (2011).
Miller et al., "Improved specificity of TALE-based genome editing using an expanded RVD repertoire," Nat. Methods, 12: 465-471 (2015).

(56) References Cited

OTHER PUBLICATIONS

Moore et al., "Culture of Normal Human Leukocytes," JAMA, 199(8): 519-524 (1967).

Moretto et al., "Process Raman Spectroscopy for In-Line CHO Cell Culture Monitoring," American Pharmaceutical Review, 14 (2011).

Nishimasu et al., "Crystal Structure of Cas9 in Complex with Guide RNA and Target DNA," Cell 156: 935-949 (2014).

Nissim et al., "Multiplexed and Programmable Regulation of Gene Networks with an Integrated RNA and CRISPR/Cas Toolkit in Human Cells," Mol. Cell 54(4): 698-710 (2014).

Obrezanova et al., "Aggregation risk prediction for antibodies and its application to biotherapeutic development," mAbs, 7(2): 352-363 (2015).

Ohtsuka et al., "An Alternative Approach to Deoxyoligonucleotides and Hybridization Probes by Insertion of Deoxyinosine at Ambiguous Codon Positions," J. Biol. Chem., 260(5): 2605-2608 (1985).

Pabo et al., "Design and Selection of Novel Cys2His2 Zinc Finger Proteins," Annu Rev Biochem 70: 313-340 (2001).

Papadakis et al., "Promoters and Control Elements: Designing Expression Cassettes for Gene Therapy," Curr Gene Ter 4(1): 89-113 (2004).

Pontiller et al., "Identification of CHO Endogenous Promoter Elements Based on a Genomic Library Approach," Mol. Biotech., 39: 135-139 (2008).

Port et al., "Augmenting CRISPR applications in Drosophila with tRNA-flanked sgRNAs." Nat. Meth., 13(10): 852-854 (2006).

Porter et al., "Strategies for selecting recombinant CHO cell lines for cCMP manufacturing: improving the efficiency of cell line generation," Biotechnol. Prog., 26: 1446-1455 2010.

Rossolini et al., "Use of deoxyinosine-containing primers vs degenerate primers for polymerase chain reaction based on ambiguous sequence information," Mol. and Cell. Probes, 8(2): 91-98 (1994).

Riethoven et al., "Regulatory Regions in DNA: Promoters, Enhancers, Silencers, and Insulators," Computational Biology of Trascription Factor Binding, Methods in Molecular Biology, 674 (2010).

Sander et al., "Selection-Free Zinc-Finger Nuclease Engineering by Context-Dependent Assembly (CoDA)," Nat Methods 8(1): 67-69 (2011).

Smales et al., "Comparative proteomic analysis of GS-NS0 murine myeloma cell lines with varying recombinant monoclonal antibody production rate," Biotechnol. and Bioeng. 88: 474-488 (2004).

Stansfield et al., "Dynamic analysis of GS-NS0 cells producing a recombinant monoclonal antibody during fed-batch culture," Biotechnol. and Bioeng. 97: 410-424 (2006).

Struebel et al., "TAL Effector RVD Specificities and Efficiencies," Nat. Biotechnol. 30(7): 593-595 (2012).

Tigges et al., "Xbp1-based Engineering of Secretory Capacity Enhances the Productivity of Chinese Hamster Ovary Cells," Metab. Eng. 8(3): 264-272 (2006).

Wolfe et al., "Analysis of Zinc Fingers Optimized via Phage Display: Evaluating the Utility of a Recognition Code," J. Mol. Biol. 285(5): 1917-1934 (1999).

Wolfe et al., "DNA Recognition by Cys2His2 Zinc Finger Proteins," Annual Rev. Biophys. Biomol. Struct. 29: 183-212 (2000).

Xia et al., "High Levels of Protein Expression Using Different Mammalian CMV Promoters in Several Cell Lines," Protein Expr. Purif. 45(1): 115-124 (2006).

Xiao et al., "CasOT: A Genome-Wide Cas9/gTNA Off-Target Searching Tool," Bioinformatics, 30(8): 1180-1182 (2014).

Xie et al., "Boosting CRISPR/Cas9 multiplex editing capability with the endogenous tRNA-processing system," PNAS 112(11): 3570-3575 (2015).

Xu et al., "Sequence determinants of improved CRISPR sgRNA design," Genome Res. 25(8): 1147-1157 (2015).

Yang et al., "Complete decoding of TAL effectors for DNA recognition," Cell Res. 24: 628-631 (2014).

Zhang et al., "Efficient Construction of Sequence-Specific TAL Effectors for Modulating Mammalian Transcription," Nat. Biotechnol. 29(2): 149-152 (2011).

International Search Report in PCT/US2018/037792 mailed Oct. 23, 2018.

* cited by examiner

UNIVERSAL SELF-REGULATING MAMMALIAN CELL LINE PLATFORM FOR THE PRODUCTION OF BIOLOGICS

RELATED APPLICATIONS

This application claims priority to U.S. Ser. No. 62/521,005, filed Jun. 16, 2017, the contents of which is incorporated herein by reference in its entirety.

FIELD OF THE INVENTION

The present invention relates to methods and compositions for modulating the expression of a product, e.g., a recombinant protein, by a cell and cell lines using genetic control circuits that respond to cellular stress.

BACKGROUND

Recombinant therapeutic proteins are commonly expressed in cell expression systems, e.g., mammalian cell expression systems. In 2014, the total number of market approved biopharmaceuticals was 212, and 56% of the therapeutic products approved for market by the FDA are produced in mammalian cell lines. However, the high cost associated with production contributes to increasing global health costs.

Moreover, next generation protein biologics (NGBs) such as next generation fusion proteins, multimeric glycoproteins, or next generation antibodies often have a complex and/or non-natural structure and are proving more difficult to express than molecules such as monoclonal antibodies. Current host cell lines do not evolve pathways for the efficient synthesis and secretion of NGBs, resulting in significantly reduced growth, low productivity and often resulting in products with poor product quality (PQ) attributes. Thus, these NGBs are considered difficult to express, in which the productivity and product quality do not meet clinical and market needs. Accordingly, there is an increasing need to develop and produce recombinant biotherapeutics rapidly, efficiently, and cost-effectively while maintaining final product quality.

Current gene expression systems for the synthesis of recombinant proteins using mammalian cell lines are constitutively active and direct transcription of the recombinant protein product genes irrespective of the cell culture conditions or the metabolism of the host cell. Such systems fail to coordinate product gene transcription with the intracellular state of the host cell line, such as occurs for endogenous host cell proteins, leading to cellular stress and poor product outcomes, particularly for NGBs. As NGBs push our current cell lines and gene expression systems to the limit, there is a need to better coordinate transcription of recombinant protein product genes with the overall metabolism of the host cell. This would help to reduce the level of cellular stress and better utilize the existing capabilities of our mammalian cell factories to produce high levels of product with the correct product quality attributes (e.g. glycosylation profile, correct folding structures, etc.).

When mammalian host cell lines are constrained to constitutively synthesize a high level of a recombinant protein product, particularly a NGB or difficult to express protein, a cellular stress pathway termed the unfolded protein response (UPR) will be activated by an accumulation of misfolded protein. This leads to a general global downturn in protein translation to allow the cell sufficient time to correctly process and fold the current protein load. Activation of such a stress response is inhibitory not only to overall yield of a recombinant protein product but also to a desirable PQ profile.

SUMMARY OF THE INVENTION

In one aspect, the present disclosure features a genetic control circuit that uses a repressor polypeptide (e.g., a version of the Cas9 protein (from the CRISPR-Cas9 gene editing system) that lacks nuclease activity (dCas9)) to reduce the transcription rate of an exogenous therapeutic polypeptide encoding gene in response to a change in condition (e.g., an increase in cellular stress). In response to the change in condition, a condition-dependent gene promoter increases the transcription rate of the repressor polypeptide gene. The repressor polypeptide produced binds to the exogenous therapeutic polypeptide encoding gene or to a control element operably linked to the exogenous therapeutic polypeptide encoding gene. In some embodiments, where the repressor polypeptide comprises a version of Cas9, the repressor polypeptide binds to the exogenous therapeutic polypeptide encoding gene or to a control element operably linked to the exogenous therapeutic polypeptide encoding gene due to the co-expression of at least one guide RNA (gRNA) with homology to the exogenous therapeutic polypeptide encoding gene, or control element operably linked thereto. When the repressor polypeptide is bound to the exogenous therapeutic polypeptide encoding gene, or control element operably linked thereto, the transcription rate of the exogenous therapeutic polypeptide encoding gene is reduced, leading to a decrease in intracellular mRNA copy number for the therapeutic polypeptide. In some embodiments the change in condition is a change in cellular stress, e.g., an increase in cellular stress or the transition from an unstressed to a stressed state, and the change in cellular stress is activation of the mammalian UPR, although other cellular stress responses can also be appropriated for this use. In an embodiment, the exogenous therapeutic polypeptide encoding gene is transcribed under the control of the hCMV promoter, although other promoters may also be used (e.g. mCMV, and hybrid CMV promoters). By reducing the rate of exogenous therapeutic polypeptide encoding gene transcription the biosynthetic load of exogenous therapeutic polypeptide on the host cell is reduced, thereby alleviating an initial cellular stress response. In this way the host cell line can self-regulate the transcription rate of the recombinant protein product gene and avoid a prolonged activation of the initial cellular stress response. Once the initial stress response has been alleviated, the transcription rate of the exogenous therapeutic polypeptide is de-repressed over time. Over time this may result in an overall increase in the yield of a recombinant protein as the cell optimally coordinates recombinant gene expression with the overall physiological status of the cell to better utilize the cellular biosynthetic capacity.

In one aspect, the disclosure features a genetic control circuit comprising: a first control element, e.g., a first promoter element, operably linked to a sequence encoding an exogenous therapeutic polypeptide; and a second control element, e.g., second promoter element, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased. In some embodiments, the genetic control circuit further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a cell, e.g., a CHO cell, comprising: a first control element, e.g., a first promoter, operably linked to a sequence encoding an exogenous therapeutic polypeptide; and a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased. In some embodiments, the cell further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition. In some embodiments, the cell further optionally comprises fourth, fifth, sixth, seventh, eighth, ninth, tenth or more control elements. In one embodiment, an entire signaling pathway is controlled by controlling a single node in the pathway using the methods disclosed herein. In some embodiments, the entire signaling pathway is controlled by controlling a multiple metabolic branches of the signaling pathway, for example by using different promoters to regulate different sequences of the pathway. Thus, the method of the invention provides several layers of control in the self-regulating cell. For example, translation elongation initiation factor is an example of a global node point that can control multiple pathways. Alternatively, an example of a local node point is the gene encoding for the enzyme galactosyltransferase, which adds galactose residues to the glycans attached to Asn297 of the recombinant antibody heavy chain polypeptide, and is required for creating N-glycans with both galactose and sialic acid residues.

In one aspect, the disclosure features a cell, e.g., a CHO cell, comprising: a first control element, e.g., a first promoter, operably linked to an insertion site, e.g., a restriction site or SSI site; and a second control element, e.g., a second promoter, operably linked to a sequence encoding a repressor polypeptide; wherein, the insertion site is suitable for insertion of a sequence encoding an exogenous therapeutic polypeptide, the second control element has a first level of activity under a first condition and a second level of activity under a second condition, and in the presence of the second condition, the expression of the therapeutic polypeptide is modulated, e.g., decreased. In some embodiments, the cell further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a kit for expression of a therapeutic polypeptide comprising a cell, e.g., a CHO cell, comprising: a first control element, e.g., a first promoter, operably linked to a sequence encoding an exogenous therapeutic polypeptide; and a second control element, e.g., second promoter, operably linked to a sequence encoding a repressor polypeptide; wherein the second control element has a first level of activity under a first condition and a second level of activity under a second condition, and in the presence of the second condition, the expression of the therapeutic polypeptide is modulated, e.g., decreased. In some embodiments, the cell further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a kit for expression of a therapeutic polypeptide comprising a cell, e.g., a CHO cell, comprising: a first control element, e.g., a first promoter, operably linked to an insertion site, e.g., a restriction site or SSI site; and a second control element, e.g., second promoter, operably linked to a sequence encoding a repressor polypeptide; wherein, the insertion site is suitable for insertion of a sequence encoding an exogenous therapeutic polypeptide, the second control element has a first level of activity under a first condition and a second level of activity under a second condition, and in the presence of the second condition, the expression of the therapeutic polypeptide is modulated, e.g., decreased. In some embodiments, the cell further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a kit for expression of a therapeutic polypeptide comprising one or more nucleic acids comprising: a first control element, e.g., a first promoter, operably linked to a sequence encoding an exogenous therapeutic polypeptide; and a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased. In some embodiments, the kit further optionally comprises a nucleic acid comprising a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition. In one aspect, the disclosure features a kit for expression of a therapeutic polypeptide comprising one or more nucleic acids comprising: a first control element, e.g., a first promoter, operably linked to an insertion site, e.g., a restriction site; and a second control element, e.g., second promoter, operably linked to a sequence encoding a repressor polypeptide; wherein, the insertion site is suitable for insertion of a sequence encoding an exogenous therapeutic polypeptide, the second control element has a first level of activity under a first condition and a second level of activity under a second condition, and in the presence of the second condition, the expression of the therapeutic polypeptide is modulated, e.g., decreased. In some embodiments, the kit further optionally comprises a nucleic acid comprising a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a method of making a therapeutic polypeptide, comprising: a) acquiring a cell, e.g., a CHO cell, comprising: a first control element, e.g., a first promoter, operably linked to a sequence encoding an exogenous therapeutic polypeptide; and a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased, and b) culturing the cell under conditions that allow for making of the therapeutic polypeptide, thereby making the therapeutic polypeptide. In some embodiments, the cell of a) further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a method of making a therapeutic polypeptide, comprising: a) acquiring a cell, e.g., a CHO cell; b) forming or providing in the cell, a first nucleic acid sequence that encodes a first control element, e.g., a first promoter, operably linked to a sequence encoding an exogenous therapeutic polypeptide; and c) forming or providing in the cell, a second nucleic acid that encodes a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased; and d) culturing the cell under conditions that allow for making of the therapeutic polypeptide, thereby making the therapeutic polypeptide. In some embodiments, the method further optionally comprises an additional step between c) and d), comprising: forming or providing in the cell, a third nucleic acid that encodes a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a method of making a therapeutic polypeptide, comprising: a) acquiring a cell, e.g., a CHO cell; b) forming or providing in the cell, a first nucleic acid sequence that encodes a first control element, e.g., a first promoter, operably linked to a sequence encoding an exogenous therapeutic polypeptide; c) forming or providing in the cell, a second nucleic acid that encodes a second control element, e.g., second promoter, operably linked to a sequence encoding a repressor polypeptide; and optionally d) forming or providing in the cell, a third nucleic acid that encodes a third control element operably linked to a sequence encoding one or more (e.g., 1, 2, 3, 4, 5, 6, 7, 8, 9, 10 or more) gRNAs, wherein, the second control element has a first level of activity under a first condition and a second level of activity under a second condition, and in the presence of the second condition, the expression of the therapeutic polypeptide is modulated, e.g., decreased; and e) culturing the cell under conditions that allow for making of the therapeutic polypeptide, thereby making the therapeutic polypeptide. In embodiments, steps a-d can be performed in any order. In some embodiments, the third control element has a first level of activity under a first condition and a second level of activity under a second condition.

In one aspect, the disclosure features a nucleic acid comprising: a first control element, e.g., a first promoter, operably linked to a sequence encoding an exogenous therapeutic polypeptide; and a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased. In some embodiments, the nucleic acid further optionally comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the disclosure features a nucleic acid comprising: a first control element, e.g., a first promoter, operably linked to an insertion site, e.g., a restriction site; and a second control element, e.g., second promoter, operably linked to a sequence encoding a repressor polypeptide; wherein, the insertion site is suitable for insertion of a sequence encoding an exogenous therapeutic polypeptide, the second control element has a first level of activity under a first condition and a second level of activity under a second condition, and in the presence of the second condition, the expression of the therapeutic polypeptide is modulated, e.g., decreased. In some embodiments, the nucleic acid further comprises a third control element, e.g., third promoter, operably linked to a sequence encoding one or more (e.g., 1, 2, 3, 4, 5, 6, 7, 8, 9, 10 or more) gRNAs. In some embodiments, the third control element has a first level of activity under a first condition and a second level of activity under a second condition.

In one aspect, the invention disclosure features a method of making a cell of the disclosure, comprising: a) forming or providing in the cell, a first nucleic acid sequence that encodes a first control element, e.g., a first promoter, operably linked to a sequence encoding an exogenous therapeutic polypeptide; and b) forming or providing in the cell, a second nucleic acid that encodes a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased or increased, thereby making the cell. In some embodiments, the method further comprises a step c) comprising: forming or providing in the cell, a third nucleic acid sequence that encodes a third control element, e.g., third promoter, operably linked to a sequence encoding one or more (e.g., 1, 2, 3, 4, 5, 6, 7, 8, 9, 10 or more) gRNAs. In embodiments, steps a-c can be performed in any order. In some embodiments, the third control element has a first level of activity under a first condition and a second level of activity under a second condition.

In one aspect, the invention disclosure features a method of making a cell able to produce economically enhanced yields of a polypeptide, e.g., an exogenous therapeutic polypeptide, with desired product quality attributes, comprising: a) forming or providing in the cell, a first nucleic acid sequence that encodes a first control element, e.g., a first promoter, operably linked to a sequence encoding an exogenous therapeutic polypeptide; and b) forming or providing in the cell, a second nucleic acid that encodes a second control element, e.g., second promoter, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased or increased, thereby making the cell able to produce economically enhanced yields of a polypeptide, e.g., an exogenous therapeutic polypeptide, with desired product quality attributes. In some embodiments, the method further comprises a step c) comprising: forming or providing in the cell, a third nucleic acid sequence that encodes a third control element, e.g., third promoter, operably linked to a sequence encoding one or more (e.g., 1, 2, 3, 4, 5, 6, 7, 8, 9, 10 or more) gRNAs. In embodiments, steps a-c can be performed in any order. In some embodiments, the third control element has a first level of activity under a first condition and a second level of activity under a second condition.

In one aspect, the invention disclosure features a cell comprising: a first control element selected from Table 5 operably linked to a sequence encoding an exogenous therapeutic polypeptide selected from Tables 1-4; a second control element selected from Table 6 operably linked to a sequence encoding aCas9 polypeptide; and one or more gRNA sequences that are constitutively expressed; wherein, the second control element has a first level of activity under a first condition and a second level of activity under a second condition, and in the presence of the second condition, the expression of the therapeutic polypeptide is modulated.

In one aspect, the invention disclosure features a plurality of the cells described herein, wherein one or more cells comprise the first condition and one or more cells comprise the second condition.

BRIEF DESCRIPTION OF THE FIGURES

In FIG. 1A, production of recombinant protein induces stress/toxicity, which activates the production of repressor, thereby entailing the direct inhibition of recombinant or therapeutic polypeptide expression. In FIG. 1B, the resulting inhibition of recombinant or therapeutic polypeptide expression in 1A eventually eliminates the stress/toxicity, removing the activation of repressor, and indirectly leading to a passive increase in recombinant or therapeutic polypeptide expression. In effect this system may lead to a temporal oscillation in recombinant or therapeutic polypeptide expression around a specific level which induces stress/toxicity in the host cell (FIG. 1C). Further optional layers of control may be applied to this basic circuit, including a positive activator of recombinant or therapeutic polypeptide expression which becomes active once the cellular stress/toxicity has been alleviated (FIG. 1D).

FIG. 6A shows the genetic control circuit contained on an expression vector, where the dCas9 gene is under the Grp78 promoter, and three gRNA sequences with specificity to the hCMV promoter (gRNAs 1, 2 and 3), are each under separate constitutive U6 promoters (gRNA123 circuit). A variant of this vector contained the gRNA14 sequence in place of the gRNA 1, 2 and 3 sequences (sgRNA 14 circuit). FIG. 6B shows the recombinant protein concentration produced from stable CHO pools containing the control circuits after transient transfection with expression vectors encoding for several difficult-to-express recombinant proteins. The recombinant protein concentration was determined 6 days after transient transfection. The parental CHO cell line lacks the genetic control circuit. Error bars represent the standard deviation of triplicate transfections for all data points except for the transfection of the parental cell line with the blinatumomab vector, which was performed in duplicate. FIG. 6C shows the recombinant protein concentration at day 6 produced from stable CHO pools containing the control circuits after transient transfection with expression vectors encoding for a highly aggregating Mab H9K7. At 24 h post transfection half of the transient transfection flasks were treatment with the UPR-inducer tunicamycin TM at a concentration of 0.1 µg/mL. Error bars represent the standard deviation of triplicate transfections.

FIG. 7A shows the aggregation data for the cell culture supernatant samples assayed for concentration in FIG. 6B, and FIG. 7B showing the aggregation data for the cell culture supernatant samples assayed for concentration in FIG. 6C.

DETAILED DESCRIPTION OF THE INVENTION

Definitions

Figure 1A:
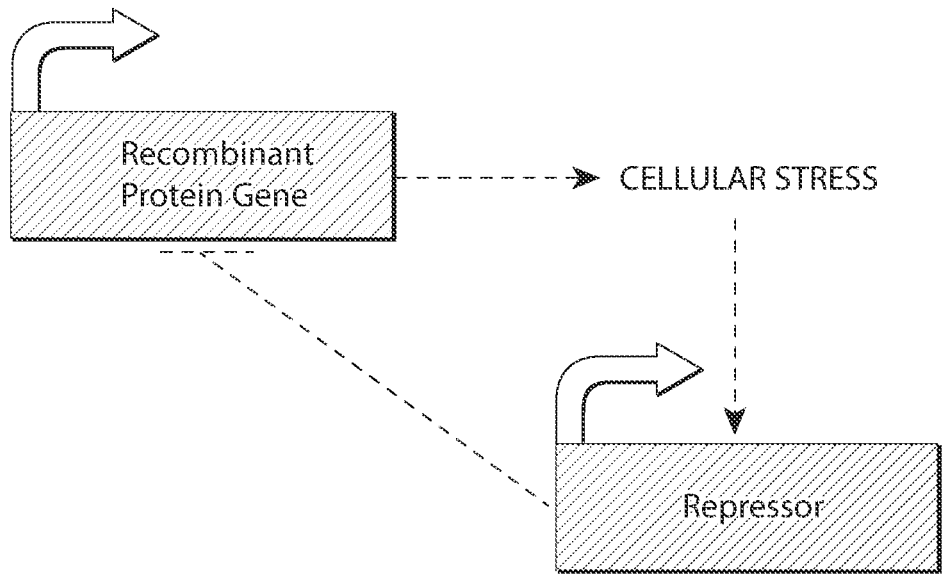
FIGS. 1A, 1B, 1C, and 1D show schematics of the design principle for the genetic control circuit regulating transcription of a recombinant or therapeutic polypeptide product gene in response to a condition, e.g., cellular stress.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variation Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

As used herein, the term "genetic control circuit" refers to an arrangement of gene expression elements, e.g. protein encoding sequences, control elements, or promoter elements, wherein the genetic control circuit comprises at least one protein encoding sequence encoding a recombinant or therapeutic polypeptide product, and wherein the genetic control circuit comprises other gene expression elements that regulate the expression of the recombinant or therapeutic polypeptide product in a condition dependent manner. In one embodiment, a genetic control circuit may comprise, in lieu of the at least one protein encoding sequence encoding a recombinant or therapeutic polypeptide product, a suitable insertion site, e.g. restriction site, recombination target site, or landing pad, for the insertion of one or more protein encoding sequences. In some embodiments, a genetic control circuit may comprise a contiguous portion of a single nucleic acid molecule, multiple discrete portions of a single nucleic acid molecule, or be distributed across more than one nucleic acid molecule.

As used herein, the term "control element" refers to a nucleic acid suitable to regulate (e.g. increase or decrease) the expression of a coding sequence, e.g., a gene. Control elements may comprise promoter sequences, enhancer sequences, or both promoter and enhancer sequences. Control elements may comprise continuous nucleic acid sequences, discontinuous nucleic acid sequences (sequences interrupted by other coding or non-coding nucleic acid sequences), or both. A single control element may be comprised on a single nucleic acid or more than one nucleic acid. In an embodiment, a control element may comprise sequences 5' or 3' of a coding sequence, e.g., the coding sequence of a recombinant, therapeutic, or repressor polypeptide. In an embodiment, a control element may comprise sequences within one or more introns of a gene, e.g., a gene encoding a recombinant, therapeutic, or repressor polypeptide. In an embodiment, a control element may be comprised, in part or in its entirety, within sequences 5' or 3' of a coding sequence, e.g., the coding sequence of a recombinant, therapeutic, or repressor polypeptide. In an embodiment, a control element may be comprised in part or in its entirety, within a coding sequence, e.g., the coding sequence of a recombinant, therapeutic, or repressor polypeptide. In an embodiment, a control element may be comprised in part or in its entirety, within one or more introns of a gene, e.g., a gene encoding a recombinant, therapeutic, or repressor polypeptide. In an embodiment, a single control element may comprise nucleic acid sequences i) proximal to (e.g., adjacent to or contained within) a gene, e.g., a gene encoding a recombinant, therapeutic, or repressor polypeptide, or ii) distal to (e.g., separated by 10 or more, 100 or more, 1000 or more, or 10,000 or more bases, or disposed on a distinct and separate nucleic acid) a gene, e.g., a gene encoding a recombinant, therapeutic, or repressor polypeptide.

As used herein, the term "promoter element", refers to a sequence having sufficient sequences from a naturally occurring or engineered promoter such that operably linking a coding sequence to the promoter element results in the expression of the coding sequence. For example, a cytomegalovirus (CMV) promoter element comprises all or an active fragment of the CMV promoter, e.g., all or an active fragment of the CMV promoter including optionally intron A and/or UTR sequences. In an embodiment, a CMV promoter element, differs at no more than 5, 10, 20, 30, 50, or 100 nucleotides from a naturally occurring or engineered variant CMV promoter. In an embodiment, a CMV promoter element, differs at no more than 1, 5, 10, or 50% of its nucleotides from a naturally occurring or engineered variant CMV promoter. An engineered promoter is a promoter comprising synthetic (non-naturally occurring) sequences. In an embodiment, an engineered promoter comprises non-naturally occurring rearrangements of naturally occurring transcription regulatory elements (e.g., as described in Brown et al. Biotechnology and Bioengineering, Vol. 111, No. 8, August, 2014). In an embodiment, a promoter element for use in the cells, nucleic acids, and methods of the disclosure has sufficient sequences from an engineered promoter, e.g., a promoter comprising synthetic (non-naturally occurring) sequences, that operably linking a coding sequence to the promoter element results in the expression of the coding sequence. Promoter elements, as used herein, may be constitutive, regulated, repressible, strong, weak, or other properties of the promoter sequences the promoter elements comprise. In an embodiment, a promoter element may comprise sequences 5' or 3' of a coding sequence, e.g., the coding sequence of a recombinant, therapeutic, or repressor polypeptide. In an embodiment, a promoter element may comprise sequences within one or more introns of a gene, e.g., a gene encoding a recombinant, therapeutic, or repressor polypeptide. In an embodiment, a promoter element may be comprised, in part or in its entirety, within sequences 5' or 3' of a coding sequence, e.g., the coding sequence of a recombinant, therapeutic, or repressor polypeptide. In an embodiment, a promoter element may be comprised in part or in its entirety, within a coding sequence, e.g., the coding sequence of a recombinant, therapeutic, or repressor polypeptide. In an embodiment, a promoter element may be comprised in part or in its entirety, within one or more introns of a gene, e.g., a gene encoding a recombinant, therapeutic, or repressor polypeptide.

As used herein, the term "operably linked" refers to a relationship between a nucleic acid sequence encoding a polypeptide and a control element, wherein the sequence encoding a polypeptide and the control element are operably linked if they are disposed in a manner suitable for the control element to regulate the expression of the sequence encoding a polypeptide. Thus for different control elements, operably linked will constitute different dispositions of the sequence encoding a polypeptide relative to the control element. For example, a sequence encoding a polypeptide may be operably linked to a control element comprising a promoter element if the promoter element and sequence encoding a polypeptide are disposed proximal to one another and on the same nucleic acid. In another example, a sequence encoding a polypeptide may be operably linked to a control element comprising an enhancer sequence that operates distally if the enhancer sequence and sequence encoding a polypeptide are disposed a suitable number of bases apart on the same nucleic acid, or even on distinct and separate nucleic acids. An insertion site, e.g., a restriction site, landing pad, or SSI site, may also be operably linked to a control element, if a sequence encoding a polypeptide inserted into the insertion site would be operably linked to the control element.

As used herein, the term "endogenous" refers to any material from or naturally produced inside an organism, cell, tissue or system.

As used herein, the term "recombination target site" is a stretch of nucleotides being necessary for and allowing, together with a recombinase, a targeted recombination and defining the location of such a recombination.

As used herein, the term "recombination target sites" used in conjunction with "flank" or "flanking" a gene, e.g., a gene encoding a recombinant, e.g., therapeutic, repressor, or selective marker, polypeptide, means that the recombination target sites are located 5' and 3' to said gene, that means one target site is located 5' and the other target site is located 3' to the gene coding sequence of interest. The recombination target sites may be located directly adjacent or at a defined distance to the gene coding sequence of interest. The flanking sequences, in particular the flanking recombination target sites, are positioned in forward or reverse orientation, preferably both are in forward or preferably both are in reverse orientation.

As used herein, the term "exogenous" refers to any material introduced to or produced outside of an organism, cell, tissue or system. Accordingly, "exogenous nucleic acid" refers to a nucleic acid that is introduced to or produced outside of an organism, cell, tissue or system. In an embodiment, sequences of the exogenous nucleic acid are not naturally produced, or cannot be naturally found, inside the organism, cell, tissue, or system that the exogenous nucleic acid is introduced into. Similarly, "exogenous polypeptide" refers to a polypeptide that is not naturally produced, or cannot be naturally found, inside the organism, cell, tissue, or system that the exogenous polypeptide is introduced to, e.g., by expression from an exogenous nucleic acid sequence.

As used herein, the term "heterologous" refers to any material from one species, when introduced to an organism, cell, tissue or system from a different species.

As used herein, the terms "nucleic acid," "polynucleotide," or "nucleic acid molecule" are used interchangeably and refers to deoxyribonucleic acid (DNA) or ribonucleic acid (RNA), or a combination of a DNA or RNA thereof, and polymers thereof in either single- or double-stranded form. The term "nucleic acid" includes, but is not limited to, a gene, cDNA, or an mRNA. In one embodiment, the nucleic acid molecule is synthetic (e.g., chemically synthesized or artificial) or recombinant. Unless specifically limited, the term encompasses molecules containing analogues or derivatives of natural nucleotides that have similar binding properties as the reference nucleic acid and are metabolized in a manner similar to naturally or non-naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260.2605-2608 (1985); and Rossolini et al., Mol. Cell. Probes 8:91-98 (1994)).

As used herein, the terms "peptide," "polypeptide," and "protein" are used interchangeably, and refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

As used herein, "recombinant polypeptide" or "recombinant protein" refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering (of the cell or of a precursor cell). E.g., at least one nucleotide was altered, e.g., it was introduced into the cell or it is the product of a genetically engineered rearrangement. For example, a recombinant polypeptide may also be a therapeutic polypeptide.

As used herein, "therapeutic polypeptide" refers to a polypeptide with utility to human or animal health or medicine, that is produced, e.g., expressed, by a cell which has been modified or engineered to produce the therapeutic polypeptide. In one embodiment, the therapeutic polypeptide is a naturally occurring polypeptide or a non-naturally occurring polypeptide, e.g., a synthetic polypeptide. In one embodiment, a portion of the therapeutic polypeptide is naturally occurring, while another portion of the therapeutic polypeptide is non-naturally occurring. In one embodiment, the therapeutic polypeptide is a recombinant polypeptide. In one embodiment, the therapeutic polypeptide is suitable for diagnostic or pre-clinical use. In another embodiment, the therapeutic polypeptide is suitable for therapeutic use, e.g., for treatment of a disease. In one embodiment, the therapeutic polypeptide is selected from Table 1-4. In some embodiments, the modified or engineered cells comprise an exogenous nucleic acid that controls expression or encodes the therapeutic polypeptide. In other embodiments, the modified or engineered cells comprise other molecules, e.g., that are not nucleic acids, that controls the expression or construction of the therapeutic polypeptide in the cell.

As used herein, "repressor polypeptide" refers to a polypeptide that controls expression of another polypeptide (e.g., a therapeutic polypeptide) that is produced, e.g., expressed, by a cell which has been modified or engineered to produce the repressor polypeptide. In one embodiment, the repressor polypeptide is a naturally occurring polypeptide or a non-naturally occurring polypeptide, e.g., a synthetic polypeptide. In one embodiment, a portion of the repressor polypeptide is naturally occurring, while another portion of the repressor polypeptide is non-naturally occurring. In one embodiment, the repressor polypeptide is a recombinant polypeptide. In some embodiments, a repressor polypeptide decreases expression of a therapeutic polypeptide. In some embodiments, a repressor polypeptide completely eliminates expression of a therapeutic polypeptide. In some embodiments, expression of a repressor polypeptide is regulated. For example, the repressor polypeptide is highly expressed under one set of conditions and expression of the repressor polypeptide is inhibited, e.g., decreased or completely eliminated, under another set of conditions.

As used herein, "level of activity" refers to a measure of the strength of expression induced by a control element or promoter element. For example, a control element may have a high level of activity such that a coding sequence operably linked to the control element is strongly expressed.

As used herein, "condition" refers to a value of cellular and/or environmental parameters that can influence the level of activity of a control element or promoter element. A condition can include one value of cellular and environmental parameters, or a condition can include more than one (e.g., two, three, four, five, six, or more) values of cellular and environmental parameters. For example, a control element can have a first level of activity under a first condition and a second level of activity under a second condition. Cellular and environmental parameters include, but are not limited to, the levels of one or more polypeptides, the compartment localized levels of one or more polypeptides (e.g., nuclear, cytosolic, or endoplasmic reticulum localized) the level of activation of cellular signaling pathways, e.g., the stress response, unfolded protein response, heat shock response, etc., the level of signaling molecules (e.g., $Ca^{+2}$, cAMP, glucose, ATP, etc.), temperature, pH, cell cycle/growth phase, cell density of culture, and nutrient availability.

A Cas9 molecule or Cas9 polypeptide, as that term is used herein, refers to a molecule or polypeptide that can interact with a guide RNA (gRNA) molecule and, in concert with the gRNA molecule, home or localizes to a site which comprises a target domain and PAM sequence. Cas9 molecule and Cas9 polypeptide, as those terms are used herein, include naturally occurring Cas9 molecules and engineered, altered, or modified Cas9 molecules or Cas9 polypeptides that differ, e.g., by at least one amino acid residue, from a reference sequence, e.g., the most similar naturally occurring Cas9 molecule or a sequence. Exemplary Cas9 molecule or Cas9 polypeptide sequences can be found in WO2015/157070, hereby incorporated by reference in its entirety. Cas9 molecules or Cas9 polypeptides include Cas9 molecules that have DNA cleaving and nicking activity, and others, e.g., dCas9 molecules or dCas9 polypeptides, which do not appreciably cleave or nick DNA.

Overview

Figure 1B:
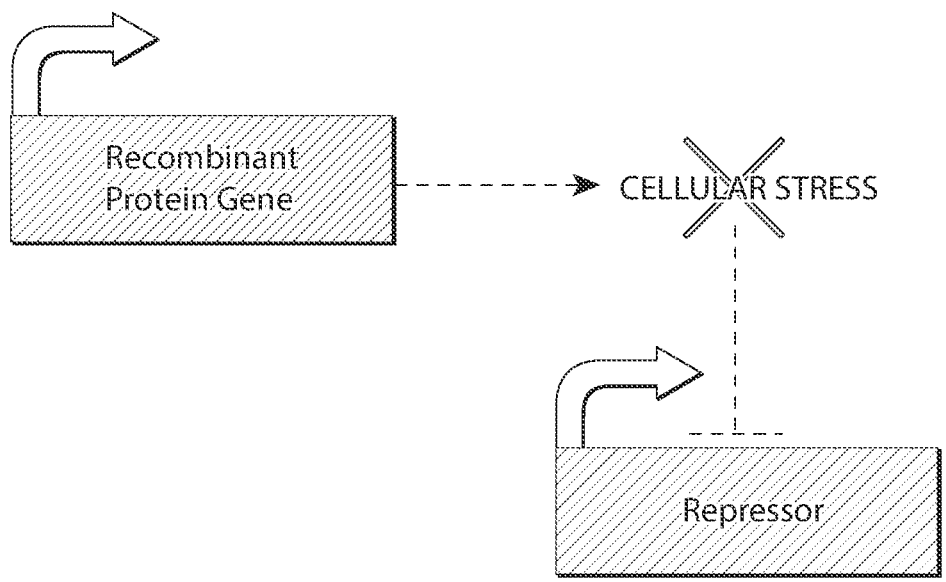
Figure 1C:
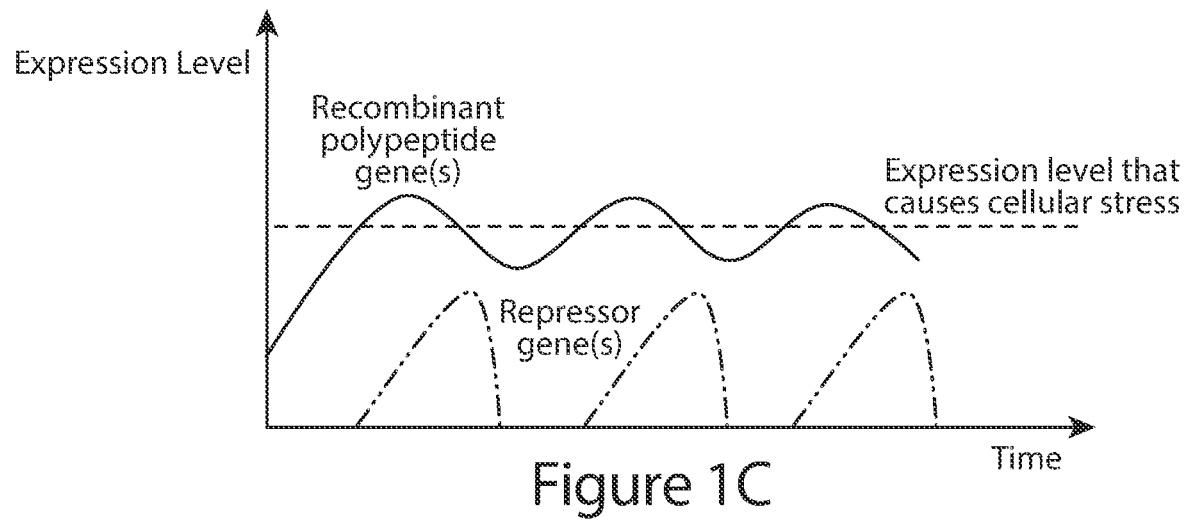
Figure 1D:
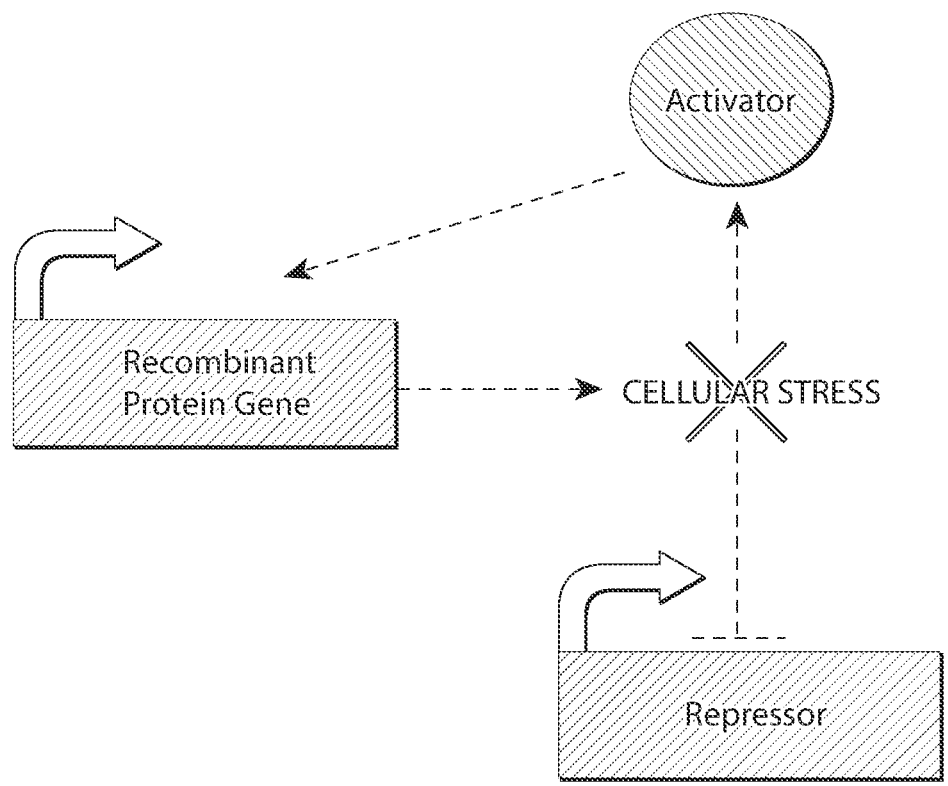

In one aspect, the current disclosure provides genetic control circuits, nucleic acids, cells, methods for making a cell or cell lines, and methods for fine-tuning the transcription rate of a recombinant or therapeutic protein product gene or genes in response to a change in cellular or environmental conditions, e.g., a change in cellular stress response, e.g., the unfolded protein response (UPR). An example of the general design principle of the disclosure for the genetic control circuit is depicted in FIG. 1A and FIG. 1B. In this non-limiting schematic example the production of a recombinant protein product induces stress/toxicity, which activates the production of a repressor polypeptide, thereby inhibiting recombinant polypeptide product expression. Removal of the stress signal deactivates expression of repressor polypeptide. Alleviation of the inhibition entails the re-activation of recombinant polypeptide product production.

Products

Provided herein are genetic control circuits, cells, and methods for identifying, selecting, or making a cell or cell line capable of producing high yields of a product, e.g., an exogenous therapeutic polypeptide. The products encompassed by the present disclosure include, but are not limited to, molecules, nucleic acids, polypeptides (e.g., recombinant and/or therapeutic polypeptides), or hybrids thereof, that can be produced by, e.g., expressed in, a cell. In some embodiments, the cells are engineered or modified to produce the product. Such modifications include introducing molecules that control or result in production of the product. For example, a cell is modified by introducing an exogenous nucleic acid that encodes a polypeptide, e.g., a recombinant polypeptide, and the cell is cultured under conditions suitable for production, e.g., expression and secretion, of the polypeptide, e.g., recombinant polypeptide. In another example, a cell is modified by introducing an exogenous nucleic acid that controls, e.g., increases, expression of a polypeptide that is endogenously expressed by the cell, such that the cell produces a higher level or quantity of the polypeptide than the level or quantity that is endogenously produced, e.g., in an unmodified cell. In embodiments, the cell or cell line identified, selected, or generated by the methods described herein produces a product, e.g., a recombinant polypeptide, useful in the treatment of a medical condition, disorder or disease. Examples of medical conditions, disorders or diseases include, but are not limited to, metabolic disease or disorders (e.g., metabolic enzyme deficiencies), endocrine disorders (e.g., hormone deficiencies), haemostasis, thrombosis, hematopoietic disorders, pulmonary disorders, gastro-intestinal disorders, immunoregulation (e.g., immunodeficiency), infertility, transplantation, cancer, and infectious diseases.

The recombinant polypeptide is an exogenous protein, e.g., a protein that is not naturally expressed by the cell. The recombinant polypeptide can be a therapeutic protein or a diagnostic protein, e.g., useful for drug screening. The therapeutic or diagnostic protein can be an antibody molecule, e.g., an antibody or an antibody fragment, a fusion protein, a hormone, a cytokine, a growth factor, an enzyme, a glycoprotein, a lipoprotein, a reporter protein, a therapeutic peptide, or a structural and/or functional fragment or hybrid of any of these. In embodiments, the product, e.g., exogenous therapeutic polypeptide, comprises multiple polypeptide chains, e.g., an antibody or antibody fragment that comprises a heavy and a light chain.

In one embodiment, the product, e.g., recombinant polypeptide is an antibody molecule. Products encompassed herein are diagnostic antibody molecules, e.g., a monoclonal antibody or antibody fragment thereof, useful for imaging techniques, and therapeutic antibody molecules suitable for administration to subjects, e.g., useful for treatment of diseases or disorders. An antibody molecule is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type II (Fn3)(see U.S. Pat. No. 6,703,199, which describes fibronectin polypeptide minibodies).

In embodiments, the recombinant or therapeutic polypeptide is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide, calcitonin, etanercept, hemoglobin glutamer 250 (bovine), drotrecogin alpha, collagenase, carperitide, recombinant human epidermal growth factor, DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (Hydron), deslorelin, histrelin, nafarelin, leuprolide (ATRIGEL), leuprolide (DUROS), goserelin, Eutropin, somatropin, mecasermin, enlfavirtide, Org-33408, insulin glargine, insulin glulisine, insulin (inhaled), insulin lispro, insulin deternir, insulin (RapidMist), mecasermin rinfabate, anakinra, celmoleukin, 99 mTc-apcitide, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex recombinant human luteinizing hormone, dornase alpha, trafermin, ziconotide, taltirelin, diboterminalfa, atosiban, becaplermin, eptifibatide, Zemaira, CTC-111, Shanvac-B, octreotide, lanreotide, ancestirn, agalsidase beta, agalsidase alpha, laronidase, prezatide copper acetate, rasburicase, ranibizumab, Actimmune, PEG-Intron, Tricomin, recombinant human parathyroid hormone (PTH) 1-84, epoetin delta, transgenic antithrombin II, Granditropin, Vitrase, recombinant insulin, interferon-alpha, GEM-21S, vapreotide, idursulfase, omnapatrilat, recombinant serum albumin, certolizumab pegol, glucarpidase, human recombinant C1 esterase inhibitor, lanoteplase, recombinant human growth hormone, enfuvirtide, VGV-1, interferon (alpha), lucinactant, aviptadil, icatibant, ecallantide, omiganan, Aurograb, pexigananacetate, ADI-PEG-20, LDI-200, degarelix, cintredelinbesudotox, Favid, MDX-1379, ISAtx-247, liraglutide, teriparatide, tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone, recombinant G-CSF, insulin, insulin (Technosphere), insulin (AERx), RGN-303, DiaPep277, interferon beta, interferon alpha-n3, belatacept, transdermal insulin patches, AMG-531, MBP-8298, Xerecept, opebacan, AIDSVAX, GV-1001, LymphoScan, ranpirnase, Lipoxysan, lusupultide, MP52, sipuleucel-T, CIP-37, Insegia, vitespen, human thrombin, thrombin, TransMID, alfimeprase, Puricase, terlipressin, EUR-1008M, recombinant FGF-I, BDM-E, rotigaptide, ETC-216, P-113, MBI-594AN, duramycin, SCV-07, OPI-45, Endostatin, Angiostatin, ABT-510, Bowman Birk Inhibitor, XMP-629, 99 mTc-Hynic-Annexin V, kahalalide F, CTCE-9908, teverelix, ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, SB-249553, Oncovax-CL, OncoVax-P, BLP-25, CerVax-16, MART-1, gp100, tyrosinase, nemifitide, rAAT, CGRP, pegsunercept, thymosin-beta4, plitidepsin, GTP-200, ramoplanin, GRASPA, OBI-1, AC-100, salmon calcitonin (eligen), examorelin, capromorelin, Cardeva, velafermin, 131I-TM-601, KK-220, T-10, ularitide, depelestat, hematide, Chrysalin, rNAPc2, recombinant Factor V111 (PEGylated liposomal), bFGF, PEGylated recombinant staphylokinase variant, V-10153, SonoLysis Prolyse, NeuroVax, CZEN-002, rGLP-1, BIM-51077, LY-548806, exenatide (controlled release, Medisorb), AVE-0010, GA-GCB, avorelin, ACM-9604, linaclotid eacetate, CETi-1, Hemospan, VAL, fast-acting insulin (injectable, Viadel), insulin (eligen), recombinant methionyl human leptin, pitrakinra, Multikine, RG-1068, MM-093, NBI-6024, AT-001, PI-0824, Org-39141, Cpn10, talactoferrin, rEV-131, rEV-131, recombinant human insulin, RPI-78M, oprelvekin, CYT-99007 CTLA4-Ig, DTY-001, valategrast, interferon alpha-n3, IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, ALTU-135, recombinant neuraminidase, Vacc-5q, Vacc-4x, Tat Toxoid, YSPSL, CHS-13340, FTH(1-34) (Novasome), Ostabolin-C, PTH analog, MBRI-93.02, MTB72F, MVA-Ag85A, FARA04, BA-210, recombinant plague FIV, AG-702, OxSODrol, rBetV1, Der-p1/Der-p2/Der-p7, PR1 peptide antigen, mutant ras vaccine, HPV-16 E7 lipopeptide vaccine, labyrinthin, WT1-peptide, IDD-5, CDX-110, Pentrys, Norelin, CytoFab, P-9808, VT-111, icrocaptide, telbermin, rupintrivir, reticulose, rGRF, HA, alpha-galactosidase A, ACE-011, ALTU-140, CGX-1160, angiotensin, D-4F, ETC-642, APP-018, rhMBL, SCV-07, DRF-7295, ABT-828, ErbB2-specific immunotoxin, DT3SSIL-3, TST-10088, PRO-1762, Combotox, cholecystokinin-B/gastrin-receptor binding peptides, 111In-hEGF, AE-37, trasnizumab-DM 1, Antagonist G, IL-12, PM-02734, IMP-321, rhIGF-BP3, BLX-883, CUV-1647, L-19 based ra, Re-188-P-2045, AMG-386, DC/1540/KLH, VX-001, AVE-9633, AC-9301, NY-ESO-1 (peptides), NA17.A2 peptides, CBP-501, recombinant human lactoferrin, FX-06, AP-214, WAP-8294A, ACP—HIP, SUN-11031, peptide YY [3-36], FGLL, atacicept, BR3-Fc, BN-003, BA-058, human parathyroid hormone 1-34, F-18-CCR1, AT-1100, JPD-003, PTH(7-34) (Novasome), duramycin, CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix, EP-51216, hGH, OGP-I, sifuvirtide, TV4710, ALG-889, Org-41259, rhCC10, F-991, thymopentin, r(m)CRP, hepatoselective insulin, subalin, L19-IL-2 fusion protein, elafin, NMK-150, ALTU-139, EN-122004, rhTPO, thrombopoietin receptor agonist, AL-108, AL-208, nerve growth factor antagonists, SLV-317, CGX-1007, INNO-105, teriparatide (eligen), GEM-OS1, AC-162352, PRX-302, LFn-p24 fusion, EP-1043, gpE1, gpE2, MF-59, hFIH(1-34), 768974, SYN-101, PGN-0052, aviscumnine, BIM-23190, multi-epitope tyrosinase peptide, enkastim, APC-8024, GI-5005, ACC-001, TFS-CD3, vascular-targeted TNF, desmopressin, onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEFPTIN™), pegrilgrastim (NEULASTA™), or any other suitable polypeptide including biosimilars and biobetters.

Other suitable polypeptides are those listed below and in Table 1 of US2016/0097074:

TABLE 1

| Protein Product | Referernce Listed Drug |
| --- | --- |
| interferon gamma-1b | Actimmune ® |
| alteplase: tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ® |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihernophilic factor | Biociate ™ |
| human growth hormone | BioTropin ™ |
| botulinum toxin type A | BOTOX ® |
| Alemtuzumab | Campath ® |
| acritumomab; technecium-99 labeled | CEA-Scan ® |
| alglucerase modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigitFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofoilitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophillic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| Interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ®FS |
| Insulin glargline | Lantus ® |
| granulocyte macrophage colony-stimulating factor | Leukine ®/Leukine ® Liquid |

TABLE 1-continued

| Protein Product | Referernce Listed Drug |
|---|---|
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesintide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension | Novolin L ® |
| insulin; isophane suspension | Novolin N ® |
| insulin, regular; | Novelin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomad-CD3 | Oethoclone OKT3 ® |
| high-molecular weight hyaluronan | Orthovisc ® |
| human chorionic gonadotropin | Ovidrel ® |
| live attenuated *Bacillus Calmette-Guerin* | Pacis ® |
| abatacept, fully human soluable fusion protein | Orencia ™ |
| muromomab-CD3 | Orthoclone OKT3 ® |
| high-molecular weight hyaluronan | Orthovisc ® |
| human chorionic genadetropin | Ovidrel ® |
| live attenuated *Bacillus Calmette-Guerin* | Pacis ® |
| peginterferon alfa-2a | Peegasys ® |
| pegylated version of interferon alfa-2b | PEG-Intron ™ |
| Abarelix (injectable suspension); gonado-tropin-releasing hormone antagonist | Plenaxis ™ |
| epoietin alfa | Procrit ® |
| Aidesleukin | Proroleukin, IL-2 ® |
| Somatrem | Protropira ® |
| dornase alfa | Pulmozyme ® |
| Efalizumab; selective, reversible T-cell blocker | RAPTIVA ™ |
| combination of ribavirin and alpha interferon | Rebetron ™ |
| Inteferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abci | ReoPro ™ |
| Retepase | Retavase ™ |
| Rituxima | Rituxan ™ |
| interferon alfa-2$^a$ | Roferon-A ® |
| Somtropin | Saizen ® |
| synthetic porcine secretin | SecreFlo ™ |
| Basiliximab | Simulect ® |
| Ecuilzumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natali_umab | TYSABRI ® |
| human immune globin intravenous 5% and 10% solutions | Venoglobulin-S ® |
| interferon alfa-n1, lymohoblastoid | Wellferon ® |
| drotreco in al | Xigris ™ |
| Omalizumab; recombinant DNA-derived humanized monoclonal antibody targeting immunoglobin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | |
| | Human chorionic gonadotropin | Gonal-F, Follisfim Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/ Coagulation Factors | Factor VIIa | NovoSeven |
| | Factor VIII | Bociate, Hefixate, Kogenate, Recombinate, ReFacto |
| | Factor IX | Benefix |
| | Antithrombin III (AT-III) | Thrombate III |
| | Protein C concentrate | Ceprotin |
| Cytokine/ Growth factor | Type I alpha-interferon | Infergen |
| | Interferon-αn3 (IFN-αn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin Kepivance Reganex Anril, Kineret |
| | Palifermin (keratinocyte growth factor; KGF) | |
| | Becaplemin (platelet derived growth factor; PDGF) | |
| | Anakinra (recombinant IL1 antagonist) | |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin Orencia |
| | Abatacept (CTLA Ab/Fc fusion) | Humira |
| | Adalimumab (TNF mAb) | Enbrel |
| | Etanercept (TNF receptor/Fc fusion) | Remicade Amevive Raptiva |
| | Infliximab (TNFα chimeric mAb) | Tysabri Soliris |
| | Alefacept (CD2 fusion protein) | Orthoclone, OKT3 |
| | Efalizumab (CD11a mAb) | |
| | Natalizumab (integrin α4 subunit mAb) | |
| | Eculizumab (C5mAb) Muromonab-CD3 | |

TABLE 2-continued

Exemplary Products

| Therapeutic Product type | Product | Trade Name |
|---|---|---|
| Other: Fusion proteins/ Protein vaccines/ Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) | Rhophylac |
| | immunoglobulin G Enfuvirtide | Fuzeon |
| | Spider silk, e.g., fibrion | QMONOS |

In embodiments, the protein is a multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3 HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |

TABLE 3-continued

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tithingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase VII | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| G5K2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

TABLE 4

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norelitropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone Antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |

TABLE 4-continued

| Protein Product | Reference Listed Drug |
| --- | --- |
| Efalizumab; selective, reversible T-cell blocker | RAPTIVA ™ |
| combination of ribavirin and alpha interferon | Rebetron ™ |
| interferon beta 1a | Rebif ® |
| antihemophilic factor | Recombina ®rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| iblitumomab tiuxetan | Zevalin ™ |
| Somatotropin | Zorbtive ™ (Serostim ®) |

In some embodiments, the recombinant or therapeutic polypeptide is an antigen expressed by a cancer cell. In some embodiments the recombinant or therapeutic polypeptide is a tumor-associated antigen or a tumor-specific antigen. In some embodiments, the recombinant or therapeutic polypeptide is selected from HER2, CD20, 9-O-acetyl-GD3, 3hCG, A33 antigen, CA19-9 marker, CA-125 marker, calreticulin, carboanhydrase IX (MN/CA IX), CCR5, CCR8, CD19, CD22, CD25, CD27, CD30, CD33, CD38, CD44v6, CD63, CD70, CC123, CD138, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (Ep-CAM), ErbB2, fetal acetylcholine receptor, fibroblast activation antigen (FAP), fucosyl GM1, GD2, GD3, GM2, ganglioside GD3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC1 variants (e.g. MUC1 A, B, C, D, X, Y, Z, REP, or SEC), MUC2, MUC3, MUC4, MUC5$_{AC}$, MUC5$_B$, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-alpha precursor, and combinations thereof.

In some embodiments, the recombinant or therapeutic polypeptide is an activating receptor and is selected from 2B4 (CD244), $\alpha_4\beta_1$ integrin, $\beta_2$ integrins, CD2, CD16, CD27, CD38, CD96, CD1OO, CD160, CD137, CEACAM1 (CD66), CRTAM, CSI (CD319), DNAM-1 (CD226), GITR (TNFRSF18), activating forms of KIR, NKG2C, NKG2D, NKG2E, one or more natural cytotoxicity receptors, NTB-A, PEN-5, and combinations thereof, optionally wherein the $\beta_2$ integrins comprise CD11a-CD 18, CD11 b-CD 18, or CD11c-CD 18, optionally wherein the activating forms of KIR comprise KIR2DS1, KIR2DS4, or KIR-S, and optionally wherein the natural cytotoxicity receptors comprise NKp30, NKp44, NKp46, or NKp80.

In some embodiments, the recombinant or therapeutic polypeptide is an inhibitory receptor and is selected from KIR, ILT2/LIR-1/CD85j, inhibitory forms of KIR, KLRG1, LAIR-1, NKG2A, NKR-P1A, Siglec-3, Siglec-7, Siglec-9, and combinations thereof, optionally wherein the inhibitory forms of KIR comprise KIR2DL1, KIR2DL2, KIR2DL3, KIR3DL1, KIR3DL2, or KIR-L.

In some embodiments, the recombinant or therapeutic polypeptide is an activating receptor and is selected from CD3, CD2 (LFA2, OX34), CD5, CD27 (TNFRSF7), CD28, CD30 (TNFRSF8), CD40L, CD84 (SLAMF5), CD137 (4-1BB), CD226, CD229 (Ly9, SLAMF3), CD244 (2B4, SLAMF4), CD319 (CRACC, BLAME), CD352 (Ly108, NTBA, SLAMF6), CRTAM (CD355), DR3 (TNFRSF25), GITR (CD357), HVEM (CD270), ICOS, LIGHT, LTβR (TNFRSF3), OX40 (CD134), NKG2D, SLAM (CD150, SLAMF1), TCRα, TCRβ, TCRδγ, TIM1 (HAVCR, KIM1), and combinations thereof.

In some embodiments, the recombinant or therapeutic polypeptide is an inhibitory receptor and is selected from PD-1 (CD279), 2B4 (CD244, SLAMF4), B71 (CD80), B7H1 (CD274, PD-L1), BTLA (CD272), CD160 (BY55, NK28), CD352 (Ly108, NTBA, SLAMF6), CD358 (DR6), CTLA-4 (CD152), LAG3, LAIR1, PD-1H (VISTA), TIGIT (VSIG9, VSTM3), TIM2 (TIMD2), TIM3 (HAVCR2, KIM3), and combinations thereof.

Other exemplary therapeutic or diagnostic proteins include, but are not limited to any protein described in Tables 1-10 of Leader et al., "Protein therapeutics: a summary and pharmacological classification", Nature Reviews Drug Discovery, 2008, 7:21-39 (incorporated herein by reference); or any conjugate, variant, analog, or functional fragment of the recombinant polypeptides described herein.

Other recombinant products include non-antibody scaffolds or alternative protein scaffolds, such as, but not limited to: DARPins, affibodies and adnectins. Such non-antibody scaffolds or alternative protein scaffolds can be engineered to recognize or bind to one or two, or more, e.g., 1, 2, 3, 4, or 5 or more, different targets or antigens.

Nucleic Aids

Also provided herein are nucleic acids, e.g., exogenous nucleic acids that encode the products, e.g., recombinant polypeptides, described herein. The nucleic acid sequences coding for the desired recombinant polypeptides can be obtained using recombinant methods known in the art, such as, for example by screening libraries from cells expressing the desired nucleic acid sequence, e.g., gene, by deriving the nucleic acid sequence from a vector known to include the same, or by isolating directly from cells and tissues containing the same, using standard techniques. Alternatively, the nucleic acid encoding the recombinant polypeptide can be produced synthetically, rather than cloned. Recombinant DNA techniques and technology are highly advanced and well established in the art. Accordingly, the ordinarily skilled artisan having the knowledge of the amino acid sequence of a recombinant polypeptide described herein can readily envision or generate the nucleic acid sequence that would encode the recombinant polypeptide.

The expression of the recombinant polypeptide is typically achieved by operably linking a nucleic acid encoding the recombinant polypeptide or portions thereof to a promoter, and incorporating the construct into an expression vector. The vectors can be suitable for replication and integration eukaryotes or prokaryotes. Typical cloning vectors contain other regulatory elements, such as transcription and translation terminators, initiation sequences, and promoters useful for regulation of the expression of the desired nucleic acid sequence.

In embodiments, the product, e.g., exogenous therapeutic polypeptide, comprises multiple polypeptide chains, e.g., an antibody or antibody fragment that comprises a heavy and a light chain. The nucleic acid sequences encoding an exogenous therapeutic polypeptide comprising multiple polypeptide chains may be disposed together (e.g., each polypeptide chain encoding sequence disposed on the same nucleic acid) or separately (e.g., each polypeptide chain encoding sequence disposed on different nucleic acids). The sequences encoding an exogenous therapeutic polypeptide comprising multiple polypeptide chains may be operably linked to a single control element, e.g., a first control element, or to distinct, separate control elements (e.g., each polypeptide chain encoding sequence is operably linked to its own first control element). In an embodiment where the sequences encoding an exogenous therapeutic polypeptide comprising multiple polypeptide chains are operably linked to distinct, separate control elements, one or more (e.g., one, two, three, four, five, six, or all) of the control elements may have a first level of activity under a first condition and a second level of activity under a second condition, and one or more (e.g., one, two, three, four, five, six, or more) of the control elements may be constitutive.

The nucleic acid sequence encoding the recombinant polypeptide can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In embodiments, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a control element which comprises a promoter element and optionally an enhancer element, convenient restriction endonuclease sites, and one or more selectable markers, (e.g., WO 01/96584; WO 01/29058; and U.S. Pat. No. 6,326,193). Vectors derived from viruses are suitable tools to achieve long-term gene transfer since they allow long-term, stable integration of a transgene and its propagation in daughter cells.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection, e.g., a selection marker or a reporter gene.

Vectors contemplated may comprise insertion sites suitable for inserting sequences encoding polypeptides, e.g., exogenous therapeutic polypeptides or repressor polypeptides.

Insertion sites may comprise restriction endonuclease sites.

Insertion sites may comprise recombination target sites, wherein the recombination target sites flank the sequences encoding polypeptides, e.g., exogenous therapeutic polypeptides or repressor polypeptides. In an embodiment, the recombinant target site is a lox site. In case the recombination target site is a lox site, the host cells need the presence and expression of the Cre recombinase in order to achieve a cross-over or recombination event.

In an embodiment, the recombination target site is a FRT site. In case the recombination target site is a FRT cite, the host cells need the presence and expression of FLP (FLP recombinase) in order to achieve a cross-over or recombination event.

Insertion sites may comprise landing pads, e.g., a portion of DNA, e.g., a selectable marker, flanked by short, approximately 25 bp unique sequences and/or restriction sites. Materials and methods contemplated include landing pad site site specific integration techniques known in the art, and, for example, in U.S. provisional application 62/460,420, hereby incorporated by reference in its entirety.

In some embodiments, the vector comprises at least one (e.g., one, two, or more) of the isolated nucleotide sequences of SEQ ID No. 17, 18, 19 or homologues thereof. In one embodiment, the vector comprises at least one sequence encoding a selectable marker, which itself is flanked at its 5' and 3' end by one recombination target site each, and wherein at least one of the nucleotide sequences of SEQ ID No. 17 or 18 or a homologous sequence thereof is located at the 3' end of the sequence encoding a selectable marker. In one embodiment, the vector comprises at least one sequence encoding a selectable marker, which itself is flanked at its 5' and 3' end by one recombination target site each, and wherein at least one nucleotide sequence as given in SEQ ID No. 19 or a homologous sequence thereof is located at the 5' end of the sequence encoding the selectable marker.

First Control Elements

In one embodiment, the vector comprising a nucleic acid sequence encoding a product, e.g., polypeptide, e.g., a recombinant or therapeutic polypeptide, further comprises a first control element, e.g., a first promoter element, responsible for the recruitment of polymerase to enable transcription initiation for expression of the polypeptide, e.g., the recombinant or therapeutic polypeptide. A first control element may comprise distal elements, e.g., elements that modulate expression of the polypeptide at a distance, e.g., a length of bases distant, from the sequence encoding the polypeptide, and proximal elements, e.g., elements that modulate expression of the polypeptide in part due to their position in close proximity to or within the sequence encoding the polypeptide. In some embodiments, the first control element, e.g., promoter element, operably linked to a sequence encoding a polypeptide, e.g., a recombinant or therapeutic polypeptide, is a constitutive control element. In some embodiments, the first control element, e.g., a promoter element, operably linked to a sequence encoding a polypeptide, e.g., a recombinant or therapeutic polypeptide, is a regulated control element, e.g. a control element regulated by an endogenous or exogenous polypeptide. In some embodiments, the first control element, e.g., the first promoter element, operably linked to a sequence encoding a polypeptide, e.g., a recombinant or therapeutic polypeptide, has a first level of activity under a first condition, e.g., a first stage of growth of the cell, e.g., exponential growth, and a second level of activity under a second condition, e.g., a second stage of growth of the cell, e.g., a phase having less than exponential growth, e.g., a growth-stable phase. In an embodiment, control elements suitable for the methods described herein are usually associated with enhancers to drive high amounts of transcription and hence deliver large copies of the target exogenous mRNA. In an embodiment, the first control element, e.g. first promoter element, comprises cytomegalovirus (CMV) major immediate early promoters (Xia, Bringmann et al. 2006) and the SV40 promoter (Chernajovsky, Mory et al. 1984), both derived from their namesake viruses or promoters derived therefrom. Several other less common viral promoters have been successfully employed to drive transcription upon inclusion in an expression vector including Rous Sarcoma virus long terminal repeat (RSV-LTR) and Moloney murine leukaemia virus (MoMLV) LTR (Papadakis, Nicklin et al. 2004). In another embodiment, specific endogenous mammalian promoters can be utilized to drive constitutive transcription of a gene of interest (Pontiller, Gross et al. 2008). The CHO specific Chinese Hamster elongation factor i-alpha (CHEF1α) promoter has provided a high yielding alternative to viral based sequences (Deer, Allison 2004). In some embodiments, the first control element, e.g., the first promoter element, used to drive transcription of a recombinant, e.g. therapeutic, polypeptide can include a thymidine kinase (TK) promoter, the actin promoter (e.g., the β-actin promoter), the glyceraldehyde 3-phosphate dehydrogenase (GAPDH) promoter, the cyclin T1 promoter, the CAG promoter, the RNA polymerase III U3 promoter, the cyclophillin promoter, the *Autographa californica* nuclear polyhedrosis virus (AcNPV) P10 promoter, the β-galactosyltransferase 5 (βGAL-T5) promoter, the Fer1 promoter, composite promoters such as CMV-EF1α promoters, and basal promoter and tripartite leader composite promoters. The aforementioned promoter elements are summarized in Table 5 and known in the art. It is contemplated that the invention is not limited to a specific promoter or promoters. The promoters and transcriptional control mechanisms described in WO2004/009823, WO2006/1111387, and WO02014044845 (hereby incorporated by reference in their entirety) are also contemplated in the context of the first and/or second control elements. In some embodiments, the first control element, e.g., promoter element, is an engineered promoter comprising synthetic (non-naturally occurring) sequences. For example, the first control element, e.g., promoter element, may comprise a promoter as described in Brown et al. Biotechnology and Bioengineering, Vol. 111, No. 8, August, 2014.

TABLE 5 cytomegalovirus (CMV) major immediate early promoters
SV40 promoter
Rous sarcoma virus long terminal repeat (RSV-LTR)
Moloney murine leukaemia. virus (MoMLV) LTR
CHO specific Chinese hamster elongation facto 1-alpha (CHEF1α) promoter
thymidine kinase (TK) promoter
actin promoter
glyceraldehyde 3-phosphate dehydrogenase (GAPDH) promoter
cyclin T1 promoter
RNA polymerase III U3 promoter
cyclophilin promoter
*Autographa californica* nuclear polyhedrosis virus (AcNPV) P10 promoter
β3-galactosyltransferase 5 (β3GAL-T5) promoter
CAG promoter Second Control Elements In one embodiment, the vector comprising a nucleic acid sequence encoding a polypeptide, e.g., a recombinant or repressor polypeptide, further comprises a second control element, e.g., a second promoter element, operably linked to the sequence encoding the polypeptide; the second control element is responsible for the recruitment of polymerase to enable transcription initiation for expression of the polypeptide, e.g., the recombinant or repressor polypeptide. A second control element may comprise distal elements, e.g., elements that modulate expression of the polypeptide at a distance, e.g., a length of bases distant or on a distinct and separate nucleic acid, from the sequence encoding the polypeptide, and proximal elements, e.g., elements that modulate expression of the polypeptide in part due to their position in close proximity to or within the sequence encoding the polypeptide. In an embodiment, the second control element, e.g., the second promoter element, operably linked to a sequence encoding a polypeptide, e.g., a recombinant or repressor polypeptide, is a constitutive control element. In some embodiments, the second control element, e.g., the second promoter element, operably linked to a sequence encoding a polypeptide, e.g., a recombinant or repressor polypeptide, is a regulated control element, e.g. a promoter regulated by an endogenous or exogenous polypeptide. In some embodiments, the second control element, e.g., the second promoter element, operably linked to a sequence encoding a polypeptide, e.g., a recombinant or repressor polypeptide, has a first level of activity under a first condition and a second level of activity under a second condition.

In some embodiments, the second control element, e.g., the second promoter element, operably linked to a sequence encoding a polypeptide, e.g., a recombinant or repressor polypeptide, has a first level of activity under a first condition and a second level of activity under a second condition wherein the second level of activity is modulated, e.g., higher or lower, relative to the first level of activity.

In some embodiments, the first condition and second condition pairs can be selected from a list comprising: a first, e.g., lower, level of stress and a second, e.g., higher level of stress; a first, e.g., lower, level of unfolded or misfolded polypeptide and a second, e.g., higher level of unfolded or misfolded polypeptide; a first, e.g., lower, level of unfolded or misfolded polypeptide in the cytosol and a second, e.g., higher, level of unfolded or misfolded polypeptide in the cytosol; a first, e.g., lower, level of unfolded or misfolded polypeptide in the endoplasmic reticulum (ER) and a second, e.g., higher level of unfolded or misfolded polypeptide in the ER; a first, e.g., lower, level of activation of the heat shock response (HSR) and a second, e.g., higher, level of activation of the HSR; a first, e.g., lower, level of activation of the unfolded protein response (UPR) and a second, e.g., higher, level of activation of the UPR; a first, e.g., higher, level of free ER chaperone, e.g., BiP, and a second, e.g., lower, level of free ER chaperone, e.g., BiP; a first, e.g., lower, temperature and a second, e.g., higher, temperature; a first, e.g., lower, level of oxidative stress and a second, e.g., higher, level of oxidative stress; a first, e.g., higher, level of ER $Ca^{2+}$ and a second, e.g., lower, level of ER $Ca^{2+}$; a first, e.g., more oxidative, level of ER oxidative state and a second, e.g., less oxidative, level of ER oxidative state; a first, e.g., higher, cellular energy level and a second, e.g., lower, cellular energy level; a first, e.g., higher, ATP level and a second, e.g., lower, ATP level; a first, e.g., higher, glucose level and a second, e.g., lower, glucose level; a first, e.g., lower, level of activated Hsf1 polypeptide and a second, e.g., higher, level of activated Hsf1 polypeptide; a first, e.g., lower, level of phosphorylated, trimeric Hsf1 polypeptide and a second, e.g., higher, level of phosphorylated, trimeric Hsf1 polypeptide; a first, e.g., lower, level of active, e.g., spliced, Xbp1 polypeptide and a second, e.g., higher, level of active, e.g., spliced, Xbp1 polypeptide; a first, e.g., lower, level of ATF4 polypeptide and a second, e.g., higher, level of ATF4 polypeptide; a first, e.g., lower, level of NRF2 polypeptide and a second, e.g., higher, level of NRF2 polypeptide; and a first, e.g., lower, level of ATF6 (e.g., ATF6α or ATF6β) polypeptide and a second, e.g., higher, level of ATF6 (e.g., ATF6α or ATF6β) polypeptide.

In some embodiments, the second control element has an $N^{th}$ level of activity under an $N^{th}$ condition, wherein N is 3, 4, 5, 6, 7, 8, 9, 10, or more and in the presence of the $N^{th}$ condition, the expression of the therapeutic polypeptide is modulated, e.g., decreased or increased, relative to the expression of the therapeutic polypeptide under previous conditions (e.g., condition 1, 2, 3, 4, 5, 6, 7, 8, 9, 10, etc.). For each pair of first and second conditions recited herein, a further $N^{th}$ (e.g., third, fourth, fifth, etc.) condition is contemplated, wherein the further $N^{th}$ condition is a further related condition. For example, wherein a first, e.g., lower, level of stress and a second, e.g., higher, level of stress are recited above, a further $N^{th}$ (e.g., third, fourth, fifth, etc.) (e.g., lower or higher) level of stress is also contemplated, with a corresponding $N^{th}$ level of activity.

In some embodiments, the first condition inhibits expression of the polypeptide, e.g., the recombinant or repressor polypeptide. In some embodiments, the second condition induces expression of the polypeptide, e.g., the recombinant or repressor polypeptide. In some embodiments, the second condition induces expression of the polypeptide, e.g., the repressor polypeptide, and the repressor polypeptide inhibits expression of another polypeptide, e.g. the exogenous therapeutic polypeptide. In some embodiments, under the second condition, expression of the exogenous therapeutic polypeptide, e.g., the transcriptional level, is reduced by at least 5%, 10%, 15%, 20%, 30%, 40%, 50%, 60%, 70%, 80%, 90%, or 100% compared to expression at the first condition.

In some embodiments, the second control element does not induce expression of the polypeptide, e.g., the recombinant or repressor polypeptide, under the first condition (e.g., the recombinant or repressor polypeptide is not appreciably expressed) and induces expression of the polypeptide, e.g., the recombinant or repressor polypeptide, under the second condition (e.g., the recombinant or repressor polypeptide is appreciably expressed). Appreciable expression may be detectable (e.g., by methods known in the art) accumulation of the polypeptide, e.g., recombinant or repressor polypeptide, or detectable accumulation of mRNA encoding the polypeptide, e.g., recombinant or repressor polypeptide.

In some embodiments, the second control element has a first level of activity under a first condition, a second level of activity under a second condition, and a third level of activity under a third condition. The first level of activity may result in a lack of appreciable expression of the polypeptide, e.g., the recombinant or repressor polypeptide. The second level of activity may result in appreciable expression of the polypeptide, e.g., the recombinant or repressor polypeptide. The third level of activity may result in modulation (e.g., an increase or decrease) in expression of the polypeptide, e.g., the recombinant or repressor polypeptide, relative to the second level of activity.

In some embodiments, the second control element has an $N^{th}$ level of activity under an $N^{th}$ condition, wherein N is 3, 4, 5, 6, 7, 8, 9, 10, or more and in the presence of the $N^{th}$ condition, the expression of the therapeutic polypeptide is modulated, e.g., decreased or increased, relative to the expression of the therapeutic polypeptide under previous conditions (e.g., condition 1, 2, 3, 4, 5, 6, 7, 8, 9, 10, etc.). In an embodiment, the $N^{th}$ level of activity of the second control element oscillates based on oscillations of the $N^{th}$ condition. For example, given a $1^{st}$ condition that is a first level of cellular stress and a $2^{nd}$ condition that is a second level of cellular stress, the second control element may have a $1^{st}$ level of activity and a $2^{nd}$ higher level of activity (e.g., this exemplary second control element has activity proportional to cellular stress). The $2^{nd}$ higher level of activity may increase expression of a polypeptide, e.g., a repressor polypeptide, which, upon accumulation, changes, e.g., decreases, expression of a recombinant or therapeutic polypeptide. The change, e.g., decrease, in expression of a recombinant or therapeutic polypeptide creates a $3^{rd}$ condition (e.g., a third level of cellular stress that is lower than the second level of cellular stress). The $3^{rd}$ condition has a corresponding $3^{rd}$ level of activity of the second control element; in the current example, that $3^{rd}$ level of activity may be decreased relative to the $2^{nd}$ level of activity, resulting in a decrease in the expression of the repressor polypeptide. The decrease in the repressor polypeptide expression under the $3^{rd}$ condition may lead to an increase in the expression of a recombinant or therapeutic polypeptide, creating a $4^{th}$ condition (e.g., a fourth level of cellular stress that is higher than the third level of cellular stress). Et cetera. In some embodiments, the oscillation of the activity of the second control element in relation to the oscillation of the condition may, over time, approach an equilibrium, e.g., a state where the difference in the activity of the second control element at an $N^{th}$ condition and an $N+1^{th}$ condition is negligible. In an embodiment, the second control element, e.g. second promoter element, comprises one or more (e.g., two, three, four, or more): heat shock elements (HSEs), HSEs which comprise one or more sequences corresponding to SEQ ID NOs: 8-11, cAMP response elements (CREs), CREs which comprise a sequence corresponding to SEQ ID NO: 12, antioxidant response elements (AREs), AREs which comprise a sequence corresponding to SEQ ID NO: 13, endoplasmic reticulum stress response elements (ERSEs), and ERSEs which comprise a sequence corresponding to SEQ ID NO: 14. In some embodiments, the second control element, e.g., second promoter element, may comprise one or more (e.g., two, three, four, or more) HSEs, CREs, AREs, or ERSEs that comprise sequences comprising zero, one, two, three, four, or five substitutions relative to a relevant consensus sequence known in the art. In some embodiments, the second control element, e.g., second promoter element, may comprise one or more (e.g., two, three, four, or more) HSEs, CREs, AREs, or ERSEs comprising a consensus sequence listed in Table 6. In some embodiments, the second control element, e.g., second promoter element, may comprise one or more (e.g., two, three, four, or more) HSEs, CREs, AREs, or ERSEs that comprise sequences comprising zero, one, two, three, four, or five substitutions relative to a corresponding consensus listed in Table 6 or known in the art. It is contemplated that the invention is not limited to a specific promoter or promoters.

TABLE 6

| Element | Exemplary consensus sequence(s) |
|---|---|
| Heat shock element (HRE) | SEQ ID NOs: 8-11 |
| cAMP response element (CRE) | SEQ ID NO: 12 |
| antioxidant response element (ARE) | SEQ ID NO: 13 |
| ER stress response element (ERSE) | SEQ ID NO: 14 |

In some embodiments, the second control element, e.g. second promoter element, comprises one or more (e.g., two, three, four, or more) elements modulated e.g., activated, by an element of the heat shock response, or the unfolded protein response (UPR). In some embodiments, the second control element, e.g. second promoter element, comprises one or more (e.g., two, three, four, or more) elements modulated e.g., activated, by accumulation of misfolded protein. In some embodiments, the second control element, e.g. second promoter element, comprises one or more (e.g., two, three, four, or more) Xbp1 responsive promoter elements. In some embodiments, the second control element, e.g. second promoter element, comprises one or more (e.g., two, three, four, or more) ATF6 responsive promoter elements. In some embodiments, the second control element, e.g. second promoter element, comprises one or more (e.g., two, three, four, or more) ATF4 responsive promoter elements. In some embodiments, the second control element, e.g. second promoter element, comprises one or more (e.g., two, three, four, or more) NRF2 responsive promoter elements. In some embodiments, the second control element, e.g. second promoter element, comprises one or more (e.g., two, three, four, or more) Hsf1 responsive promoter elements.

Third Control Elements

In some embodiments, cells, vectors, nucleic acids, and kits and methods comprising the same, of the present invention further comprise or use a nucleic acid sequence encoding one or more gRNAs (e.g., 1, 2, 3, 4, 5, 6, 7, 8, 9, 10 or more gRNAs) operably linked to a third control element, e.g., a third promoter element. The third control element is responsible for the recruitment of polymerase to enable transcription initiation for expression of the one or more gRNAs. In some embodiments, the third control element, e.g., third promoter element, is operably linked to a sequence encoding multiple gRNAs and the multiple gRNAs and/or sequence encoding the multiple gRNAs can be provided, produced, arranged, or processed as described in Gao, Y. and Y. Zhao (2014). J Integr Plant Biol 56(4): 343-349; Martick, M., et al. (2008). Nature 454(7206): 899-902; Xie, K., et al. (2015). Proc Natl Acad Sci USA 112(11): 3570-3575; Nissim, L., et al. (2014). Mol Cell 54(4): 698-710; and Port, F. and S. L. Bullock (2016). "Augmenting CRISPR applications in *Drosophila* with tRNA-flanked sgRNAs." Nat Meth [advance online publication], each of which is hereby incorporated by reference in its entirety. A third control element may comprise distal elements, e.g., elements that modulate expression of the polypeptide at a distance, e.g., a length of bases distant or on a distinct and separate nucleic acid, from the sequence encoding the one or more gRNAs, and proximal elements, e.g., elements that modulate expression of the one or more gRNAs in part due to their position in close proximity to or within the sequence encoding the one or more gRNAs. In an embodiment, the third control element, e.g., the third promoter element, operably linked to a sequence encoding one or more gRNAs, is a constitutive control element. In some embodiments, the third control element, e.g., the third promoter element, operably linked to a sequence encoding one or more gRNAs, is a regulated control element, e.g. a promoter regulated by an endogenous or exogenous polypeptide. In some embodiments, the third control element, e.g., the third promoter element, operably linked to a sequence encoding one or more gRNAs, has a first level of activity under a first condition and a second level of activity under a second condition.

In some embodiments, the third control element, e.g., the third promoter element, operably linked to a sequence encoding one or more gRNAs, is a copy of a first control element described herein. In some embodiments, the third control element, e.g., the third promoter element, operably linked to a sequence encoding one or more gRNAs, is a copy of a second control element described herein.

In some embodiments, the third control element, e.g., third promoter element, is an engineered promoter comprising synthetic (non-naturally occurring) sequences. For example, the third control element, e.g., third promoter element, may comprise a promoter as described in Brown et al. Biotechnology and Bioengineering, Vol. 111, No. 8, August, 2014.

In addition to promoters, the vectors described herein further comprise an enhancer region as described above; a specific nucleotide motif region, proximal to the core promoter, which can recruit transcription factors to upregulate the rate of transcription (Riethoven 2010). Similar to promoter sequences, these regions are often derived from viruses and are encompassed within the promoter sequence such as hCMV and SV40 enhancer sequences, or may be additionally included such as adenovirus derived sequences (Gaillet, Gilbert et al. 2007).

Other Nucleic Acid Features

In one embodiment, the vector comprising a nucleic acid sequence encoding a product, e.g., a polypeptide, e.g, a recombinant polypeptide, described herein further comprises a nucleic acid sequence that encodes a selection marker. In one embodiment, the selectable marker comprises glutamine synthetase (GS); dihydrofolate reductase (DHFR) e.g., an enzyme which confers resistance to methotrexate (MTX); or an antibiotic marker, e.g., an enzyme that confers resistance to an antibiotic such as: hygromycin, neomycin (G418), zeocin, puromycin, or blasticidin. In another embodiment, the selection marker comprises or is compatible with the Selexis selection system (e.g., SUREtechnology Platform™ and Selexis Genetic Elements™, commercially available from Selexis SA) or the Catalant selection system.

In one embodiment, the vector comprising a nucleic acid sequence encoding a recombinant product described herein comprises a selection marker that is useful in identifying a cell or cells comprise the nucleic acid encoding a recombinant product described herein. In another embodiment, the selection marker is useful in identifying a cell or cells that comprise the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

Suitable vectors for use are commercially available, and include vectors associated with the GS Expression System™, GS Xceed™ Gene Expression System, or Potelligent® CHOK1SV technology available from Lonza Biologics, PLC, e.g., vectors as described in Fan et al., *Pharm. Bioprocess.* (2013); 1(5):487-502, which is incorporated herein by reference in its entirety. GS expression vectors comprise the GS gene, or a functional fragment thereof (e.g., a GS minigene), and one or more, e.g., 1, 2, or 3, or more, highly efficient transcription cassettes for expression of the gene of interest, e.g., a nucleic acid encoding a recombinant polypeptide described herein. The minigene contains a single intron of the GS gene and about 1 kb of 3' flanking DNA, and is transcribed from the SV40 late promoter. In one embodiment, a GS vector comprises a GS gene operably linked to a SV40L promoter and one or two polyA signals. In another embodiment, a GS vector comprises a GS gene operably linked to a SV40E promoter, and SV40 intron splicing and polyadenylation signals. In such embodiments, the transcription cassette, e.g., for expression of the gene of interest or recombinant polypeptide described herein, includes the hCMV-MIE promoter and 5' untranslated sequences from the hCMV-MIE gene including the first intron. Other vectors can be constructed based on GS expression vectors, e.g., wherein other selection markers are substituted for the GS gene in the expression vectors described herein.

Vectors suitable for use in the methods described herein include, but are not limited to, other commercially available vectors, such as, pcDNA3.1/Zeo, pcDNA3.1/CAT, pcDNA3.3TOPO (Thermo Fisher, previously Invitrogen); pTarget, HaloTag (Promega); pUC57 (GenScript); pFLAG-CMV (Sigma-Aldrich); pCMV6 (Origene); pEE12 or pEE14 (Lonza Biologics), or pBK-CMV/pCMV-3Tag-7/pCMV-Tag2B (Stratagene).

Cells

Recombinant proteins or polypeptides, e.g., therapeutic polypeptides, can be produced by recombinant DNA technology, expressed by host cells, and can be either purified from the host cell (e.g., a CHO cell) or secreted into the fluid, e.g., cell medium, in which the host cell is cultured and purified from the fluid. Cells capable of producing recombinant proteins or polypeptides in high yields and of appropriate quality are highly desired in the field. The cells, methods for making cells, methods of making a recombinant, e.g., therapeutic, polypeptide, and kits relating thereto are useful for making cells with improved viability, high productivity cells, to obtain high yields of recombinant, e.g., therapeutic, polypeptide product, or to provide higher quality preparations of recombinant polypeptide product, e.g., preparations of recombinant polypeptide product that comprise a higher amount of correctly folded protein, lower amounts of aggregated protein, desired glycosylation patterns, or desired levels of glycosylation. The cells, methods for making cells, methods of making a recombinant, e.g., therapeutic, polypeptide, and kits relating thereto are particularly useful for production of recombinant, e.g., therapeutic, polypeptides, where there is a demand for efficient cell line development, large quantities of the recombinant therapeutic polypeptide product, and high grade of quality for therapeutic use in patients.

Cells and Cell Culture

In one aspect, the present disclosure relates to methods for evaluating, classifying, identifying, selecting, or making a cell or cell line that produces a product, e.g., a recombinant or therapeutic polypeptide as described herein. In another aspect, the present disclosure relates to methods and compositions for evaluating, classifying, identifying, selecting, or making a cell or cell line with improved, e.g., increased, productivity and product quality.

In embodiments, the cell is a mammalian cell. In other embodiments, the cell is a cell other than a mammalian cell. In an embodiment, the cell is from mouse, rat, Chinese hamster, Syrian hamster, monkey, ape, dog, horse, ferret, or cat. In embodiments, the cell is a mammalian cell, e.g., a human cell or a rodent cell, e.g., a hamster cell, a mouse cell, or a rat cell. In another embodiment, the cell is from a duck, parrot, fish, insect, plant, fungus, or yeast. In one embodiment, the cell is an Archaebacteria. In an embodiment, the cell is a species of Actinobacteria, e.g., *Mycobcterium tuberculosis*).

In one embodiment, the cell is a Chinese hamster ovary (CHO) cell. In one embodiment, the cell is a CHO-K1 cell, a CHOK1SV cell, a DG44 CHO cell, a DUXB11 CHO cell, a CHO-S, a CHO GS knock-out cell, a CHOK1SV FUT8 knock-out cell, a CHOZN, or a CHO-derived cell. The CHO GS knock-out cell (e.g., GSKO cell) is, for example, a CHO-K1SV GS knockout cell (Lonza Biologics, Inc.). The CHO FUT8 knockout cell is, for example, the Potelligent® CHOK1SV FUT8 knock-out (Lonza Biologics, PLC.).

In one embodiment, the cell is a site-specific integration (SSI) host cell. In an embodiment, SSI host cell comprises an endogenous Fer1LA gene, wherein an exogenous nucleotide sequence is integrated in said Fer1LA gene. In some embodiments, the exogenous nucleotide sequence comprises at least one gene coding sequence of interest, e.g., a gene encoding a therapeutic, repressor, or selective marker polypeptide. In some embodiments, the exogenous nucleotide sequence comprises at least two recombination target sites. In some embodiments, the recombination target sites flank at least one gene coding sequence of interest. In other embodiments, the recombination target sites are adjacent to, and do not flank, at least one gene coding sequence of interest. In some embodiments, the gene coding sequence of interest comprises at least one selection marker gene.

In an embodiment, the SSI host cell is characterized by the presence of exogenous nucleotide sequences, namely at least one sequence encoding a recombinant, e.g., therapeutic or repressor polypeptide, which itself is flanked at its 5' and 3' end by one recombination target site each, and wherein at least one of the nucleotide sequences of SEQ ID No. 17 or 18 or a homologous sequence thereof is located at the 3' end of the exogenous nucleotide sequences integrated into the genome of the host cell. In an embodiment, the SSI host cell is characterized by the presence of exogenous nucleotide sequences, namely at least one sequence encoding a recombinant, e.g., therapeutic or repressor, polypeptide, which itself is flanked at its 5' and 3' end by one recombination target site each, and wherein at least one nucleotide sequence as given in SEQ ID No. 19 or a homologous sequence thereof is located at the 5' end of the exogenous nucleotide sequences integrated into the genome of the host cell.

In one embodiment, the cell is a site-specific integration (SSI) host cell. In an embodiment, the SSI host cell is characterized by the presence of exogenous nucleotide sequences, namely at least one sequence encoding a selectable marker, which itself is flanked at its 5' and 3' end by one recombination target site each, and wherein at least one of the nucleotide sequences of SEQ ID No. 17 or 18 or a homologous sequence thereof is located at the 3' end of the exogenous nucleotide sequences integrated into the genome of the host cell. In an embodiment, the SSI host cell is characterized by the presence of exogenous nucleotide sequences, namely at least one sequence encoding a selectable marker, which itself is flanked at its 5' and 3' end by one recombination target site each, and wherein at least one nucleotide sequence as given in SEQ ID No. 19 or a homologous sequence thereof is located at the 5' end of the exogenous nucleotide sequences integrated into the genome of the host cell.

In another embodiment, the cell is a HeLa, HEK293, HT1080, H9, HepG2, MCF7, Jurkat, NIH3T3, PC12, PER.C6, BHK (baby hamster kidney cell), VERO, SP2/0, NS0, YB2/0, Y0, EB66, C127, L cell, COS, e.g., COS1 and COS7, QC1-3, CHOK1, CHOK1SV, Potelligent™ (CHOK1SV FUT8-KO), CHO GS knockout, Xceed™ (CHOK1SV GS-KO), CHOS, CHO DG44, CHO DXB11, and CHOZN, or any cells derived therefrom.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic Küpffer cells, human hepatic stellate cells, dog hepatocytes (including single and pooled Beagle hepatocytes), mouse hepatocytes (including CD-1 and C57BI/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* sp. (such as *A. niger, A. fumigatus, A. orzyae, A. nidula*), *Acremonium* sp. (such as *A. thermophilium*), *Chaetomium* sp. (such as *C. thermophilum*), *Chrysosporium* sp. (such as *C. thermophile*), *Cordyceps* sp. (such as *C. militaris*), *Corynascus* sp., *Ctenomyces* sp., *Fusarium* sp. (such as *F. oxysporum*), *Glomerella* sp. (such as *G. graminicola*), *Hypocrea* sp. (such as *H. jecorina*), *Magnaporthe* sp. (such as *M. orzyae*), *Myceliophthora* sp. (such as *M. thermophile*), *Nectria* sp. (such as *N. heamatococca*), *Neurospora* sp. (such as *N. crassa*), *Penicillium* sp., *Sporotrichum* sp. (such as *S. thermophile*), *Thielavia* sp. (such as *T. terrestris, T. heterothallica*), *Trichoderma* sp. (such as *T. reesei*), or *Verticillium* sp. (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora* sp., *Bacillariophyceae* sp., *Dunaliella* sp., *Chlorella* sp., *Chlamydomonas* sp., *Cyanophyta* sp. (cyanobacteria), *Nannochloropsis* sp., *Spirulina* sp., or *Ochromonas* sp.), or a plant cell (e.g., cells from monocotyledonous plants (e.g., maize, rice, wheat, or *Setaria* sp.), or from a dicotyledonous plants (e.g., cassava, potato, soybean, tomato, tobacco, alfalfa, *Physcomitrella patens* or *Arabidopsis* sp.).

In one embodiment, the cell is a bacterial or prokaryotic cell.

In embodiments, the prokaryotic cell is a Gram-positive cells such as *Bacillus* sp., *Streptomyces* sp., *Streptococcus* sp., *Staphylococcus* sp., or *Lactobacillus* sp. *Bacillus* sp. that can be used is, e.g. the *B. subtilis, B. amyloliquefaciens, B. licheniformis, B. natto,* or *B. megaterium*. In embodiments, the cell is *B. subtilis*, such as *B. subtilis* 3NA and *B. subtilis* 168. *Bacillus* sp. is obtainable from, e.g., the Bacillus Genetic Stock Center, Biological Sciences 556, 484 West 12$^{th}$ Avenue, Columbus OH 43210-1214.

In one embodiment, the prokaryotic cell is a Gram-negative cell, such as *Salmonella* sp. or *Escherichia coli*, such as e.g., TG1, TG2, W3110, DH1, DHB4, DH5a, HMS 174, HMS 174 (DE3), NM533, C600, HB101, JM109, MC4100, XL1-Blue and Origami, as well as those derived from *E. coli* B-strains, such as for example BL-21 or BL21 (DE3), or BL21 (DE3) pLysS, all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In an embodiment, the cell is any one of the cells described herein that comprises an exogenous nucleic acid encoding a recombinant polypeptide, e.g., expresses a recombinant polypeptide, e.g., a recombinant polypeptide selected from Tables 1-4.

In an embodiment, the cell culture is carried out as a batch culture, fed-batch culture, draw and fill culture, or a continuous culture. In an embodiment, the cell culture is a suspension culture. In one embodiment, the cell or cell culture is placed in vivo for expression of the recombinant polypeptide, e.g., placed in a model organism or a human subject.

In one embodiment, the culture media is free of serum. Serum-free, protein-free, and chemically-defined animal component-free (CDACF) media are commercially available, e.g., Lonza Biologics.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4$^{th}$ edition, Wiley-Liss/N.Y., 2000.

Other suitable cultivation methods are known to the skilled artisan and may depend upon the recombinant polypeptide product and the host cell utilized. It is within the skill of an ordinarily skilled artisan to determine or optimize conditions suitable for the expression and production of the recombinant or therapeutic polypeptide to be expressed by the cell.

In one aspect, the cell or cell line comprises an exogenous nucleic acid that encodes a product, e.g., a recombinant or therapeutic polypeptide. In an embodiment, the cell or cell line expresses the product, e.g., a therapeutic or diagnostic product. Methods for genetically modifying or engineering a cell to express a desired polypeptide or protein are well known in the art, and include, for example, transfection, transduction (e.g., viral transduction), or electroporation.

Physical methods for introducing a nucleic acid, e.g., an exogenous nucleic acid or vector described herein, into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Chemical means for introducing a nucleic acid, e.g., an exogenous nucleic acid or vector described herein, into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In embodiments, the integration of the exogenous nucleic acid into a nucleic acid of the host cell, e.g., the genome or chromosomal nucleic acid of the host cell is desired. Methods for determining whether integration of an exogenous nucleic acid into the genome of the host cell has occurred can include a GS/MSX selection method. The GS/MSX selection method uses complementation of a glutamine auxotrophy by a recombinant GS gene to select for high-level expression of proteins from cells. Briefly, the GS/MSX selection method comprises inclusion of a nucleic acid encoding glutamine synthetase on the vector comprising the exogenous nucleic acid encoding the recombinant polypeptide product. Administration of methionine sulfoximine (MSX) selects cells that have stably integrated into the genome the exogenous nucleic acid encoding both the recombinant, therapeutic, or repressor polypeptide and GS. As GS can be endogenously expressed by some host cells, e.g., CHO cells, the concentration and duration of selection with MSX can be optimized to identify high producing cells with stable integration of the exogenous nucleic acid encoding the recombinant, therapeutic, or repressor polypeptide product into the host genome. The GS selection and systems thereof is further described in Fan et al., *Pharm. Bioprocess.* (2013); 1(5):487-502, which is incorporated herein by reference in its entirety.

Other methods for identifying and selecting cells that have stably integrated the exogenous nucleic acid into the host cell genome can include, but are not limited to, inclusion of a reporter gene on the exogenous nucleic acid and assessment of the presence of the reporter gene in the cell, and PCR analysis and detection of the exogenous nucleic acid.

In one embodiment, the cells selected, identified, or generated using the methods described herein, (e.g., cells comprising a first control element, e.g., a first promoter element, operably linked to a sequence encoding an exogenous therapeutic polypeptide; and a second control element, e.g., second promoter element, operably linked to a sequence encoding a repressor polypeptide; wherein, the second control element has a first level of activity under a first condition and a second level of activity under a second condition, and in the presence of the second condition, the expression of the therapeutic polypeptide is modulated, e.g., decreased) are capable of producing higher or more consistent yields of protein product than cells that are selected using only a selection method for the stable expression, e.g., integration, of exogenous nucleic acid encoding the recombinant or therapeutic polypeptide. In an embodiment, the cells selected, identified, or generated using the methods described herein produce 2-fold, 3-fold, 4-fold, 5-fold, 6-fold, 7-fold, 8-fold, 9-fold, or 10-fold or more of the product, e.g., recombinant or therapeutic polypeptide, as compared to cells that were only selected, identified, or generated for stable expression, e.g., integration, of the exogenous nucleic acid encoding the recombinant or therapeutic polypeptide. In an embodiment, the cells selected, identified, or generated using the methods described herein produce the product, e.g., recombinant or therapeutic polypeptide, for a period of time or number of cell passages that is 2-fold, 3-fold, 4-fold, 5-fold, 6-fold, 7-fold, 8-fold, 9-fold, 10-fold or more increased as compared to cells that were only selected, identified, or generated for stable expression, e.g., integration, of the exogenous nucleic acid encoding the recombinant or therapeutic polypeptide. In an embodiment, the cells selected, identified, or generated using the methods described herein produce 10, 20, 30, 40, 50, 60, 70, 80, 90, 100, 150, 200, or 300% more correctly folded product, e.g., recombinant or therapeutic polypeptide, as compared to cells that were only selected, identified, or generated for stable expression, e.g., integration, of the exogenous nucleic acid encoding the recombinant or therapeutic polypeptide. In an embodiment, the cells selected, identified, or generated using the methods described herein produce 10, 20, 30, 40, 50, 60, 70, 80, 90, 100% less aggregated protein or product, e.g., recombinant or therapeutic polypeptide, as compared to cells that were only selected, identified, or generated for stable expression, e.g., integration, of the exogenous nucleic acid encoding the recombinant or therapeutic polypeptide. In an embodiment, the cells selected, identified, or generated using the methods described herein produce 10, 20, 30, 40, 50, 60, 70, 80, 90, 100, 150, 200, or 300% more glycosylated product, e.g., recombinant or therapeutic polypeptide, as compared to cells that were only selected, identified, or generated for stable expression, e.g., integration, of the exogenous nucleic acid encoding the recombinant or therapeutic polypeptide. In an embodiment, populations of cells selected, identified, or generated using the methods described herein and used to produce product are 10, 20, 30, 40, 50, 60, 70, 80, 90, 100, 150, 200, or 300% more viable as compared to cells that were only selected, identified, or generated for stable expression, e.g., integration, of the exogenous nucleic acid encoding the recombinant or therapeutic polypeptide and were used to produce product.

Evaluating, Classifying, Selecting, or Identifying a Cell

In one aspect, the disclosure features methods for evaluating a cell, e.g., a candidate cell, for capability of product production, e.g., recombinant or therapeutic polypeptide production. The results of such evaluation can provide information useful for selection or identification of cells for generating a cell or cell line that is a high production cell or cell line. In another embodiment, the responsive to the evaluation described herein, the cell or cell line can be classified, e.g., as a cell or cell line that has the capability of high production.

A high production cell or cell line is capable of producing higher yields of a recombinant or therapeutic polypeptide product than compared to a reference cell or a cell that has not been selected or generated by the methods described herein. In an embodiment, a high production cell line is capable of producing 100 mg/L, 200 mg/L, 300 mg/L, 400 mg/L, 500 mg/L, 600 mg/L, 700 mg/L, 800 mg/L, 900 m g/L, 1 g/L, 2 g/L, 3 g/L, 4 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, or 100 g/L or more of a product, e.g., a recombinant polypeptide product. In an embodiment, a high production cell line produces 100 mg/L, 200 mg/L, 300 mg/L, 400 mg/L, 500 mg/L, 600 m g/L, 700 mg/L, 800 m g/L, 900 mg/L, 1 g/L, 2 g/L, 3 g/L, 4 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, or 100 g/L or more of a product, e.g., a recombinant or therapeutic polypeptide product. The quantity of product produced may vary depending on the cell type, e.g., species, and the recombinant or therapeutic polypeptide to be expressed. By way of example, a high production cell is capable of producing at least 1 g/L, 2 g/L, 5 g/L, 10 g/L, 15 g/L, 20 g/L, or 25 g/L or more of a recombinant or therapeutic polypeptide, e.g., as described herein.

In embodiments where the product is difficult to express, the high production cell may produce lower concentrations of products, e.g., less than 0.1 g/L, 0.5 g/L, or 1 g/L, however, the productivity is higher or increased than that observed for cells that do not comprise a nucleic acid comprising a control element operably linked to a sequence encoding a repressor polypeptide. For example, the level, amount, or quantity of the product produced by the identified or selected cell is increased, e.g., by 1-fold, 2-fold, 3-fold, 4-fold, 5-fold, 6-fold, 7-fold, 8-fold, 9-fold, 10-fold, 20-fold, 50-fold, or 100-fold or more, as compared to the level, amount, or quantity produced by a cell that does not comprise a nucleic acid comprising a control element operably linked to a sequence encoding a repressor polypeptide.

The methods described herein for evaluating a cell include evaluating the effect of a repressor polypeptide on one or more parameters related to cell function. Parameters related to cell function include, but are not limited to, cell survival, culture viability, the ability to proliferate, the ability to produce a product, and protein degradation. In embodiments, the value of the effect of expression of a repressor polypeptide on one or more parameters related to cell function is compared to a reference value, for determining the effect of the repressor polypeptide on the parameter related to cell function, e.g., for determining whether the cell comprising a nucleic acid comprising a control element operably linked to a sequence encoding a repressor polypeptide results in an increase or decrease in one of the parameters related to cell function. In one embodiment, a cell can be selected or identified for development as a cell production line in response to the determination of an increases or decrease in one or more of the parameters related to cell function. In one embodiment, a cell can be identified as a high production cell, e.g., a cell capable of producing higher yields of a product, in response to the determination of an increase or decrease in one or more of the parameters related to cell function.

In any of the embodiments described herein, the reference value can be the value of the effect of the repressor polypeptide on a parameter related to cell function of a reference cell, e.g., a cell with a predetermined productivity. Alternatively, or in addition in any of the embodiments described herein, the reference value can be the value of the parameter related to cell function of the same cell being tested, where the cell does not comprise a nucleic acid comprising a control element operably linked to a sequence encoding a repressor polypeptide, e.g., the value of the parameter was measured before contacting the cell with the nucleic acid comprising a control element operably linked to a sequence encoding a repressor polypeptide, or a separate aliquot of the cell that has not been contacted with the nucleic acid comprising a control element operably linked to a sequence encoding a repressor polypeptide.

In one embodiment, cell survival can be measured by determining or quantifying cell viability, e.g., the number or amount of cells that survive expression of the recombinant or therapeutic polypeptide in cells also comprising a control element operably linked to a sequence encoding a repressor polypeptide. An increase in cell survival comprises a 1%, 2%, 5%, 10%, 20%, 30%, 40%, 50%, 60%, 70%, 80%, 90%, one-fold, two-fold, three-fold, four-fold, or five-fold or more increase in the number of cells, e.g., intact or live cells, remaining after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide. Alternatively, an increase in cell survival comprises a 1%, 2%, 5%, 10%, 20%, 30%, 40%, 50%, 60%, 70%, 80%, 90%, or more decrease in the number of apoptotic cells after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide. Methods for detecting cell survival or apoptosis are known in the art, e.g., Annexin V assays, the time integral of viable cell concentration (IVC), maximum viable cell concentration, and cell specific productivity rate.

In one embodiment, culture viability can be measured by determining or quantifying the number or amount of live cells, e.g., live cells in a culture or population of cell, or cells that have a characteristic related to viability, e.g., proliferation markers, intact DNA, or do not display apoptotic markers. An increase in culture viability comprises a 1%, 2%, 5%, 10%, 20%, 30%, 40%, 50%, 60%, 70%, 80%, 90%, one-fold, two-fold, three-fold, four-fold, or five-fold or more increase in the number of cells, e.g., intact or live cells, remaining after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide. Methods for determining culture viability are known in the art. Other methods for assessing culture viability include, but are not limited to, trypan blue exclusion methods followed by counting using a haemocytometer or Vi-CELL (Beckman-Coulter). Other methods for assessing culture viability can comprise determining viable biomass, and includes using radiofrequency impedance or capacitance (e.g., Carvell and Dowd, 2006, Cytotechnology, 50:35-48), or using Raman spectroscopy (e.g., Moretto et al., 2011, American Pharmaceutical Review, Vol. 14).

In one embodiment, the ability of a cell to proliferate can be measured by quantifying or counting the number of cells, cell doublings, or growth rate of the cells. Alternatively, proliferating cells can be identified by analysis of the genomic content of the cells (e.g., replicating DNA), e.g., by flow cytometry analysis, or presence of proliferation markers, e.g., Ki67, phosphorylated cyclin-CDK complexes involved in cell cycle. An increase in the ability to proliferate comprises a 1%, 2%, 5%, 10%, 20%, 30%, 40%, 50%, 60%, 70%, 80%, 90%, one-fold, two-fold, three-fold, four-fold, or five-fold or more increase in the number of cells, or number of cells expressing a proliferation marker, after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide. Alternatively, an increase in the ability to proliferate comprises a 1%, 2%, 5%, 10%, 20%, 30%, 40%, 50%, 60%, 70%, 80%, 90%, one-fold, two-fold, three-fold, four-fold, or five-fold or more increase in the doubling or growth rate of the cells after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide. Methods for determining culture viability are known in the art.

The methods provided herein are useful for identifying, selecting, or making a cell or cell line that has improved capacity for producing a recombinant or therapeutic polypeptide, e.g., a product. In one embodiment, the methods provided herein are also useful for identifying, selecting, or making a cell or cell line that produces an improved quality of the recombinant or therapeutic polypeptide.

In one embodiment, the ability of the cell to produce a product can be measured by determining or quantifying the amount or concentration of product that is produced. An increase in the ability to produce a product comprises a 1%, 2%, 5%, 10%, 20%, 30%, 40%, 50%, 60%, 70%, 80%, 90%, one-fold, two-fold, three-fold, four-fold, or five-fold or more increase in protein production after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide.

In one embodiment, the quality of the product, e.g., expressed recombinant or therapeutic polypeptide, can be measured by determining or quantifying the amount or concentration of properly folded product, functional product, or non-aggregated product. An increase in the quality of the product produced by the cell comprises a 1%, 2%, 5%, 10%, 20%, 30%, 40%, 50%, 60%, 70%, 80%, 90%, one-fold, two-fold, three-fold, four-fold, or five-fold or more increase in the amount or concentration of properly folded product, functional product, or non-aggregated product, e.g., expressed recombinant or therapeutic polypeptide, after expression of the recombinant or therapeutic polypeptide in cells also comprising a control element operably linked to a sequence encoding a repressor polypeptide as compared to after expression of the recombinant or therapeutic peptide in cells not comprising a control element operably linked to a sequence encoding a repressor polypeptide.

In one embodiment, the quality of the product, e.g., expressed recombinant or therapeutic polypeptide, can be measured by determining or quantifying the amount or concentration of product with the correct glycosylation profile, macro-heterogeneity (i.e. site occupancy), and the consistency of glycosylation. An increase in the quality of the product produced by the cell comprises a 1%, 2%, 5%, 10%, 20%, 30%, 40%, 50%, 60%, 70%, 80%, 90%, one-fold, two-fold, three-fold, four-fold, or five-fold or more increase in the amount or concentration of product with the correct glycosylation profile, with increased site occupancy, or with increased consistency of glycosylation after expression of the recombinant or therapeutic polypeptide in cells also comprising a control element operably linked to a sequence encoding a repressor polypeptide as compared to after expression of the recombinant or therapeutic polypeptide in cells not comprising a control element operably linked to a sequence encoding a repressor polypeptide.

Methods of measuring increased protein production are well-known to those skilled in the art. For example, an increase in recombinant or therapeutic protein production might be determined at small-scale by measuring the titer in tissue culture medium by ELISA (Smales et al. 2004 Biotechnology Bioengineering 88:474-488). It can also be determined quantitatively by the ForteBio Octet, for example for high throughput determination of recombinant monoclonal antibody (mAb) concentration in medium (Mason et al. 2012 Biotechnology Progress 28:846-855) or at a larger-scale by protein A HPLC (Stansfield et al. 2007 Biotechnology Bioengineering 97:410-424). Other methods for determining production of a product, e.g., a recombinant or therapeutic polypeptide described herein, can refer to specific production rate (qP) of the product, in particular the recombinant or therapeutic polypeptide in the cell and/or to a time integral of viable cell concentration (IVC). Recombinant or therapeutic polypeptide production or productivity, being defined as concentration of the polypeptide in the culture medium, is a function of these two parameters (qP and IVC), calculated according to Porter et al. (Porter et al. 2010 Biotechnology Progress 26:1446-1455).

Methods for measuring improved quality of product produced by the cell lines generated as described herein are known in the art. In one embodiment, methods for determining the fidelity of the primary sequence of the expressed recombinant or therapeutic polypeptide product are known in the art, e.g., mass spectrometry, HPLC, SDS-PAGE, peptide mapping, and IEF. An increase in the amount or concentration of properly folded product, e.g., expressed recombinant or therapeutic polypeptide, can be determined by circular dichroism or assessing the intrinsic fluorescence of the expressed recombinant or therapeutic polypeptide. An increase in the amount or concentration of functional product can be tested using various functional assays depending on the identity of the recombinant or therapeutic polypeptide. For example, antibodies can be tested by the ELISA or other immunoaffinity assay.

Methods for Cell Line and Recombinant Polypeptide Production

The current state of the art in both mammalian and microbial selection systems is to apply selective pressure at the level of the transcription of DNA into RNA. The gene of interest is coupled with the selective marker making a high level of expression of the selective marker likely to result in the high expression of the gene of interest. Cells which express the selective marker at high-enough levels to be able to survive and proliferate, those which do not are unlikely to survive and proliferate. In this way, a population of cells can be enriched for cells expressing the selective marker and by implication the gene of interest at high-levels. This method has proved very successful for expressing non-difficult to express proteins.

In some embodiments, additional steps may be performed to improve the expression of the product, e.g., transcription, translation, and/or secretion of the product, or the quality of the product, e.g., proper folding and/or fidelity of the primary sequence. Such additional steps include introducing an agent that improves product expression or product quality. In an embodiment, an agent that improves product expression or product quality can be a small molecule, a polypeptide, or a nucleic acid that encodes a polypeptide that improves protein folding, e.g., a chaperone protein. In an embodiment, the agent that assists in protein folding comprises a nucleic acid that encodes a chaperone protein, e.g., BiP, PD1, or ERO1 (Chakravarthi & Bulleid 2004; Borth et al. 2005; Davis et al. 2000). Other additional steps to improve yield and quality of the product include overexpression of transcription factors such as SBPI and ATF6 (Tigges & Fussenegger 2006; Cain et al. 2013; Ku et al. 2008) and of lectin binding chaperone proteins such as calnexin and calreticulin (Chung et al. 2004). Overexpression of the agents that assist or improve protein folding and product quality and yield proteins described herein can be achieved by introduction of exogenous nucleic acids encoding the proteins. In another embodiment, the agent that improves product expression or product quality is a small molecule that can be added to the cell culture to increase expression of the product or quality of the product. In one embodiment, culture of the cells at a lower temperature, e.g., 1° C., 2° C., 3° C., 4° C., 5° C., 6° C., 7° C., 8° C., 9° C., or 10° C. lower, than the temperature that the cells are normally grown in.

Any of the methods described herein can further include additional selection steps for identifying cells that have high productivity or produce high quality products. For example, FACs selection can be utilized to select specific cells with desired characteristics, e.g., higher expression of a protein folding proteins, e.g., chaperones.

In one aspect, the disclosure provides methods that include a step for recovering or retrieving the recombinant or therapeutic polypeptide product. In embodiments where the recombinant or therapeutic polypeptide is secreted from the cell, the methods can include a step for retrieving, collecting, or separating the recombinant or therapeutic polypeptide from the cell, cell population, or the culture medium in which the cells were cultured in. In embodiments where the recombinant or therapeutic polypeptide is within the cell, the purification of the recombinant or therapeutic polypeptide product comprises separation of the recombinant or therapeutic polypeptide produced by the cell from one or more of any of the following: host cell proteins, host cell nucleic acids, host cell lipids, and/or other debris from the host cell.

In embodiments, the process described herein provides a substantially pure protein product. As used herein, "substantially pure" is meant substantially free of pyrogenic materials, substantially free of nucleic acids, and/or substantially free of endogenous cellular proteins enzymes and components from the host cell, such as polymerases, ribosomal proteins, and chaperone proteins. A substantially pure protein product contains, for example, less than 25%, 20%, 15%, 10%, 9%, 8%, 7%, 6%, 5%, 4%, 3%, 2%, or 1% of contaminating endogenous protein (aka host cell protein), nucleic acid, or other macromolecule from the host cell.

Methods for recovering and purification of a product, e.g., a recombinant or therapeutic polypeptide, are well established in the art. For recovering the recombinant or therapeutic polypeptide product, a physical or chemical or physical-chemical method is used. The physical or chemical or physical-chemical method can be a filtering method, a centrifugation method, an ultracentrifugation method, an extraction method, a lyophilization method, a precipitation method, a chromatography method or a combination of two or more methods thereof. In an embodiment, the chromatography method comprises one or more of size-exclusion chromatography (or gel filtration), ion exchange chromatography, e.g., anion or cation exchange chromatography, affinity chromatography, hydrophobic interaction chromatography, and/or multimodal chromatography.

Repressor Polypeptides

Provided herein are repressor polypeptides and repressor polypeptide encoding sequences useful in genetic control circuits, cells, and methods for identifying, selecting or making a cell or cell line capable of producing high yields of a product, e.g., a recombinant or therapeutic polypeptide. In general, repressor polypeptides inhibit expression of the product, e.g., a recombinant or therapeutic polypeptide, in a regulated manner. In some embodiments, the repressor polypeptide encoding sequence is under the transcriptional control of a control element which activates transcription of the repressor polypeptide encoding sequence dependent on one or more conditions. In some embodiments, a repressor polypeptide binds to the control element, e.g., promoter element, operably linked to the recombinant or therapeutic polypeptide encoding sequence. In some embodiments, binding of the repressor polypeptide to a control element inhibits transcription of the operably linked recombinant or therapeutic polypeptide encoding sequence. In some embodiments, a repressor polypeptide binds to a sequence encoding an untranslated region of the transcript of the recombinant or therapeutic polypeptide. In some embodiments, binding of the repressor polypeptide to an untranslated region of the transcript of the recombinant or therapeutic polypeptide inhibits translation of the recombinant or therapeutic polypeptide encoding sequence. In some embodiments, a repressor polypeptide binds to the coding sequence of the recombinant or therapeutic polypeptide encoding sequence. In some embodiments, binding of the repressor polypeptide to the coding sequence of the recombinant or therapeutic polypeptide inhibits transcription, translation, or transcription and translation of the recombinant or therapeutic polypeptide encoding sequence.

It is contemplated that the present disclosure is not specific to a particular repressor polypeptide. Exemplary repressor polypeptides include but are not limited to: Cas9 molecules, TALE molecules, and zinc finger molecules. In some embodiments, the repressor polypeptide is a Cas-related protein known in the art. In some embodiments, the repressor polypeptide is a protein from a type I, II, or II CRISPR/Cas system (e.g. as described in K. S. Makarova et al., Nat. Rev. Microbiol. 9, 467 (2011); K. S. Makarova, N. V. Grishin, S. A. Shabalina, Y. I. Wolf, E. V. Koonin, Biol. Direct 1, 7 (2006); or K. S. Makarova, L. Aravind, Y. I. Wolf, E. V. Koonin, Biol. Direct 6, 38 (2011)).

In some embodiments, the repressor polypeptide is a Cas9 molecule. Repressor polypeptides that are Cas9 molecules require one or more (e.g., one, two, three, four or more) suitable gRNAs to inhibit expression of a recombinant or therapeutic polypeptide.

In some embodiments, the repressor polypeptide is a TALE molecule.

In some embodiments, the repressor polypeptide is a zinc finger molecule.

In some embodiments, the repressor polypeptide is an endogenous repressor of the first control element, e.g., the first promoter element. In an embodiment, the endogenous gene encoding the repressor polypeptide is inactive, e.g., has been knocked out or mutated to produce a loss of function.

Cas9 Molecules

Cas9 molecules to be used in the genetic control circuits, cells, and methods of the present disclosure may comprise polypeptides originating in a variety of species. In addition, one or more domains from a Cas9 molecule in one species may be combined with one or more domains from a Cas9 molecule in another species, e.g., in a fusion protein. Additional Cas9 polypeptide comprising species include: *Acidovorax avenae, Actinobacillus pleuropnemoniae, Actinobacillus succinogenes, Actinobacillus suis, Actinomyces* sp., *cycliphilus denitrificans, Aminomonas paucivorns, Bacillus cereus, Bacillus smithii, Bacillus thuringiensis, Bacteroides* sp., *Blautopirellula marina, Bradyrhizobium* sp., *Brevibacillus laterosporus, Campylobacter coli, Campylobsacer jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parinfluenze, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cineres, Neisseria flvescens, Neisseria lactamice, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiells muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eisenise.*

Cas9 Structure and Activity

Crystal structures are available for naturally occurring Cas9 polypeptides (Jinek et al., Science, 343(6176): 1247997, 2014) and for *S. pyogenes* Cas9 with a guide RNA (e.g., a synthetic fusion of crRNA and tracrRNA) (Nishimasu et al., Cell, 156:935-949, 2014; and Anders et al., Nature, 2014, doi: 10.1038/nature13579).

In an embodiment, a Cas9 molecule or Cas9 polypeptide comprises one or more of the following domains: a RuvC-like domain and an HNH-like domain. In an embodiment, a Cas9 molecule or Cas9 polypeptide is a dCas9 molecule or dCas9 polypeptide and the dCas9 molecule or dCas9 polypeptide comprises a RuvC-like domain, e.g., a RuvC-like domain that lacks nuclease activity, and/or an HNH-like domain, e.g., an HNH-like domain that lacks nuclease activity.

In an embodiment, the Cas9 molecule or Cas9 polypeptide can include more than one RuvC-like domain (e.g., one, two, three or more RuvC-like domains). In an embodiment, a RuvC-like domain comprises one or more mutations that alter its activity, such that the RuvC domain does not cleave DNA or has reduced DNA cleaving activity. In an embodiment, a RuvC-like domain is at least 5, 6, 7, 8 amino acids in length but not more than 20, 19, 18, 17, 16 or 15 amino acids in length. In an embodiment, the Cas9 molecule or Cas9 polypeptide comprises an N-terminal RuvC-like domain of about 10 to 20 amino acids, e.g., about 15 amino acids in length.

In an embodiment, the Cas9 molecule or Cas9 polypeptide can include more than one HNH-like domain (e.g., one, two, three or more HNH-like domains). In an embodiment, an HNH-like domain comprises one or more mutations that alter its activity, such that the HNH-like domain does not cleave DNA or has reduced DNA cleaving activity. In an embodiment, an HNH-like domain is at least 15, 20, 25 amino acids in length but not more than 40, 35 or 30 amino acids in length, e.g., 20 to 35 amino acids in length, e.g., 25 to 30 amino acids in length.

In embodiments, Cas9 molecules or Cas9 polypeptides have the ability to interact with a gRNA molecule, and in conjunction with the gRNA molecule localize to a core target domain, but are incapable of cleaving the target nucleic acid, or incapable of cleaving at efficient rates. Cas9 molecules having no, or no substantial, cleavage activity are referred to herein as dCas9 molecules or dCas9 polypeptides. For example, a dCas9 molecule or dCas9 polypeptide can lack cleavage activity or have substantially less, e.g., less than 20, 10, 5, 1 or 0.1% of the cleavage activity of a reference Cas9 molecule or Cas9 polypeptide, as measured by assays known in the art or assays described herein.

Targeting and PAMs

A Cas9 molecule or Cas9 polypeptide, is a polypeptide that can interact with a guide RNA (gRNA) molecule and, in concert with the gRNA molecule, localizes to a site which comprises a target domain and PAM sequence.

In an embodiment, the ability of a Cas9 molecule or Cas9 polypeptide to interact with a target nucleic acid is PAM sequence dependent. A PAM sequence is a sequence in the target nucleic acid. Cas9 molecules from different bacterial species can recognize different sequence motifs (e.g., PAM sequences). Cas9 molecules can be engineered to alter the PAM specificity of the Cas9 molecule. Exemplary naturally occurring Cas9 molecules are described in Chylinski et al., RNA BIOLOGY 2013 10:5, 727-737.

Alterations in Cas9 Structure

In some embodiments, one or more mutation(s) can be present, e.g., in one or more RuvC-like domain, e.g., an N-terminal RuvC-like domain; an HNH-like domain; a region outside the RuvC-like domains and the HNH-like domain, of the Cas9 molecule or Cas9 polypeptide. In some embodiments, a mutation(s) is present in a RuvC-like domain, e.g., an N-terminal RuvC-like domain. In some embodiments, a mutation(s) is present in an HNH-like domain. In some embodiments, mutations are present in both a RuvC-like domain, e.g., an N-terminal RuvC-like domain and an HNH-like domain.

In an embodiment, a Cas9 molecule or Cas9 polypeptide, e.g., an dCas9 molecule or dCas9 polypeptide, comprises an amino acid sequence:

having 60%, 65%, 70%, 75%, 80%, 85%, 90%, 95%, 96%, 97%, 98% or 99% homology with;

differs at no more than, 2, 5, 10, 15, 20, 30, or 40% of the amino acid residues when compared with;

differs by at least 1, 2, 5, 10 or 20 amino acids, but by no more than 100, 80, 70, 60, 50, or 30 amino acids from; or is identical to any Cas9 molecule sequence described herein, or a naturally occurring Cas9 molecule sequence, e.g., a Cas9 molecule from a species listed herein or described in Chylinski et al., RNA BIOLOGY 2013 10:5, 727-737; Hou et al., PNAS Early Edition 2013, 1-6. In an embodiment, the Cas9 molecule or Cas9 polypeptide comprises one or more of the following activities: a helicase activity; or the ability, together with a gRNA molecule, to localize to a target nucleic acid. In an embodiment, the Cas9 molecule or Cas9 polypeptide does not comprise a nickase activity or a double stranded cleavage activity (e.g., an endonuclease and/or exonuclease activity).

Exemplary mutations that may be made in the RuvC domain or HNH domain with reference to the S. pyogenes sequence include: D10A, E762A, H840A, N854A, N863A and/or D986A.

Exemplary Cas9 polypeptide and Cas9 domain sequences can be found in Tables 50-54 of WO2015/157070.

dCas9 Repressor Polypeptides

In an embodiment, a Cas9 molecule or Cas9 polypeptide is a dCas9 molecule or dCas9 polypeptide comprising one or more differences in a RuvC domain and/or in an HNH domain as compared to a reference Cas9 molecule, and the dCas9 molecule or dCas9 polypeptide does not cleave a nucleic acid, or cleaves with significantly less efficiency than does wildtype, e.g., when compared with wild type in a cleavage assay, e.g., as described herein, cuts with less than 50, 25, 10, or 1% of a reference Cas9 molecule, as measured by an assay described herein.

Mutating key residues in both DNA cleavage domains of the Cas9 protein (e.g. the D10A and H840A mutations) results in the generation of a catalytically inactive Cas9 (dCas9 which is also known as dead Cas9) molecule. An enzymatically inactive Cas9, e.g., dCas9, complexes with a gRNA and localizes to the DNA sequence specified by that gRNA's targeting domain; however, it does not cleave the target DNA. An enzymatically inactive (e.g., dCas9) Cas9 molecule can block transcription when recruited to early regions in the coding sequence. Additional repression can be achieved by fusing a transcriptional repression domain (for example KRAB, SID or ERD) to the enzymatically inactive Cas9, e.g., dCas9, and recruiting it to the target sequence, e.g., within 1000 bp of sequence 3' of the start codon or within 500 bp of a control element, e.g., promoter element, e.g., 5' of the start codon of a gene. Targeting DNase I hypersensitive sites (DHSs) of the promoter (e.g., by making gRNAs complementary to the DHSs) may be an additional strategy for gene repression, e.g., inhibition of a recombinant or therapeutic polypeptide encoding sequence, because these regions are more likely to be accessible to the enzymatically inactive Cas9, e.g., dCas9, and are also likely to harbor sites for endogenous transcription factors. While not wishing to be bound by theory, it is contemplated herein that blocking the binding site of an endogenous transcription factor or RNA polymerase would aid in down-regulating gene expression, e.g., expression of a recombinant or therapeutic polypeptide encoding sequence. In an embodiment, one or more enzymatically inactive Cas9, e.g., dCas9, molecules may be used to block binding of one or more endogenous transcription factors. In another embodiment, an enzymatically inactive Cas9, e.g., dCas9, molecule can be fused to an effector domain, e.g., a repression domain, an activation domain, a methylation enzyme, etc. Fusion of the enzymatically inactive Cas9, e.g., dCas9, to an effector domain enables recruitment of the effector to any DNA site specified by the gRNA. Altering chromatin status can result in decreased expression of the target gene. One or more enzymatically inactive Cas9, e.g., dCas9, molecules fused to one or more chromatin modifying proteins may be used to alter chromatin status.

In an embodiment, a gRNA molecule can be targeted to a control element (e.g., promoter element), e.g., the control element operably linked to a recombinant or therapeutic polypeptide encoding sequence. In an embodiment a gRNA molecule can be targeted to a sequence encoding a recombinant or therapeutic polypeptide.

gRNA Molecules

A gRNA molecule, as that term is used herein, refers to a nucleic acid that promotes the specific targeting or homing of a gRNA molecule/Cas9 molecule complex to a target sequence. gRNA molecules can be unimolecular (comprising a single RNA molecule), sometimes referred to herein as "chimeric" gRNAs, or modular (comprising more than one, and typically two, separate RNA molecules). A gRNA molecule comprises a number of domains.

In an embodiment, a unimolecular, or chimeric, gRNA comprises, typically from 5' to 3':
  a targeting domain
  a first complementarity domain;
  a linking domain;
  a second complementarity domain (which is complementary to the first complementarity domain);
  a proximal domain; and
  optionally, a tail domain.

In an embodiment, a modular gRNA comprises:
  a first strand comprising, typically from 5' to 3';
    a targeting domain
    a first complementarity domain; and
  a second strand, comprising, typically from 5' to 3':
    optionally, a 5' extension domain;
    a second complementarity domain;
    a proximal domain; and
    optionally, a tail domain.

In an embodiment, a gRNA comprises a first strand comprising a tracrRNA and a second strand comprising a crRNA. Exemplary tracrRNAs and crRNAs, and methods for design of same, can be found in the art, and for example, in Jinek et al. Science 17 Aug. 2012: Vol. 337, Issue 6096, pp. 816-821.

Exemplary gRNAs and methods for designing gRNAs, can be found in WO2015/157070, Xu, H., et al., Genome Res. 2015 August; 25(8):1147-57, and methods known in the art.

gRNA Domains

The targeting domain comprises a nucleotide sequence that is complementary, e.g., at least 80, 85, 90, or 95% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). In an embodiment, it is believed that the complementarity of the targeting domain with the target sequence contributes to specificity of the interaction of the gRNA molecule/Cas9 molecule complex with a target nucleic acid. In an embodiment, the targeting domain is 5 to 50 nucleotides in length. In some embodiments, a targeting domain has complementarity to the first control element, e.g., the first promoter element, the sequence encoding a recombinant or therapeutic polypeptide, or to an untranslated region or intron comprised within the first control element, e.g., first promoter element, or sequence encoding a recombinant or therapeutic polypeptide. The strand of the target nucleic acid with which the targeting domain is complementary is referred to herein as the complementary strand.

The first complementarity domain is complementary with the second complementarity domain, and in an embodiment, has sufficient complementarity to the second complementarity domain to form a duplexed region under at least some physiological conditions.

The first complementarity domain can share homology with, or be derived from, a naturally occurring first complementarity domain. In an embodiment, it has at least 50% homology with a first complementarity domain from *S. pyogenes, S. aureus* or *S. thermophilus*. A linking domain serves to link the first complementarity domain with the second complementarity domain of a unimolecular gRNA. The linking domain can link the first and second complementarity domains covalently or non-covalently. In an embodiment, the linkage is covalent. Typically the linking domain comprises one or more, e.g., 2, 3, 4, 5, 6, 7, 8, 9, or 10 nucleotides.

In modular gRNA molecules the two molecules are associated by virtue of the hybridization of the complementarity domains.

In an embodiment, a modular gRNA can comprise additional sequence, 5' to the second complementarity domain, referred to herein as the 5' extension domain. In an embodiment, the 5' extension domain is 2, 3, 4, 5, 6, 7, 8, 9, or 10 or more nucleotides in length.

The second complementarity domain is complementary with the first complementarity domain, and in an embodiment, has sufficient complementarity to the second complementarity domain to form a duplexed region under at least some physiological conditions. In an embodiment the second complementarity domain can include sequence that lacks complementarity with the first complementarity domain, e.g., sequence that loops out from the duplexed region. In an embodiment, the second complementarity domain is 5 to 27 nucleotides in length. In an embodiment, it is longer than the first complementarity region. The second complementarity domain can share homology with or be derived from a naturally occurring second complementarity domain. In an embodiment, it has at least 50% homology with a second complementarity domain from *S. pyogenes, S. aureus* or *S. thermophilus*.

In an embodiment, the proximal domain is 5 to 20 nucleotides in length. In an embodiment, the proximal domain can share homology with or be derived from a naturally occurring proximal domain. In an embodiment, it has at least 50% homology with a proximal domain from *S. pyogenes, S. aureus* or *S. thermophilus*.

In an embodiment, the tail domain is 0 (absent), 1, 2, 3, 4, 5, 6, 7, 8, 9, or 10 nucleotides in length. In an embodiment, the tail domain nucleotides are from or share homology with sequence from the 5' end of a naturally occurring tail domain. In an embodiment, it has at least 50% homology with a tail domain disclosed herein, e.g., an *S. pyogenes, S. aureus* or *S. thermophilus*, tail domain. In an embodiment, the tail domain includes sequences that are complementary to each other and which, under at least some physiological conditions, form a duplexed region.

In an embodiment, the tail domain includes nucleotides at the 3' end that are related to the method of in vitro or in vive transcription. When a U6 promoter is used for in vive transcription, these nucleotides may be the sequence UUUUUU.

Methods for Designing gRNAs

Methods for selection and validation of gRNA target sequences as well as off-target analyses are described, e.g., in Mali et al., 2013 SCIENCE 339(6121): 823-826; Hsu et al. NAT BIOTECHNOL, 31(9): 827-32; Fu et al., 2014 NAT BIOTECHNOL, doi: 10.1038/nbt.2808. PubMed PMID: 24463574; Heigwer et al., 2014 NAT METHODS 11(2):122-3. doi: 10.1038/nmeth.2812. PubMed PMID: 24481216; Bae et al., 2014 BIOINFORMATICS PubMed PMID: 24463181; Xiao A et al., 2014 BIOINIERMATICS PubMed PMID: 24389662.

For example, a software tool can be used to optimize the choice of gRNA within a user's target sequence, e.g., to minimize total off-target activity across the genome. Off target activity may be DNA binding, DNA cleavage, DNA nicking, or another activity. For each possible gRNA choice using *S. pyogenes* Cas9, the tool can identify all off-target sequences (preceding either NAG or NGG PAMs) across the genome that contain up to certain number (e.g., 1, 2, 3, 4, 5, 6, 7, 8, 9, or 10) of mismatched base-pairs. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-generation sequencing, can also be included in the tool. Candidate gRNA molecules can be evaluated by methods known in the art.

TALE Molecules

A transcription activator-like effector (TALE) molecule or TALE polypeptide, as that term is used herein, refers to a molecule or polypeptide comprising multiple TALE DNA-binding repeat domains (TALE DBDs) that can home or localize to a nucleic acid position specified by the TALE DBDs. TALE molecule and TALE polypeptide, as those terms are used herein, refer to naturally occurring TALE molecules and to engineered, altered, or modified TALE molecules or TALE polypeptides that differ, e.g., by at least one amino acid residue, from a reference sequence, e.g., the most similar naturally occurring TALE molecule known in the art.

TALE DBD, as that term is used herein, refers to a 33-35 amino acid motif, including two hypervariable residues (i.e. a repeat variable di-residue, RVD) at positions 12 and 13 of the motif. The RVD of a TALE DNA-binding domain (DBD) specifies the DNA base-pair or base-pairs to which a TALE DBD has binding affinity. When TALE DBDs are combined in arrays within a TALE molecule or TALE polypeptide, the order of TALE DBDs (and their RVD) determine the DNA sequence to which a TALE molecule or TALE polypeptide has binding affinity. Naturally occurring TALE polypeptides and TALE DBDs are produced by *Xanthomones* bacteria.

Repeat variable di-residue (RVD), as that term is used herein, refers to the two hypervariable amino acid residues at positions 12 and 13 of a TALE DBD. The RVD determines the DNA base-pair affinity of a TALE DBD. All possible combinations of RVDs and their respective base-pair affinities are known in the art. See, e.g., Cong L., et al. Nat Commun. 2012 Jul. 24; 30:968; Juillerat A., et al. Sci Rep. 2015 Jan. 30; 50:8150; Miller J. C. et al. Nat Methods 12, 465-471 (2015); Streubel J., et al. Nat Biotechnol 30, 593-595 (2012); and Yang J. et al. Cell Res 24, 628-631 (2014), incorporated herein by reference in their entirety. All possible RVDs are contemplated for use with the repressor polypeptides, e.g., TALE molecules, described herein.

TALE DBD array, as that term is used herein, refers to the identities and order of TALE DBDs, e.g., the RVDs of each TALE DBD, within a TALE molecule or TALE polypeptide. The TALE DBD array determines the sequence specific binding affinity of a TALE molecule or TALE polypeptide.

In some embodiments, the repressor polypeptide is a TALE molecule or TALE polypeptide. TALE DBDs and TALE polypeptide from any species of *Xanthomones* can be used in the genetic control circuits, cells, and methods for identifying, selecting, or making a cell or cell line capable of producing high yields of a product, e.g., a recombinant or therapeutic polypeptide, described herein. In some embodiments, the repressor polypeptide is a naturally occurring TALE molecule or TALE polypeptide. In some embodiments, the repressor polypeptide is an engineered TALE molecule or TALE polypeptide, i.e. a TALE molecule or TALE polypeptide that differs by one or more amino acids from a naturally occurring TALE molecule or TALE polypeptide or from another engineered TALE molecule or TALE polypeptide known in the art.

In some embodiments, an engineered TALE molecule or TALE polypeptide comprises an amino acid sequence:
- having 60%, 65%, 70%, 75%, 80%, 85%, 90%, 95%, 96%, 97%, 98% or 99% homology with;
- differs at no more than, 2, 5, 10, 15, 20, 30, or 40% of the amino acid residues when compared with;
- differs by at least 1, 2, 5, 10 or 20 amino acids, but by no more than 100, 80, 70, 60, 50, 40 or 30 amino acids from; or
- is identical to any TALE molecule sequence described herein, or a naturally occurring TALE molecule sequence, e.g., a TALE molecule from a species listed herein or described in a publication referenced herein.

In some embodiments, a TALE molecule localizes to the target DNA sequence specified by that TALE molecules' TALE DBD array. In some embodiments, TALE molecule can block transcription when recruited to early regions in a coding sequence, e.g., the coding sequence of a recombinant or therapeutic polypeptide. In some embodiments, a TALE molecule can block transcription when recruited to a control element, e.g., a promoter element, operably linked to a recombinant or therapeutic polypeptide encoding sequence. In some embodiments, additional repression can be achieved by fusing a transcriptional repression domain (for example KRAB, SID or ERD) to the TALE molecule, enabling recruitment of the effector to any DNA site specified by the TALE DBD array.

In some embodiments, a TALE molecule comprises two or more (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more) TALE DBDs.

In some embodiments, the TALE DBD array of a repressor polypeptide, e.g., TALE molecule, specifies a target DNA sequence. In some embodiments, the target sequence specified by the TALE DBD array is comprised within a control element, e.g., promoter element, operably linked to a recombinant or therapeutic polypeptide encoding sequence. In some embodiments, the target sequence specified by the TALE DBD array is comprised with a recombinant or therapeutic polypeptide encoding sequence.

Exemplary naturally occurring and engineered TALE polypeptide sequences and methods for design and testing of TALE polypeptides for use with genetic control circuits, cells, and methods for identifying, selecting, or making a cell or cell line capable of producing high yields of a product, e.g., a recombinant or therapeutic polypeptide, described herein can be found in the art, e.g., in Zhang F, et al. Nat Biotechnol. 2011; 29:149-153; Geissler R, et al. PLoS One. 2011; 6:e19509; Garg A, et al. Nucleic Acids Res. 2012; Bultmann S, et al. Nucleic Acids Res. 2012; 40:5368-5377; Cermak T, et al. Efficient design and assembly of custom TALEN and other TAL effector-based constructs for DNA targeting. Nucleic Acids Res. 2011; 39:e82; Cong L, et al. Nat Commun. 2012; 3:968; and Miller J C, et al. Nat Biotechnol. 2011; 29:143-148, herein incorporated by reference in their entirety.

Zinc Finger Molecules

A zinc finger molecule, as that term is used herein, refers to a molecule or polypeptide comprising multiple zinc finger domains (ZFDs). A zinc finger molecule has affinity to a specific DNA sequence determined by the identity and order of the ZFDs the zinc finger molecule comprises.

A zinc finger domain (ZFD), as that term is used herein, refers to any of a family of polypeptides that bind DNA in a sequence specific manner and require a zinc ion ligand to bind DNA. Many families of ZFDs have been studied and characterized (see, e.g., Krishna, S S., et al. Nucl. Acids Res. (2003) 31 (2): 532-550). The disclosure contemplates zinc finger molecules that may comprise ZFDs of any type or origin known to those of skill in the art. Without intending to be limited to any particular type of ZFD, the disclosure contemplates zinc finger molecules comprising $Cys_2His_2$ ZFDs, which are the most prevalent and well-studied ZFDs in the art. $Cys_2His_2$ ZFDs comprise two beta strands that form an anti-parallel beta sheet and an alpha helix. Positions −1, 1, 2, 3, 5, and 6 of the alpha helix are known to specify DNA sequence specific binding by interacting with DNA base pairs. In an embodiment, a $Cys_2His_2$ ZFD may have specific binding affinity for a 3 base pair target sequence. In an embodiment, a $Cys_2His_2$ ZFD may specifically interact with an additional base pair adjacent to the target sequence in a context specific manner, i.e. dependent upon the presence and identity of adjacent ZFDs within a zinc finger molecule.

A zinc finger domain array, or ZFD array, as that term is used herein, refers to the identities and order of ZFDs, within a zinc finger molecule or zinc finger polypeptide. The ZFD array determines the sequence specific binding affinity of a zinc finger molecule or zinc finger polypeptide.

In some embodiments, the repressor polypeptide is a zinc finger molecule or zinc finger polypeptide. ZFDs and zinc finger polypeptides from any species (e.g., a mammalian species, e.g., humans) can be used in the genetic control circuits, cells, and methods for identifying, selecting, or making a cell or cell line capable of producing high yields of a product, e.g., a recombinant or therapeutic polypeptide, described herein. In some embodiments, the repressor polypeptide is a naturally occurring zinc finger molecule or zinc finger polypeptide. In some embodiments, the repressor polypeptide is an engineered zinc finger molecule or zinc finger polypeptide, i.e. a zinc finger molecule or zinc finger polypeptide that differs by one or more amino acids from a naturally occurring zinc finger molecule or zinc finger polypeptide or from another engineered zinc finger molecule or zinc finger polypeptide known in the art.

In some embodiments, an engineered zinc finger molecule or zinc finger polypeptide comprises an amino acid sequence:
- having 60%, 65%, 70%, 75%, 80%, 85%, 90%, 95%, 96%, 97%, 98% or 99% homology with;
- differs at no more than, 2, 5, 10, 15, 20, 30, or 40% of the amino acid residues when compared with;
- differs by at least 1, 2, 5, 10 or 20 amino acids, but by no more than 100, 80, 70, 60, 50, 40 or 30 amino acids from; or
- is identical to any zinc finger molecule sequence described herein, or a naturally occurring zinc finger molecule sequence, e.g., a zinc finger molecule from a species listed herein or described in a publication referenced herein.

In some embodiments, a zinc finger molecule localizes to the target DNA sequence specified by that zinc finger molecules' ZFD array. In some embodiments, a zinc finger molecule can block transcription when recruited to early regions in a coding sequence, e.g., the coding sequence of a recombinant or therapeutic polypeptide. In some embodiments, a zinc finger molecule can block transcription when recruited to a control element, e.g., a promoter element, operably linked to a recombinant or therapeutic polypeptide encoding sequence. In some embodiments, additional repression can be achieved by fusing a transcriptional repression domain (for example KRAB, SID or ERD) to the zinc finger molecule, enabling recruitment of the effector to any DNA site specified by the ZFD array.

In some embodiments, a zinc finger molecule comprises two or more (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more) ZFDs. In some embodiments, a ZFD array can be constructed from ZFDs with known target sequence affinities to create a zinc finger molecule or zinc finger polypeptide with a desired specific target sequence.

In some embodiments, the ZFD array of a repressor polypeptide, e.g., zinc finger molecule, specifies a target DNA sequence. In some embodiments, the target sequence specified by the ZFD array is comprised within a control element, e.g., promoter element, operably linked to a recombinant or therapeutic polypeptide encoding sequence. In some embodiments, the target sequence specified by the ZFD array is comprised with a recombinant or therapeutic polypeptide encoding sequence.

Exemplary naturally occurring and engineered zinc finger polypeptide sequences and methods for design and testing of zinc finger polypeptides for use with genetic control circuits, cells, and methods for identifying, selecting, or making a cell or cell line capable of producing high yields of a product, e.g., a recombinant or therapeutic polypeptide, described herein can be found in the art, e.g., in Wolfe S A, et al. Annu Rev Biophys Biomol Struct. 2000; 29:183-212; Pabo C O, et al. Annu Rev Biochem. 2001; 70.313-340; Greisman H A, Pabo C O. Science. 1997; 275:657-661; Isalan M, et al. Proc Natl Acad Sci USA. 1997; 94:5617-5621; Wolfe S A, et al. J Mol Biol. 1999; 285:1917-1934, herein incorporated by reference in their entirety.

Methods of designing ZFDs and ZFD arrays to bind specific target DNA sequences can be found in the art, e.g., in Maeder M L, et al. Mol Cell. 2008; 31:294-301; Sander J D, et al. Nat Methods. 2011; 8:67-69; and Meng X, et al. Nat Biotechnol. 2008; 26:695-701, herein incorporated by reference in their entirety.

Application to Production

The cells, methods, kits, reaction mixtures, and nucleic acids disclosed herein can be of use in a bioreactor or processing vessel or tank, or, more generally with any feed source. The devices, facilities and methods described herein are suitable for culturing any desired cell line including prokaryotic and/or eukaryotic cell lines. Also included are industrial facilities that include components that are suitable for culturing suspension cells or anchorage-dependent (adherent) cells and are suitable for production operations configured for production of pharmaceutical and biopharmaceutical products-such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

Also included are industrial facilities that include components that allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the facility can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the facility can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 200910305626; and U.S. Pat. Nos. 8,298,054; 7,629,167; and 5,656,491, which are hereby incorporated by reference in their entirety, describe example facilities, equipment, and/or systems that may be suitable.

Exemplary Sequences
Exemplary Guide RNA Target Sequences in the hCMV Promoter and Intron

```
(PAM sequence underlined)
All 5' to 3' gRNA 1
                                                            (SEQ ID NO: 1)
TGTCAACATGGCGGTAATGTTGG gRNA 2
                                                            (SEQ ID NO: 2)
TACCGCCCATTTGCGTCAATGGG gRNA 3
                                                            (SEQ ID NO: 3)
CTACCGCCCATTTGCGTCAATGG gRNA14
                                                            (SEQ ID NO: 4)
ACCGTTAACAGCACCGCAACGGG

Sequence 5-hCMV-MIE region targeted by gRNAs

>pEE12.4 (5412 bp-7528 bp, direct) 2108 bp
                                                            (SEQ ID NO: 5)
CTGCAGTGAATAATAAAATGTGTGTTTGTCCGAAATACGCGTTTTGAGATTTCTGTCGCCGACTAAATTCATGTCG

CGCGATAGTGGTGTTTATCGCCGATAGAGATGGCGATATTGGAAAAATCGATATTTGAAAATATGGCATATTGAAA

ATGTCGCCGATGTGAGTTTCTGTGTAACTGATATCGCCATTTTTCCAAAAGTGATTTTTGGGCATACGCGATATCT

GGCGATAGCGCTTATATCGTTTACGGGGGATGGCGATAGACGACTTTGGTGACTTGGGCGATTCTGTGTGTCGCAA

ATATCGCAGTTTCGATATAGGTGACAGACGATATGAGGCTATATCGCCGATAGAGGCGACATCAAGCTGGCACATG

GCCAATGCATATCGATCTATACATTGAATCAATATTGGCCATTAGCCATATTATTCATTGGTTATATAGCATAAAT

CAATATTGGCTATTGGCCATTGCATACGTTGTATCCATATCATAATATGTACATTTATATTGGCTCATGTCCAACA

TTACCGCCATGTTGACATTGATTATTGACTAGTTATTAATAGTAATCAATTACGGGGTCATTAGTTCATAGCCCAT

ATATGGAGTTCCGCGTTACATAACTTACGGTAAATGGCCCGCCTGGCTGACCGCCCAACGACCCCCGCCCATTGAC

GTCAATAATGACGTATGTTCCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATTGACGTCAATGACGGTAAAT

GGCCCGCCTGGCATTATGCCCAGTACATGACCTTATGGGACTTTCCTACTTGGCAGTACATCTACGTATTAGTCAT

CGCTATTACCATGGTGATGCGGTTTTGGCAGTACATCAATGGGCGTGGATAGCGGTTTGACTCACGGGGATTTCCA

AGTCTCCACCCCATTGACGTCAATGGGAGTTTGTTTTGGCACCAAAATCAACGGGACTTTCCAAAATGTCGTAACA

ACTCCGCCCCATTGACGCAAATGGGCGGTAGGCGTGTACGGTGGGAGGTCTATATAAGCAGAGCTCGTTTAGTGAA

CCGTCAGATCGCCTGGAGACGCCATCCACGCTGTTTTGACCTCCATAGAAGACACCGGGACCGATCCAGCCTCCGC

GGCCGGGAACGGTGCATTGGAACGCGGATTCCCCGTGCCAAGAGTGACGTAAGTACCGCCTATAGAGTCTATAGGC

CCACCCCCTTGGCTTCTTATGCATGCTATACTGTTTTTGGCTTGGGGTCTATACACCCCCGCTTCCTCATGTTATA

GGTGATGGTATAGCTTAGCCTATAGGTGTGGGTTATTGACCATTATTGACCACTCCCCTATTGGTGACGATACTTT

CCATTACTAATCCATAACATGGCTCTTTGCCACAACTCTCTTTATTGGCTATATGCCAATACACTGTCCTTCAGAG

ACTGACACGGACTCTGTATTTTTACAGGATGGGGTCTCATTTATTATTTTACAAATTCACATATACAACACCACCGT
```

-continued

CCCCAGTGCCCGCAGTTTTTATTAAACATAACGTGGGATCTCCACGCGAATCTCGGGTACGTGTTCCGGACATGGG

CTCTTCTCCGGTAGCGGCGGAGCTTCTACATCCGAGCCCTGCTCCCATGCCTCCAGCGACTCATGGTCGCTCGGCA

GCTCCTTGCTCCTAACAGTGGAGGCCAGACTTAGGCACAGCACGATGCCCACCACCACCAGTGTGCCGCACAAGGC

CGTGGCGGTAGGGTATGTGTCTGAAAATGAGCTCGGGGAGCGGGCTTGCACCGCTGACGCATTTGGAAGACTTAAG

GCAGCGGCAGAAGAAGATGCAGGCAGCTGAGTTGTTGTGTTCTGATAAGAGTCAGAGGTAACTCCCGTTGCGGTGC

TGTTAACGGTGGAGGGCAGTGTAGTCTGAGCAGTACTCGTTGCTGCCGCGCGCCACCAGACATAATAGCTGACA

GACTAACAGACTGTTCCTTTCCATGGGTCTTTTCTGCAGTCACCGTCCTTGACACG

Sequence 6-U6 promoter
(SEQ ID NO: 6)
TGTACAAAAAAGCAGGCTTTAAAGGAACCAATTCAGTCGACTGGATCCGGTACCAAGGTCGGGCAGGAAGAGGGCC

TATTTCCCATGATTCCTTCATATTTGCATATACGATACAAGGCTGTTAGAGAGATAATTAGATTAATTTGACTGTA

AACACAAAGATATTAGTACAAAATACGTGACGTAGAAAGTAATAATTTCTTGGGTAGTTTGCAGTTTTAAAATTAT

GTTTTAAAATGGACTATCATATGCTTACCGTAACTTGAAAGTATTTCGATTTCTTGGCTTTATATATCTTGTGGAA

AGGACGAAACACC

Sequence 7-Grp78 promoter
>GA_Grp78_dCas9_Ub_Puro_U6_RGR_2 + 1 + 3 (15 bp-1508 bp, direct) 1494 bp
(SEQ ID NO: 7)
TAGCATAAGCTACAGATCAACCAGGTTATCAATTCTACCTGTACCACTCACCAGTGACTATTCTATTTAGCCACCC

CCCCCCAATGATCTCTTCTGGAAAATGGGAAACATCTACCAAGAATTAATCAAAGGACTAAATGACACATGCAAA

AAAAAAAAACCTTAGAACAGTGTTTTAAGCAGGATAAGTAGTTCAAGACCAGTTTGGACCATGTCTCAAAACTAA

AGGAACAACGAAGTACATTTAGTATTTTTTGCAACATGTTATTATTACATAGCATCAGGAAGACAATTTTTTCTTT

GTCTGCTAAATGCCTTTGTCATATCAGACCTATTTCAAGAGTCAGGATAGAATGGTGTCAAGAAGGGATGAGGAAG

GACTTGTAAATTATAACCAAGCCACAAATGAAAATGATAGACAAGGATCGGGAACATTATGGGGCGACAAGCTAGA

GAAAAAAAATGATATATTCCAGGGTGGAAAGTGCTCGCTTGACTATTCATAGAACAGAATAGCCACAGCATAGCGG

GGGGCTCAGTACTAGGTTGCAAATGGCCAGGCCAATTCTGGGACTTAACCCCAAGAAAAGAAAAATTGGCAAGGCC

AGGATAGACAAATGCAGCTGGCCTAGGGGTGAAGGGAAAACAGTTGGCTGAGAAGAGCCACGATTCGCAGAGAGGC

AGAACACAGACTAGGACCCAGCTCGAGACGTGCAGGCCGGGTGGGTAACATAGAGCCCGGGCGCTCGGCTACCCGA

GAACGTGAGGGAGGCTGGGAAGGGCAGAGATGCGTTCCCAGGCGACCACAGCATCTATGCTGAGGCTGAGCAGCTC

GGGACCCGAGGGGACTTAGGAGGAGAAAAGGCCGCATACTGCTTCGGGGTAAGGGACAGACCGGGGAAGGACCCAA

GTCCCACCGCCCAGAGGGAACTGACACGCAGACCCCGCAGCAGTCCCCGGGGCCGGGTGACGGGAGGACCTGGAC

GGTTACCGGCGGAAACGGTCTCGGGTTGAGAGGTCACCTGAGATGCTGCCTCTCATTGGCGGCCGTTGAGAGTAAC

CAGTAGCCAATGAGTCAGCCCGGGGGGCGTAGCGGTGACGTAAGTTGCGGAGGAGGCCGCTTCGAATCGGCAGCGG

CCAGCTTGGTGGCATGGACCAATCAGCGTCCTCCAACGAGAAGCGCCTTCACCAATCGGAGGCCTCCACGACGGGG

CTGGGGGAGGGTATATAAGCCAAGTCGGCGGCGGCGCGCTCCACACTGGCCAAGACAACAGTGACCGGAGGACCT

GCCTTTGCGGCTCCGAGAGGTAAGCGCCGCGGCCTGCTCTTGCCAGACCTCCTTTGAGCCTGTCTCGTGGCTCCTC

CTGACCCGGGGGCTTCTGTCGCCCTCAGATCGGAACGCCGCCGCGCTCCGGGACTACAGCCTGTTGCTGGACTTC

GAGACTGCAGACGGACCGACCGCTGAGCACTGGCCCACAGCGCCGGCAAG

HRE consensus sequence 1:
(SEQ ID NO: 8)
nGAAnnTTCnnGAA

HRE consensus sequence 2:
(SEQ ID NO: 9)
nGAAnnGAAnnTTCn

HRE consensus sequence 3:
(SEQ ID NO: 10)
nGAAnnGAAnnGAAn

HRE consensus sequence 4:
(SEQ ID NO: 11)
nTTCnnGAAnnGAAn

CRE consensus sequence:
(SEQ ID NO: 12)
TGACGTCA

ARE consensus sequence:
(SEQ ID NO: 13)
TGAG/CnnnGC

ERSE consensus sequence:
(SEQ ID NO: 14)
CCAAT(N9)CCACG

Wildtype *S. pyogenes* Cas9:
(SEQ ID NO: 15)
MDKKYSIGLD IGTNSVGWAV ITDEYKVPSK KFKVLGNTDR HSIKKNLIGA LLFDSGETAE ATRLKRTARR
RYTRRKNRIC YLQEIFSNEM AKVDDSFFHR LEESFLVEED KKHERHPIFG NIVDEVAYHE KYPTIYHLRK
KLVDSTDKAD LRLIYLALAH MIKFRGHFLI EGDLNPDNSD VDKLFIQLVQ TYNQLFEENP INASGVDAKA
ILSARLSKSR RLENLIAQLP GEKKNGLFGN LIALSLGLTP NFKSNFDLAE DAKLQLSKDT YDDDLDNLLA
QIGDQYADLF LAAKNLSDAI LLSDILRVNT EITKAPLSAS MIKRYDEHHQ DLTLLKALVR QQLPEKYKEI
FFDQSKNGYA GYIDGGASQE EFYKFIKPIL EKMDGTEELL VKLNREDLLR KQRTFDNGSI PHQIHLGELH
AILRRQEDFY PFLKDNREKI EKILTFRIPY YVGPLARGNS RFAWMTRKSE ETITPWNFEE VVDKGASAQS
FIERMTNFDK NLPNEKVLPK HSLLYEYFTV YNELTKVKYV TEGMRKPAFL SGEQKKAIVD LLFKTNRKVT
VKQLKEDYFK KIEVFDSVEI SGVEDRFNAS LGTYHDLLKI IKDKDFLDNE ENEDILEDIV LTLTLFEDRE
MIEERLKTYA HLFDDKVMKQ LKRRRYTGWG RLSRKLINGI RDKQSGKTIL DFLKSDGFAN RNFMQLIHDD
SLTFKEDIQK AQVSGQGDSL HEHIANLAGS PAIKKGILQT VKVVDELVKV MGRHKPENIV IEMARENQTT
QKGQKNSRER MKRIEEGIKE LGSQILKEHP VENTQLQNEK LYLYYLQNGR DMYVDQELDI NRLSDYDVDH
IVPQSFLKDD SIDNKVLTRS DKNRGKSDNV PSEEVVKKMK NYWRQLLNAK LITQRKFDNL TKAERGGLSE
LDKAGFIKRQ LVETRQITKH VAQILDSRMN TKYDENDKLI REVKVITLKS KLVSDFRKDF QFYKVREINN
YHHAHDAYLN AVVGTALIKK YPKLESEFVY GDYKVYDVRK MIAKSEQEIG KATAKYFFYS NIMNFFKTEI
TLANGEIRKR PLIETNGETG EIVWDKGRDF ATVRKVLSMP QVNIVKKTEV QTGGFSDESI LPKRNSDKLI
ARKKDWDPKK YGGFDSPTVA YSVLVVAKVE KGKSKKLKSV KELLGITIME RSSFEKNPID FLEAKGYKEV
KKDLIIKLPK YSLFELENGR KRMLASAGEL QKGNELALPS KYVNFLYLAS HYEKLKGSPE DNEQKQLFVE
QHKHYLDEII EQISEFSKRV ILADANLDKV LSAYNKHRDK PIREQAENII HLFTLTNLGA PAAFKYFDTT
IDRKRYTSTK EVLDATLIHQ SITGLYETRI DLSQLGGD dCas9:
(SEQ ID NO: 16)
MDKKYSIGLA IGTNSVGWAV ITDEYKVPSK KFKVLGNTDR HSIKKNLIGA LLFDSGETAE ATRLKRTARR
RYTRRKNRIC YLQEIFSNEM AKVDDSFFHR LEESFLVEED KKHERHPIFG NIVDEVAYHE KYPTIYHLRK
KLVDSTDKAD LRLIYLALAH MIKFRGHFLI EGDLNPDNSD VDKLFIQLVQ TYNQLFEENP INASGVDAKA
ILSARLSKSR RLENLIAQLP GEKKNGLFGN LIALSLGLTP NFKSNFDLAE DAKLQLSKDT YDDDLDNLLA
QIGDQYADLF LAAKNLSDAI LLSDILRVNT EITKAPLSAS MIKRYDEHHQ DLTLLKALVR QQLPEKYKEI
FFDQSKNGYA GYIDGGASQE EFYKFIKPIL EKMDGTEELL VKLNREDLLR KQRTFDNGSI PHQIHLGELH
AILRRQEDFY PFLKDNREKI EKILTFRIPY YVGPLARGNS RFAWMTRKSE ETITPWNFEE VVDKGASAQS
FIERMTNFDK NLPNEKVLPK HSLLYEYFTV YNELTKVKYV TEGMRKPAFL SGEQKKAIVD LLFKTNRKVT
VKQLKEDYFK KIECFDSVEI SGVEDRFNAS LGTYHDLLKI IKDKDFLDNE ENEDILEDIV LTLTLFEDRE
MIEERLKTYA HLFDDKVMKQ LKRRRYTGWG RLSRKLINGI RDKQSGKTIL DFLKSDGFAN RNFMQLIHDD
SLTFKEDIQK AQVSGQGDSL HEHIANLAGS PAIKKGILQT VKVVDELVKV MGRHKPENIV IEMARENQTT -continued

```
QKGQKNSRER MKRIEEGIKE LGSQILKEHP VENTQLQNEK LYLYYLQNGR DMYVDQELDI NRLSDYDVDA

IVPQSFLKDD SIDNKVLTRS DKNRGKSDNV PSEEVVKKMK NYWRQLLNAK LITQRKFDNL TKAERGGLSE

LDKAGFIKRQ LVETRQITKH VAQILDSRMN TKYDENDKLI REVKVITLKS KLVSDFRKDF QFYKVREINN

YHHAHDAYLN AVVGTALIKK YPKLESEFVY GDYKVYDVRK MIAKSEQEIG KATAKYFFYS NIMNFFKTEI

TLANGEIRKR PLIETNGETG EIVWDKGRDF ATVRKVLSMP QVNIVKKTEV QTGGFSKESI LPKRNSDKLI

ARKKDWDPKK YGGFDSPTVA YSVLVVAKVE KGKSKKLKSV KELLGITIME RSSFEKNPID FLEAKGYKEV

KKDLIIKLPK YSLFELENGR KRMLASAGEL QKGNELALPS KYVNFLYLAS HYEKLKGSPE DNEQKQLFVE

QHKHYLDEII EQISEFSKRV ILADANLDKV LSAYNKHRDK PIREQAENII HLFTLTNLGA PAAKFYFDTT

IDRKRYTSTK EVLDATLIHQ SITGLYETRI DLSQLGGD
```

(SEQ ID NO: 17)
GAAGTTACTATTCCGAAGTTCCTATTCTCTAGAAAGTATAGGAACTTC (SEQ ID NO: 18)
GAAGTTACTATTCCGAAGTTCCTATTCTCTAGATAGTATAGGAACTTC (SEQ ID NO: 19)
GAAGTTACTATTCCGAAGTTCCTATTCTCTACTTAGTATAGGAACTTC

NUMBERED EMBODIMENTS

1. A cell comprising:
   a first control element operably linked to a sequence encoding an exogenous therapeutic polypeptide;
   a second control element operably linked to a sequence encoding a repressor polypeptide; and
   optionally, a third control element operably linked to a sequence encoding one or more (e.g., 1, 2, 3, 4, 5, 6, 7, 8, 9, 10 or more) gRNAs;
   wherein:
   i) the second control element has a first level of activity under a first condition and a second level of activity under a second condition; or
   ii) the third control element has a first level of activity under a first condition and a second level of activity under a second condition, and
   wherein in the presence of the second condition, the expression of the therapeutic polypeptide is modulated.

2. A cell comprising:
   a first control element operably linked to an insertion site;
   a second control element operably linked to a sequence encoding a repressor polypeptide; and
   optionally a third control element operably linked to a sequence encoding one or more (e.g., 1, 2, 3, 4, 5, 6, 7, 8, 9, 10 or more) gRNAs;
   wherein:
   i) the second control element has a first level of activity under a first condition and a second level of activity under a second condition; or
   ii) the third control element has a first level of activity under a first condition and a second level of activity under a second condition,
   wherein the insertion site is suitable for insertion of a sequence encoding an exogenous therapeutic polypeptide, and
   in the presence of the second condition, the expression of the therapeutic polypeptide is modulated.

3. The cell of either of paragraphs 1 or 2, wherein the modulation is reversible.

4. The cell of either of paragraphs 1 or 2, wherein the modulation is irreversible.

5. The cell of any preceding paragraph, wherein the second control element has an $N^{th}$ level of activity under an $N^{th}$ condition, wherein N is 3, 4, 5, 6, 7, 8, 9, or 10, and in the presence of the $N^{th}$ condition, the expression of the therapeutic polypeptide is modulated relative to the expression of the therapeutic polypeptide under previous conditions.

6. The cell of any preceding paragraph, wherein the third control element has an $N^{th}$ level of activity under an $N^{th}$ condition, wherein N is 3, 4, 5, 6, 7, 8, 9, or 10, and in the presence of the $N^{th}$ condition, the expression of the therapeutic polypeptide is modulated relative to the expression of the therapeutic polypeptide under previous conditions.

7. The cell of any preceding paragraph, wherein the first control element and sequence encoding an exogenous therapeutic polypeptide are disposed on a first nucleic acid and the second control element and sequence encoding a repressor polypeptide are disposed on a second nucleic acid.

8. The cell of paragraph 7, wherein the third control element and sequence encoding one or more gRNAs are disposed on the first nucleic acid.

9. The cell of paragraph 7, wherein the third control element and sequence encoding one or more gRNAs are disposed on the second nucleic acid.

10. The cell of paragraph 7, wherein the third control element and sequence encoding one or more gRNAs are disposed on a third nucleic acid.

11. The cell of any of paragraphs 1-6, wherein the first control element, the sequence encoding an exogenous therapeutic polypeptide, the second control element, and the sequence encoding a repressor polypeptide are disposed on the same nucleic acid.

12. The cell of paragraph 11, wherein the third control element and sequence encoding one or more gRNAs are disposed on the same nucleic acid as the first control element, the sequence encoding an exogenous therapeutic polypeptide, the second control element, and the sequence encoding a repressor polypeptide.

13. The cell of paragraph 11, wherein the third control element and sequence encoding one or more gRNAs are disposed on a separate nucleic acid from the first control element, the sequence encoding an exogenous therapeutic polypeptide, the second control element, and the sequence encoding a repressor polypeptide.

14. The cell of any of paragraphs 7-13, wherein one or more nucleic acids is comprised within a vector suitable for stable expression, e.g., a plasmid.

15. The cell of any of paragraphs 7-13, wherein one or more nucleic acids is comprised within a vector suitable for transient expression.

16. The cell of either paragraph 14 or 15, wherein one or more nucleic acids are comprised within the same vector.

17. The cell of either paragraph 14 or 15, wherein each nucleic acid is comprised on a different vector.

18. The cell of any of paragraphs 7-13, wherein one or more nucleic acids are comprised within a single chromosome.

19. The cell of any of paragraphs 7-13, wherein each nucleic acid is comprised within a different chromosome.

20. The cell of any of paragraphs 7-10, wherein the first nucleic acid is comprised within a vector and the second nucleic acid is comprised within a chromosome.

21. The cell of any of paragraphs 7-10, wherein the first nucleic acid is comprised within a chromosome and the second nucleic acid is comprised within a vector.

22. The cell of paragraph 10, wherein the first nucleic acid is comprised within a vector, the second nucleic acid is comprised within a chromosome, and the third nucleic acid is comprised within a vector.

23. The cell of paragraph 10, wherein the first nucleic acid is comprised within a chromosome, the second nucleic acid is comprised within a vector, and the third nucleic acid is comprised within a vector.

24. The cell of paragraph 10, wherein the first nucleic acid is comprised within a chromosome, the second nucleic acid is comprised within a chromosome, and the third nucleic acid is comprised within a chromosome.

25. The cell of paragraph 10, wherein the first nucleic acid is comprised within a chromosome, the second nucleic acid is comprised within a vector, and the third nucleic acid is comprised within a chromosome.

26. The cell of any preceding paragraph, wherein a stress response induces expression of the repressor polypeptide from the second control element or the third control element.

27. The cell of any preceding paragraph, wherein the repressor polypeptide inhibits expression of the therapeutic polypeptide.

28. The cell of any preceding paragraph, wherein the first control element is responsive to the repressor polypeptide.

29. The cell of any preceding paragraph, wherein the first control element comprises a first promoter element, and the first promoter element, in the absence of repressor polypeptide, has one of the following properties:
  a) it is constitutive;
  b) it is regulated; or
  c) it has a first level of expression at a first stage of growth of the cell and a second level of expression at a second stage of growth.

30. The cell of any preceding paragraph, wherein the first promoter element, in the absence of repressor polypeptide, is constitutive.

31. The cell of any preceding paragraph, wherein the first promoter element is selected from Table 5.

32. The cell of any preceding paragraph, wherein the therapeutic polypeptide comprises:
  a fusion protein;
  a multi-domain polypeptide;
  a bispecific antibody molecule;
  a multispecific antibody molecule;
  a multispecific molecule; and
  a molecule comprising a ligand and an antibody molecule.

33. The cell of any preceding paragraph, wherein the therapeutic polypeptide is selected from Tables 1-4.

34. The cell of any preceding paragraph, wherein the second control element or the third control element is selected from Tables 5 or 6, or comprises a promoter that comprises a sequence with 0, 1, 2, or 3 base substitutions as compared to a sequence selected from Tables 5 or 6.

35. The cell of paragraph 34, wherein the third control element is selected from Table 6 and the second control element is selected from Table 5.

36. The cell of paragraph 34, wherein the third control element is selected from Table 5 and the second control element is selected from Table 6.

37. The cell of any of paragraphs 1-34, wherein the second control element comprises a second promoter element, and the second promoter element is constitutive, and wherein the third control element comprises a third promoter element which has a first level of activity under a first condition and a second level of activity under a second condition.

38. The cell of any of paragraphs 1-34, wherein the second control element comprises a second promoter element which has a first level of activity under a first condition and a second level of activity under a second condition, and wherein the third control element comprises a third promoter element, and the third promoter element is constitutive.

39. The cell of any of paragraphs 1-38, wherein the second control element or third control element comprises one or more heat shock elements (HSEs), cAMP response elements (CREs), antioxidant response elements (AREs), or endoplasmic reticulum response elements (ERSEs).

40. The cell of any of paragraphs 1-38, wherein the second control element or third control element is modulated by an element of the heat shock response or the unfolded protein response (UPR).

41. The cell of any of paragraphs 1-38, wherein the second control element or third control element is modulated by accumulation of misfolded protein.

42. The cell of any of paragraphs 1-38, wherein the second control element or third control element comprises an Xbp1 responsive promoter element.

43. The cell of any of paragraphs 1-38, wherein the second control element or third control element comprises a Grp78 promoter element.

44. The cell of any of paragraphs 1-38, wherein the second control element or third control element comprises an ATF6 responsive promoter element, an ATF4 responsive promoter element, an NRF2 responsive promoter element, or an Hsf1 responsive promoter element.

45. The cell of any preceding paragraph, wherein the repressor polypeptide results in a reduction in the activity, level or expression of the exogenous therapeutic polypeptide.

46. The cell of any preceding paragraph, wherein the repressor polypeptide specifically binds a target nucleic acid sequence.

47. The cell of any of paragraphs 1-46, wherein the repressor polypeptide specifically binds a control element.

48. The cell of any of paragraphs 1-46, wherein the repressor polypeptide specifically binds a promoter.

49. The cell of any preceding paragraph, wherein the repressor polypeptide results in a reduction in the transcription of the exogenous therapeutic polypeptide.

50. The cell of any preceding paragraph, wherein the repressor polypeptide binds to the nucleic acid encoding the exogenous therapeutic polypeptide or to the first promoter which is operably linked to the nucleic acid encoding the exogenous therapeutic polypeptide.

51. The cell of any preceding paragraph, wherein the repressor polypeptide reduces the translation of the exogenous therapeutic polypeptide.

52. The cell of any preceding paragraph, wherein the repressor polypeptide comprises a Cas9 molecule.

53. The cell of any preceding paragraph, wherein the repressor polypeptide comprises a Cas9 molecule with a modified cleavage activity as compared to a naturally occurring Cas9.

54. The cell of any preceding paragraph, wherein the repressor polypeptide comprises a Cas9 molecule lacking cleavage activity in one or both of the HNH and RuvC domains.

55. The cell of any preceding paragraph, wherein the repressor polypeptide comprises a dCas9 molecule.

56. The cell of any preceding paragraph, wherein the repressor polypeptide comprises a Cas9 molecule that further comprises a heterologous repressor domain that enhances repression of the exogenous therapeutic polypeptide.

57. The cell of paragraph 56, wherein the heterologous repressor domain is selected from the group consisting of: the KRAB (Krupel-associated box) domain of Kox1, the CS (chromoshadow) domain of HP1α, the WPRW domain of Hes1, and four concatenated copies of the mSin3 interaction domain (SID4X).

58. The cell of any of paragraphs 52-57, wherein the Cas9 molecule, when complexed with a gRNA, binds to a target nucleic acid in a sequence specific manner.

59. The cell of any of paragraphs 52-58, wherein the Cas9 molecule, when complexed with a gRNA, binds to non-translated sequence.

60. The cell of any of paragraphs 52-59, wherein the Cas9 molecule:gRNA complex binds to the first control element.

61. The cell of any of paragraphs 52-60, wherein the Cas9 molecule:gRNA complex binds to the sequence encoding the exogenous therapeutic polypeptide.

62. The cell of any preceding paragraph, wherein the cell further comprises an $N^{th}$ sequence encoding an $N^{th}$ gRNA operably linked to a third control element, wherein N is 2, 3, 4, 5, 6, 7, 8, 9, or 10.

63. The cell of any preceding paragraph, wherein the third control element is a further copy of the second control element.

64. The cell of any of paragraphs 1-62, wherein the third control element is a further copy of the first control element.

65. The cell of any of paragraphs 1-63, wherein the third control element has a first level of activity under a first condition and a second level of activity under a second condition, and in the presence of the second condition, the expression of the gRNA is modulated.

66. The cell of any preceding paragraph, wherein the third control element has one of the following properties:
   a) it is constitutive;
   b) it is regulated; or
   c) it has a first level of expression at a first stage of growth of the cell and a second level of expression at a second stage of growth.

67. The cell of any preceding paragraph, wherein the second level of activity is greater than the first level of activity.

68. The cell of any preceding paragraph, wherein the first condition is a first level of stress and the second condition is a second level of stress.

69. The cell of any preceding paragraph, wherein the first condition is a first level of unfolded or misfolded polypeptide and the second condition is a second level of unfolded or misfolded polypeptide.

70. The cell of any preceding paragraph, wherein the first condition is a first level of folded exogenous therapeutic polypeptide and the second condition is a second level of folded exogenous therapeutic polypeptide.

71. The cell of any preceding paragraph, wherein the first condition is a first level of unfolded or misfolded polypeptide in the cytosol and the second condition is a second level of unfolded or misfolded polypeptide in the cytosol.

72. The cell of any preceding paragraph, wherein the first condition is a first level of unfolded or misfolded polypeptide in the endoplasmic reticulum (ER) and the second condition is a second level of unfolded or misfolded polypeptide in the ER.

73. The cell of any preceding paragraph, wherein the first condition/second condition pair is selected from the group consisting of:
   a first level of protein aggregation and a second level of protein aggregation;
   a first level of a first glycosylation pattern on the exogenous therapeutic polypeptide and a second level of the first glycosylation pattern on the exogenous therapeutic polypeptide;
   a level of a first glycosylation pattern on the exogenous therapeutic polypeptide and a level of a second glycosylation pattern on the exogenous therapeutic polypeptide;
   a first level of cell viability and a second level of cell viability;
   a first level of activation of the heat shock response (HSR) and a second level of activation of the HSR;
   a first level of activation of the unfolded protein response (UPR) and a second level of activation of the UPR;
   a first level of free ER chaperone and a second level of free ER chaperone;
   a first temperature and a second temperature;
   a first level of oxidative stress and a second level of oxidative stress;
   a first level of ER $Ca^{+2}$ and a second level of ER $Ca^{+2}$;
   a first ER oxidative state and a second ER oxidative state;
   a first cellular energy level and a second cellular energy level;
   a first ATP level and a second ATP level;
   a first glucose level and a second glucose level;
   a first level of activated Hsf1 polypeptide and a second level of activated Hsf1 polypeptide;
   a first level of phosphorylated, trimeric Hsf1 polypeptide and a second level of phosphorylated, trimeric Hsf1 polypeptide;
   a first level of active Xbp1 polypeptide and a second level of activated Xbp1 polypeptide;
   a first level of ATF4 polypeptide and a second level of ATF4 polypeptide;
   a first level of NRF2 polypeptide and a second level of NRF2 polypeptide; and
   a first level of ATF6 polypeptide and a second level of ATF6 polypeptide.

74. The cell of any preceding paragraph, wherein a stress response induces expression of the repressor polypeptide, wherein the repressor polypeptide inhibits expression of the therapeutic polypeptide.

75. The cell of any preceding paragraph, wherein at the second condition, expression of the exogenous therapeutic polypeptide is reduced by at least 5%, 10%, 15%, 20%, 30%, 40%, 50%, 60%, 70%, 80%, 90%, or 100% compared to expression at the first condition.

76. A kit for expression of a therapeutic polypeptide comprising a cell of any preceding paragraph.

77. A nucleic acid comprising:
  a first control element operably linked to a sequence encoding an exogenous therapeutic polypeptide;
  a second control element operably linked to a sequence encoding a repressor polypeptide; and
  optionally, a third control element operably linked to a sequence encoding one or more (e.g., 1, 2, 3, 4, 5, 6, 7, 8, 9, 10 or more) gRNAs;
  wherein:
    i) the second control element has a first level of activity under a first condition and a second level of activity under a second condition; or
    ii) the third control element has a first level of activity under a first condition and a second level of activity under a second condition, and
  wherein in the presence of the second condition, the expression of the therapeutic polypeptide is modulated.

78. A nucleic acid comprising:
  a first control element operably linked to an insertion site;
  a second control element operably linked to a sequence encoding a repressor polypeptide; and
  optionally, a third control element operably linked to a sequence encoding one or more (e.g., 1, 2, 3, 4, 5, 6, 7, 8, 9, 10 or more) gRNAs;
  wherein:
    i) the second control element has a first level of activity under a first condition and a second level of activity under a second condition; or
    ii) the third control element has a first level of activity under a first condition and a second level of activity under a second condition,
  wherein the insertion site is suitable for insertion of a sequence encoding an exogenous therapeutic polypeptide, and
  in the presence of the second condition, the expression of the therapeutic polypeptide is modulated.

79. The nucleic acid of either paragraph 77 or 78, wherein the first control element and sequence encoding an exogenous therapeutic polypeptide are comprised on a first nucleic acid and the second control element and sequence encoding a repressor polypeptide are comprised on a second nucleic acid.

80. The nucleic acid of paragraph 79, wherein the third control element and sequence encoding one or more gRNAs are disposed on the first nucleic acid.

81. The nucleic acid of paragraph 79, wherein the third control element and sequence encoding one or more gRNAs are disposed on the second nucleic acid.

82. The nucleic acid of paragraph 79, wherein the third control element and sequence encoding one or more gRNAs are disposed on a third nucleic acid.

83. The nucleic acid of either paragraph 77 or 78, wherein the first control element, the sequence encoding an exogenous therapeutic polypeptide, the second control element, and the sequence encoding a repressor polypeptide are comprised on the same nucleic acid.

84. The nucleic acid of paragraph 83, wherein the third control element and sequence encoding one or more gRNAs are disposed on the same nucleic acid as the first control element, the sequence encoding an exogenous therapeutic polypeptide, the second control element, and the sequence encoding a repressor polypeptide.

85. The nucleic acid of paragraph 83, wherein the third control element and sequence encoding one or more gRNAs are disposed on a separate nucleic acid from the first control element, the sequence encoding an exogenous therapeutic polypeptide, the second control element, and the sequence encoding a repressor polypeptide.

86. The nucleic acid of any of paragraphs 79-85, wherein one or more nucleic acids is comprised within a vector suitable for stable expression.

87. The nucleic acid of any of paragraphs 79-85, wherein one or more nucleic acids is comprised within a vector suitable for transient expression.

88. The nucleic acid of either paragraph 86 or 87, wherein one or more nucleic acids are comprised within the same vector.

89. The nucleic acid of either paragraph 86 or 87, wherein each nucleic acid is comprised on a different vector.

90. The nucleic acid of any of paragraphs 79-85, wherein one or more nucleic acid is comprised within a single chromosome.

91. The nucleic acid of any of paragraphs 79-85, wherein each nucleic acid is comprised within a different chromosome.

92. The nucleic acid of any of paragraphs 79-82, wherein the first nucleic acid is comprised within a vector and the second nucleic acid is comprised within a chromosome.

93. The nucleic acid of any of paragraphs 79-82, wherein the first nucleic acid is comprised within a chromosome and the second nucleic acid is comprised within a vector.

94. The nucleic acid of paragraph 82, wherein the first nucleic acid is comprised within a vector, the second nucleic acid is comprised within a chromosome, and the third nucleic acid is comprised within a vector.

95. The nucleic acid of paragraph 82, wherein the first nucleic acid is comprised within a chromosome, the second nucleic acid is comprised within a vector, and the third nucleic acid is comprised within a vector.

96. The nucleic acid of paragraph 82, wherein the first nucleic acid is comprised within a vector, the second nucleic acid is comprised within a chromosome, and the third nucleic acid is comprised within a chromosome.

97. The nucleic acid of paragraph 82, wherein the first nucleic acid is comprised within a chromosome, the second nucleic acid is comprised within a vector, and the third nucleic acid is comprised within a chromosome.

98. A kit for expression of a therapeutic polypeptide comprising a nucleic acid of any of paragraphs 77-97.

99. A method of making a cell of any of paragraphs 1-75, comprising:
  a) forming or providing in the cell, a first nucleic acid sequence that encodes a first control element operably linked to a sequence encoding an exogenous therapeutic polypeptide;
  b) forming or providing in the cell, a second nucleic acid that encodes a second control element operably linked to a sequence encoding a repressor polypeptide; and
  c) optionally forming or providing in the cell, a third nucleic acid that encodes a third control element operably linked to a sequence encoding one or more (e.g., 1, 2, 3, 4, 5, 6, 7, 8, 9, 10 or more) gRNAs,
  wherein:
    i) the second control element has a first level of activity under a first condition and a second level of activity under a second condition; or
    ii) the third control element has a first level of activity under a first condition and a second level of activity under a second condition, and wherein in the presence of the second condition, the expression of the therapeutic polypeptide is modulated, thereby making the cell.

100. The method of paragraph 99, wherein forming or providing in the cell a first nucleic acid sequence comprises introducing the first nucleic acid sequence into the cell.

101. The method of paragraph 100, wherein introducing the first nucleic acid sequence into the cell comprises a technique selected from: transiently transfecting, stably transfecting, transducing, and transforming.

102. The method of any of paragraphs 99-101, wherein forming or providing in the cell a second nucleic acid sequence comprises introducing the second nucleic acid sequence into the cell.

103. The method of paragraph 102, wherein introducing the second nucleic acid sequence into the cell comprises a technique selected from: transiently transfecting, stably transfecting, transducing, and transforming.

104. The method of any of paragraphs 99-102, wherein forming or providing in the cell a third nucleic acid sequence comprises introducing the third nucleic acid sequence into the cell.

105. The method of paragraph 104, wherein introducing the third nucleic acid sequence into the cell comprises a technique selected from: transiently transfecting, stably transfecting, transducing, and transforming.

106. The method of paragraph 99, wherein (a), (b), and optionally (c) comprise simultaneously introducing the first, second, and third nucleic acids into the cell.

107. The method of paragraph 99, wherein (a), (b), and optionally (c) occur sequentially.

108. The method of paragraph 99, wherein forming or providing in the cell a first nucleic acid sequence comprises inserting, in the cell, the sequence encoding an exogenous therapeutic polypeptide into a suitable insertion site operably linked to the first control element.

109. The method of paragraph 99, wherein forming or providing in the cell a second nucleic acid sequence comprises inserting, in the cell, the sequence encoding a repressor polypeptide into a suitable insertion site operably linked to the second control element.

110. The method of paragraph 99, wherein forming or providing in the cell a third nucleic acid sequence comprises inserting, in the cell, the sequence encoding one or more gRNAs into a suitable insertion site operably linked to the third control element.

111. A method of making a therapeutic polypeptide, comprising:
 a) acquiring a cell of any of paragraphs 1-75, and
 b) culturing the cell under conditions that allow for making of the therapeutic polypeptide,
 thereby making the therapeutic polypeptide.

112. A method of making a therapeutic polypeptide, comprising:
 a) acquiring a cell;
 b) forming or providing in the cell, a first nucleic acid sequence that encodes a first control element operably linked to a sequence encoding an exogenous therapeutic polypeptide;
 c) forming or providing in the cell, a second nucleic acid that encodes a second control element operably linked to a sequence encoding a repressor polypeptide; and
 d) optionally forming or providing in the cell, a third nucleic acid that encodes a third control element operably linked to a sequence encoding one or more (e.g., 1, 2, 3, 4, 5, 6, 7, 8, 9, 10 or more) gRNAs,
 wherein:
  i) the second control element has a first level of activity under a first condition and a second level of activity under a second condition; or
  ii) the third control element has a first level of activity under a first condition and a second level of activity under a second condition, and
 wherein in the presence of the second condition, the expression of the therapeutic polypeptide is modulated, and
 e) culturing the cell under conditions that allow for making of the therapeutic polypeptide,
 thereby making the therapeutic polypeptide.

113. A reaction mixture comprising:
 a cell of any of paragraphs 1-75, and
 a culture medium;
 wherein the culture medium is suitable for expressing the therapeutic polypeptide.

114. A genetic control circuit comprising:
 a first control element operably linked to a sequence encoding an exogenous therapeutic polypeptide;
 a second control element operably linked to a sequence encoding a repressor polypeptide; and
 optionally, a third control element operably linked to a sequence encoding one or more gRNAs,
 wherein:
  i) the second control element has a first level of activity under a first condition and a second level of activity under a second condition; or
  ii) the third control element has a first level of activity under a first condition and a second level of activity under a second condition, and
 wherein in the presence of the second condition, the expression of the therapeutic polypeptide is modulated.

115. The genetic control circuit of paragraph 114, wherein the modulation is reversible.

116. The genetic control circuit of either of paragraphs 114 or 115, wherein a stress response induces expression of the repressor polypeptide from the second control element.

117. The genetic control circuit of any of paragraphs 114-116, wherein the repressor polypeptide inhibits expression of the therapeutic polypeptide.

118. The genetic control circuit of any of paragraphs 114-117, wherein the first control element is responsive to the repressor polypeptide.

119. The genetic control circuit of any of paragraphs 114-118, wherein the therapeutic polypeptide comprises:
 a fusion protein;
 a multi-domain polypeptide
 a bispecific antibody molecule;
 a multispecific antibody molecule;
 a multispecific molecule; and
 a molecule comprising a ligand and an antibody molecule.

120. The genetic control circuit of any of paragraphs 114-119, wherein the therapeutic polypeptide is selected from Tables 1-4.

121. The genetic control circuit of any of paragraphs 114-120, wherein the second control element or the third control element is selected from Tables 5 or 6.

122. The genetic control circuit of any of paragraphs 114-120, wherein the third control element is selected from Table 6 and the second control element is selected from Table 5.

123. The genetic control circuit of any of paragraphs 114-120, wherein the third control element is selected from Table 5 and the second control element is selected from Table 6.

124. The genetic control circuit of any of paragraphs 114-120, wherein the second control element comprises a second promoter element, and the second promoter element is constitutive, and wherein the third control element comprises a third promoter element which has a first level of activity under a first condition and a second level of activity under a second condition.

125. The genetic control circuit of any of paragraphs 114-120, wherein the second control element comprises a second promoter element which has a first level of activity under a first condition and a second level of activity under a second condition, and wherein the third control element comprises a third promoter element, and the third promoter element is constitutive.

126. The genetic control circuit of any of paragraphs 114-121, wherein the third control element is a copy of the first control element.

127. The genetic control circuit of any of paragraphs 114-121, wherein the third control element is a copy of the second control element.

128. The genetic control circuit of any of paragraphs 114-127, wherein the repressor polypeptide results in a reduction in the activity, level, or expression of the exogenous therapeutic polypeptide.

129. A cell comprising:
a first control element selected from Table 5 operably linked to a sequence encoding an exogenous therapeutic polypeptide selected from Tables 1-4;
a second control element selected from Table 6 operably linked to a sequence encoding aCas9 polypeptide; and
one or more gRNA sequences that are constitutively expressed;
wherein, the second control element has a first level of activity under a first condition and a second level of activity under a second condition, and in the presence of the second condition, the expression of the therapeutic polypeptide is modulated.

130. A cell comprising:
a first control element selected from Table 5 operably linked to a sequence encoding an exogenous therapeutic polypeptide selected from Tables 1-4;
a second control element selected from Table 5 operably linked to a sequence encoding aCas9 polypeptide; and
a third control element selected from Table 6 and operably linked to one or more gRNA sequences;
wherein, the third control element has a first level of activity under a first condition and a second level of activity under a second condition, and in the presence of the second condition, the expression of the therapeutic polypeptide is modulated.

131. A plurality of the cells of any one of paragraphs 1-75, 129 or 130, wherein one or more cells comprise the first condition and one or more cells comprise the second condition.

132. The cell, method, nucleic acid, or genetic control circuit of any of paragraphs 1-30, 32-75, 77-97, 99-112, and 114-128, wherein the first control element is an engineered promoter.

133. The cell, method, nucleic acid, or genetic control circuit of any of paragraphs 1-62, 65-75, 77-97, 99-112, 114-121, 124-126, and 128, wherein the third control element is an engineered promoter.

EXEMPLIFICATION

Example 1

Figure 3A:
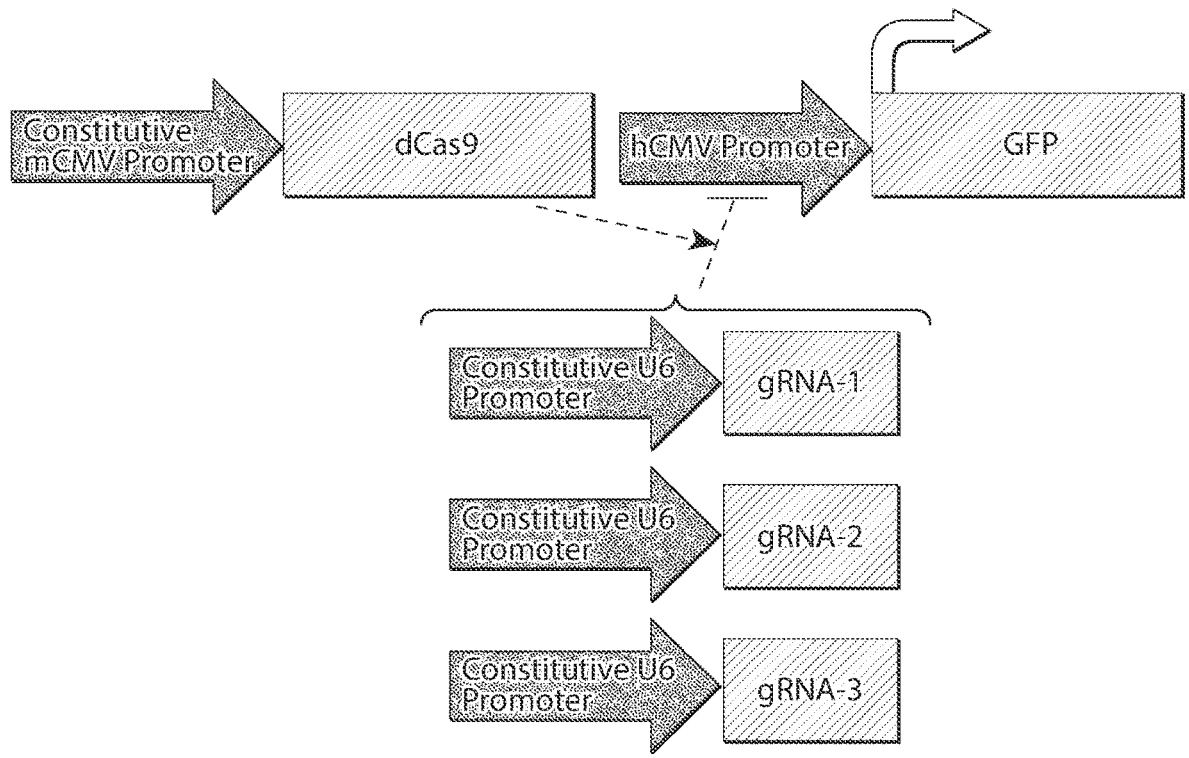
FIG. 3A depicts a genetic control circuit showing GFP transcription driven by a first control element, e.g., a first promoter element, e.g., the hCMV promoter, which is constitutive in the absence of repressor polypeptide, e.g., dCas9, which is controlled from a second control element, e.g, a second promoter element, e.g., a constitutive mCMV promoter. In this example, constitutively expressed dCas9 combines with gRNAs 1, 2, or 3 (specific to hCMV and produced constitutively from U6 promoter) to bind the hCMV promoter and inhibit GFP expression.
Figure 3B:
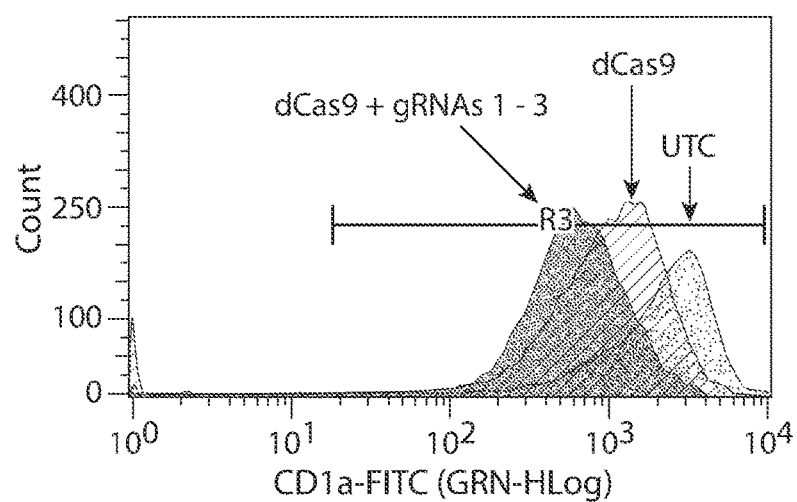
FIG. 3B depicts a flow cytometry histogram showing GFP fluorescence of CHO cells stably expressing hCMV-eGFP, wherein the CHO cells were transfected with 1) an empty expression vector (UTC), 2) an expression vector encoding dCas9, or 3) an expression vector encoding dCas9 and an expression vector encoding three gRNAs with specificity to hCMV.

In the examples to follow, the design principle of the genetic control circuit depicted in FIGS. 1A and 1B is utilized. In this example the principle of using a repressor (i.e. dCas9) to repress expression of a recombinant protein gene (i.e. GFP) was tested using a circuit depicted in FIG. 3A. Here a CHOK1SV-derived GS-KO (Xceed™) cell line stably expressing a recombinant polypeptide gene, GFP, operably linked to a first control element, e.g., first promoter element, hCMV was transiently transfected with either 1) An expression vector encoding a repressor polypeptide, dCas9 operably linked to a constitutive mCMV promoter, only, or 2) An expression vector encoding a repressor polypeptide (dCas9), plus vectors expressing gRNAs 1, 2, and 3, each controlled from separate U6 promoters (FIG. 3A). Four days post transfection the GFP fluorescence was determined by flow cytometry, and it was observed that transfection with dCas9+gRNAs 1 to 3 resulted in a decrease in the population GFP fluorescence compared to cells transfected with dCas9 only, or untransfected control cells (UTC) (FIG. 3B). This demonstrates repression of recombinant polypeptide (GFP) expression using a repressor polypeptide, dCas9, and gRNAs.

Example 2

Figure 4A:
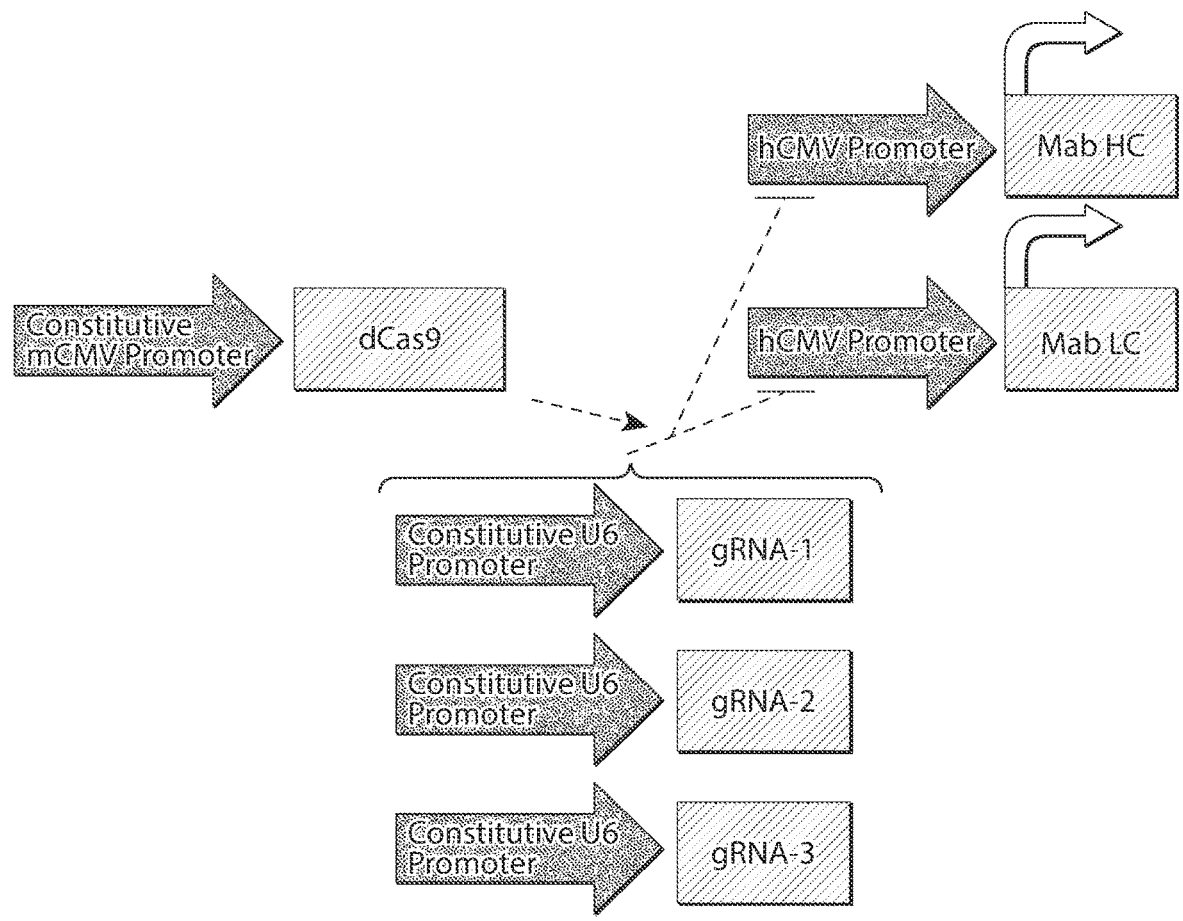
FIG. 4A depicts a genetic control circuit showing Mab HC and Mab LC transcription driven by two separate first control elements, e.g., first promoter elements, e.g., hCMV promoters, which is constitutive in the absence of repressor polypeptide, e.g., dCas9, which is controlled from a second control element, e.g., a second promoter element, e.g. a constitutive mCMV promoter. In this example, constitutively expressed dCas9 combines with gRNAs 1, 2, or 3 (specific to hCMV and produced constitutively from U6 promoter) to bind the hCMV promoter and inhibit Mab HC and Mab LC expression.
Figure 4B:
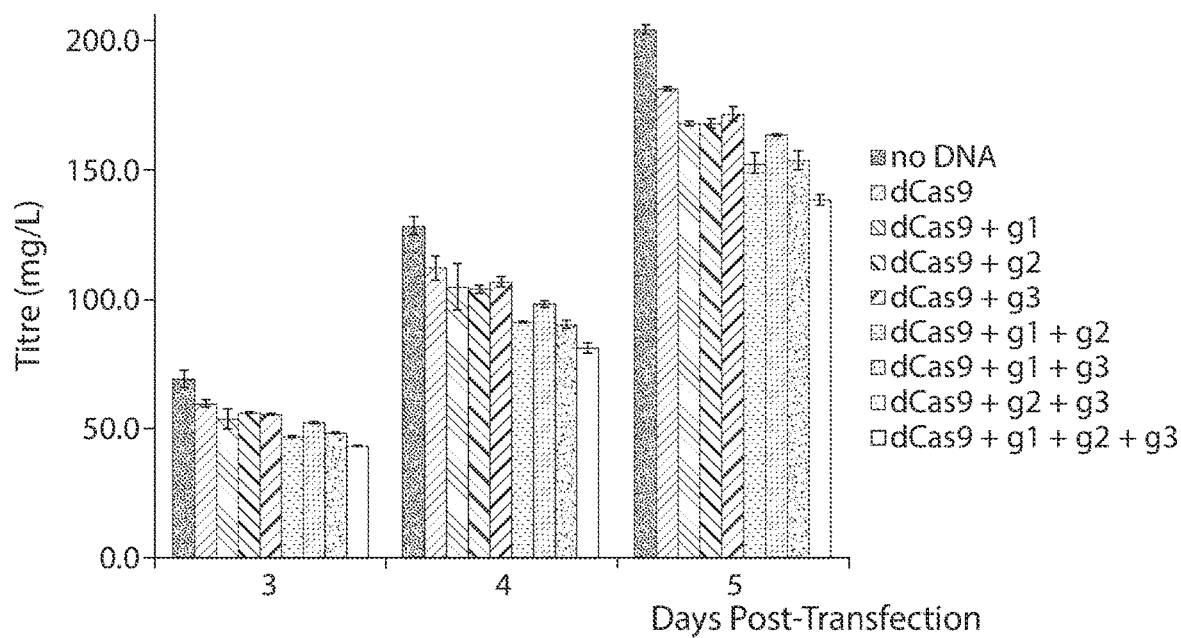
FIG. 4B depicts a graph of hCMV-Mab levels from CHO cells transiently transfected with no DNA, an expression vector encoding dCas9, or expression vectors encoding dCas9 and one, two or three gRNAs with specificity to hCMV at 3, 4, or 5 days post-transfection.

In this example the principle of using a repressor (i.e. dCas9) to repress expression of recombinant monoclonal antibody heavy chain (HC) and light chain (LC) genes were tested using a circuit depicted in FIG. 4A. In this example we demonstrate inhibition of expression of a therapeutic polypeptide, IgG4 Mab cB72.3 operably linked to a first control element, e.g., promoter element, hCMV, by a repressor polypeptide, dCas9 operably linked to a constitutive mCMV promoter. Using a CHO cell line pool stably expressing the IgG4 Mab cB72.3 HC and LC genes each driven by separate hCMV promoters, the ability to down-regulate Mab expression using dCas9 and gRNAs 1 to 3 targeting the hCMV promoters was tested. The pool was transiently transfected with either the dCas9 plasmid only (dCas9), or the dCas9 plasmid+/− the gRNA-encoding plasmids (dCas9+g1−g3. see FIG. 4B), and Mab concentration was determined at days 3, 4, and 5 post-transfection using the Octet Bioanalyser (FIG. 4B). Error bars represent the standard deviation across triplicate transfections. Cells were also transfected with a buffer only as a negative control (No DNA). This demonstrates repression of Mab expression using dCas9 plus gRNAs.

Example 3

Figure 5A:
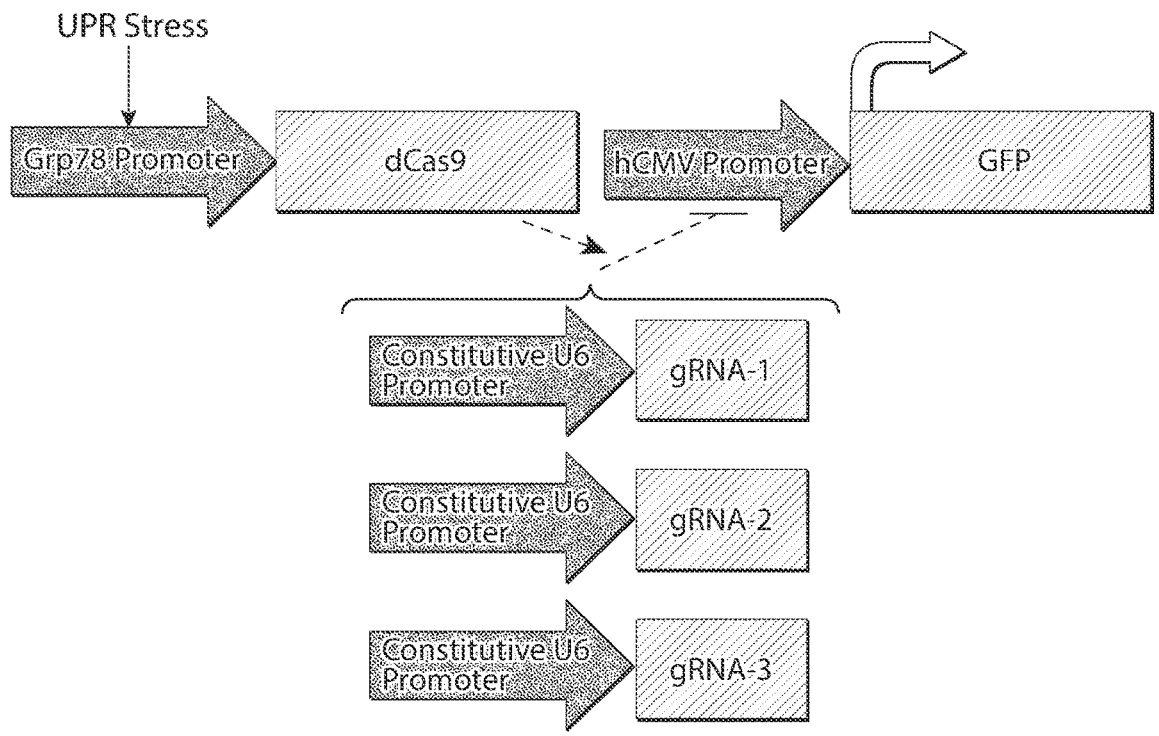
FIG. 5A depicts a genetic control circuit showing GFP transcription driven by a first control element, e.g., a first promoter element, e.g., the hCMV promoter, which is constitutive in the absence of repressor polypeptide, e.g., dCas9, which is controlled from a second control element, e.g, a second promoter element, e.g., an unfolded protein response (UPR) stress induced Grp78 promoter. In this example, UPR stress promotes the expression of dCas9, which combines with gRNAs 1, 2, or 3 (specific to hCMV and produced constitutively from U6 promoter) to bind the hCMV promoter and inhibit GFP expression.
Figure 5B:
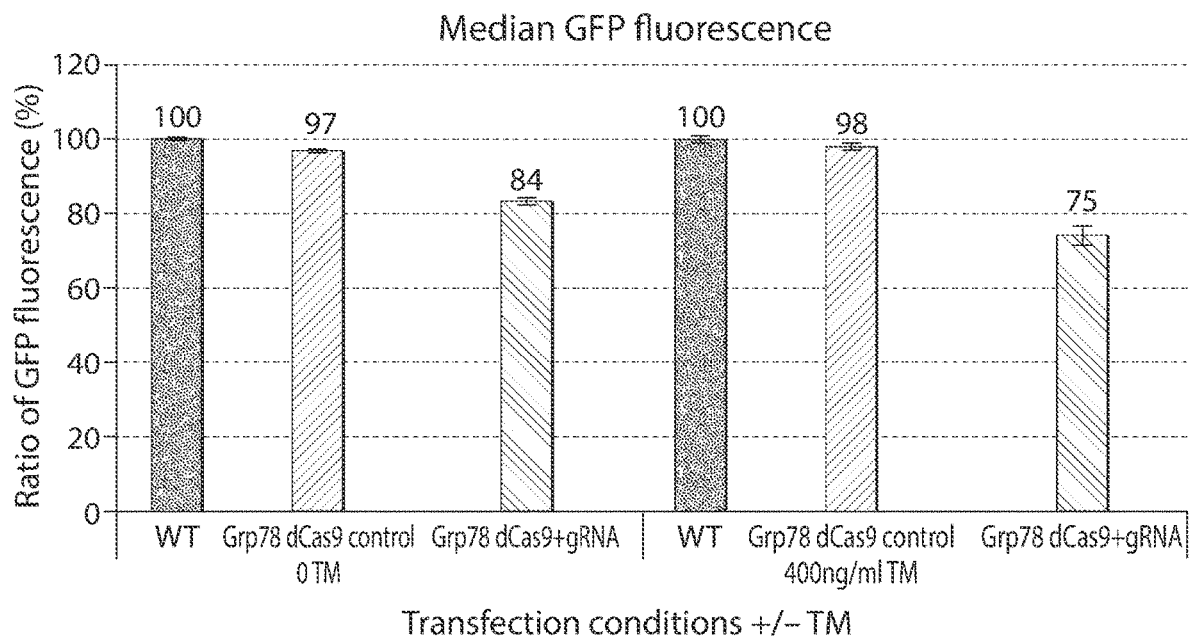
FIG. 5B depicts a graph of flow cytometry data showing GFP fluorescence of CHO cells stably expressing hCMV-eGFP, wherein the CHO cells have been transiently transfected with either 1) empty expression vector (WT), 2) expression vector encoding dCas9 under the Grp78 promoter (Grp78 dCas9 control), or 3) expression vector encoding dCas9 under the Grp78 promoter and an expression vector encoding gRNAs with specificity to the hCMV promoter, and wherein CHO cells were either treated with 400 ng/mL tunicamycin TM or not treated with TM (0 TM).

In this example, the inhibition of expression of a recombinant polypeptide, GFP, using a genetic control circuit depicted in FIG. 5A was demonstrated. CHOK1SV-derived GS-KO (Xceed™) cells stably expressing GFP operably linked to a first control element, e.g., a promoter element, hCMV, were transiently transfected with a set of plasmids; a plasmid containing a sequence encoding a repressor polypeptide, dCas9, operably linked to a second control element, e.g., promoter element, the Grp78 promoter, and plasmids encoding for the expression of gRNAs 1 to 3 each under the control of separate U6 promoters. The Grp78 promoter is activated by the unfolded protein response (UPR), which in this case was activated artificially by addition of tunicamycin (TM) 24 h after transfection. Four days after transient transfection the GFP output was measured by flow cytometry. It can be seen that GFP output was repressed in the cells transfected with both the dCas9 and gRNA plasmids 1 to 3 after 400 ng/mL tunicamycin (TM) treatment (Grp78 dCas9+gRNA) in comparison to cells similarly transfected but not treated with tunicamycin (0 TM), or cells only transfected by dCas9 (Grp78 dCas9 control) (FIG. 5).

Example 4

Figure 2:
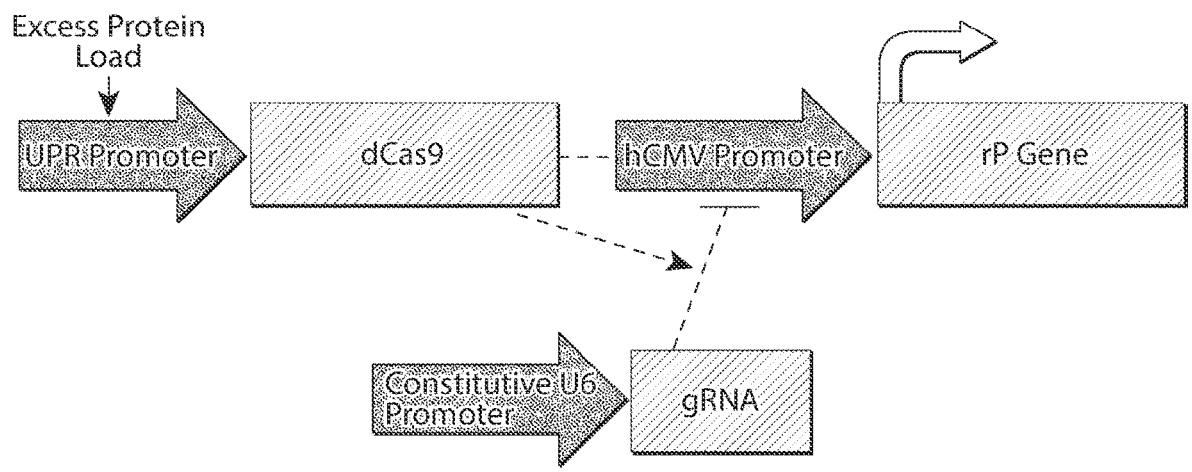
FIG. 2 depicts an example genetic control circuit showing recombinant or therapeutic polypeptide (rP) transcription driven by a first control element, e.g., a first promoter element, e.g., the hCMV promoter, which is constitutive in the absence of repressor polypeptide, e.g., dCas9, which is controlled from a second control element, e.g, a second promoter element, e.g., an unfolded protein response (UPR)-activated promoter. In this example, upon activation of the UPR, which may occur when synthesizing an rP, repressor polypeptide, e.g., dCas9, is produced. In combination with gRNA dCas9 binds to the hCMV promoter and inhibits rP production until the UPR stress response is relieved.
Figure 6A:
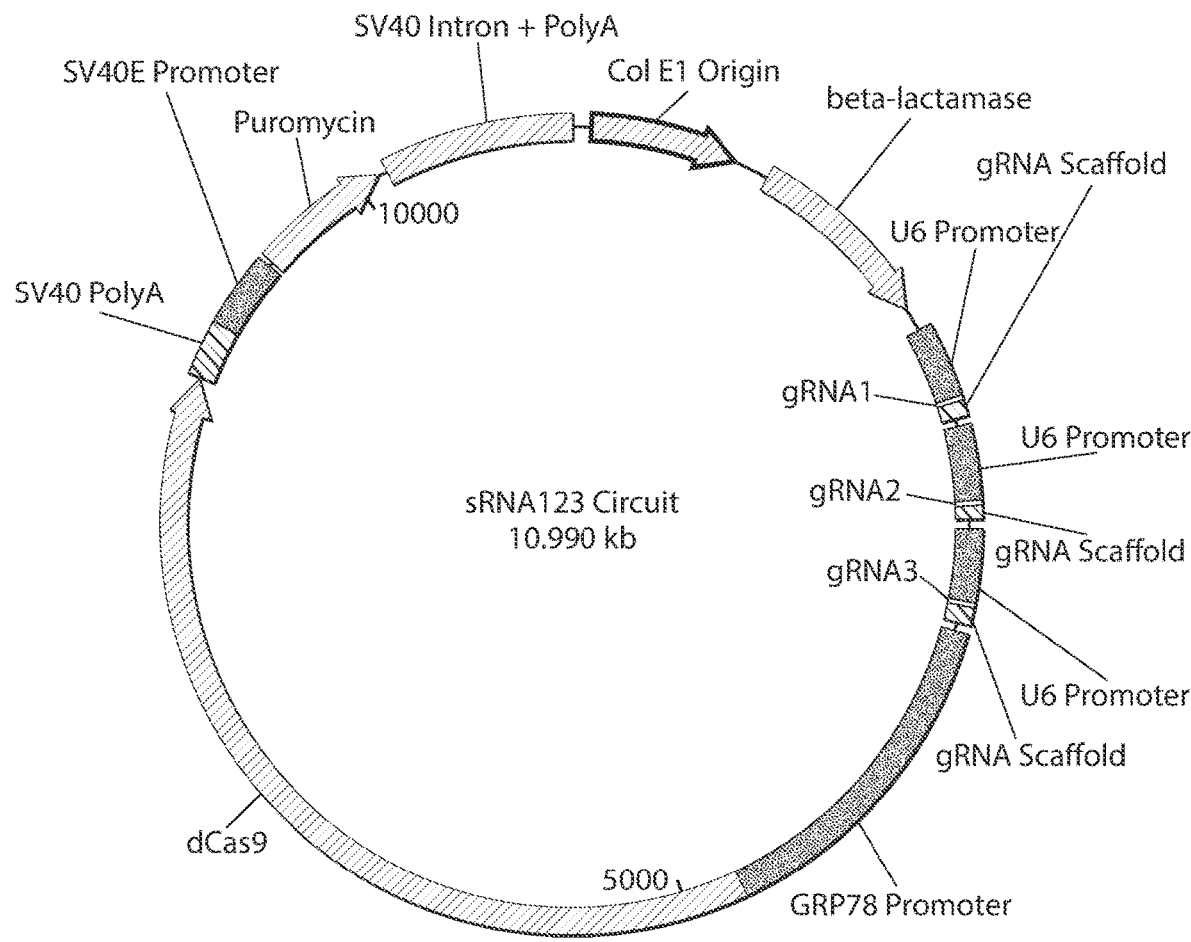
FIGS. 6A-6C show the impact of the genetic control circuit on transient recombinant protein expression in a CHO host cell line.
Figure 6B:
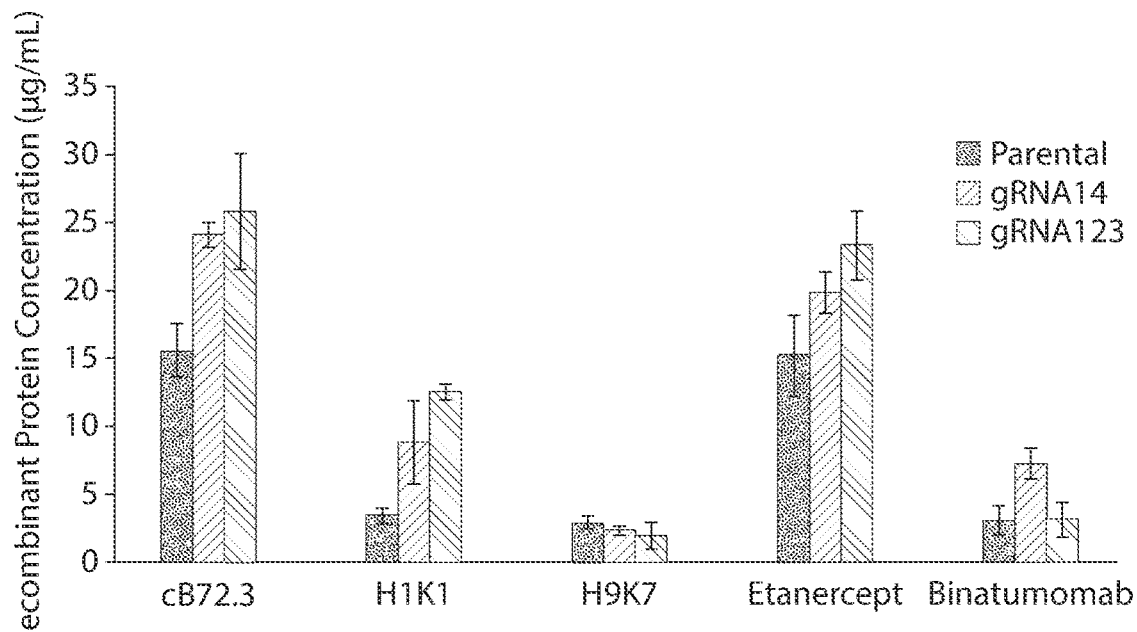
Figure 6C:
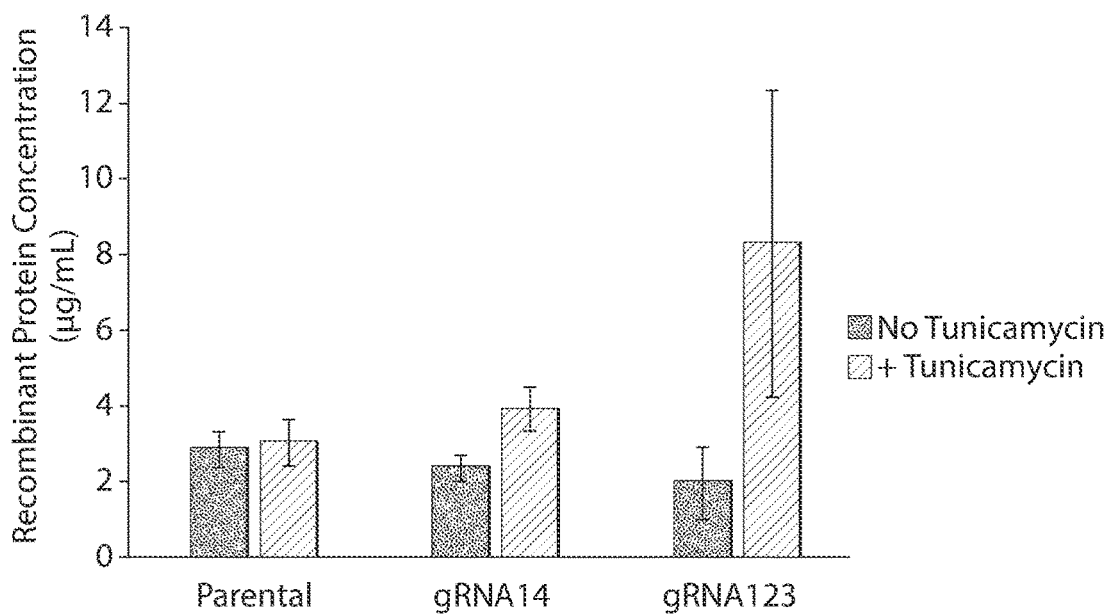

In this example the ability of the genetic control circuit depicted in FIG. 2 to increase the production of several recombinant proteins, including difficult-to-express proteins, is demonstrated. CHOK1SV-derived GS-KO (Xceed™) cells stably expressing the genetic control circuit were constructed using the vector depicted in FIG. 6A. This vector contained the dCas9 gene under the Grp78 promoter, and three gRNA sequences with specificity to the hCMV promoter (gRNAs 1, 2 and 3), each under a separate constitutive U6 promoter. A variant of this vector contained a single gRNA14 sequence in place of the gRNA 1, 2 and 3 sequences and CHOK1SV-derived GS-KO (Xceed™) cells stably expressing the genetic control circuit were constructed using the variant vector as well. The genetic control circuit vectors also contained the puromycin resistance gene (puromycin N-acetyl transferase ('puromycin')) under the SV40 promoter to allow positive selection of cells which had stably incorporated the genetic control circuit after transfection by treatment with the antibiotic puromycin. Stable CHOK1SV-derived GS-KO (Xceed™) pools expressing the genetic control circuits with either the single gRNA14 sequence, or gRNAs 1, 2, and 3, were then transiently transfected with expression vectors encoding for several difficult-to-express recombinant proteins: H1K1 and H9K7 (both highly aggregating Mabs), Etanercept (a complex Fc fusion protein), and blinatumomab (a complex bispecific T-cell engager (BiTE), as well as an IgG4 Mab cB72.3. The recombinant protein concentration produced 6 days after transfection is shown in FIG. 6B, as determined using the Octet Bioanalyser. The results show that for all of the recombinant proteins bar H9K7, at least one of the genetic control circuits was associated with an increase in mean recombinant protein concentration in comparison with the parental CHOK1SV-derived GS-KO (Xceed™) cell line lacking the control circuits. This suggests that the genetic control circuits may increase productivity for some proteins, including complex, difficult to express molecules. To further investigate the ability of the genetic control circuits to increase expression of recombinant proteins, the CHO cells stably expressing the circuit and transiently transfected with the H9K7-encoding vectors were subject to an increased UPR by addition of tunicamycin (TM) (0.1 μg/mL) 24 h post transfection (FIG. 6C). Cells containing the genetic control circuits produced an increased mean concentration of H9K7 at day 6 post transfection when TM was added, whereas the parental CHO host cell line lacking the control circuit showed no effect. This indicates that the genetic control circuit can increase expression and yield of an exogenous difficult-to-express protein in the presence of activated UPR. It also indicates that the genetic control circuit's effect on exogenous protein expression is associated with the UPR.

Figure 7A:
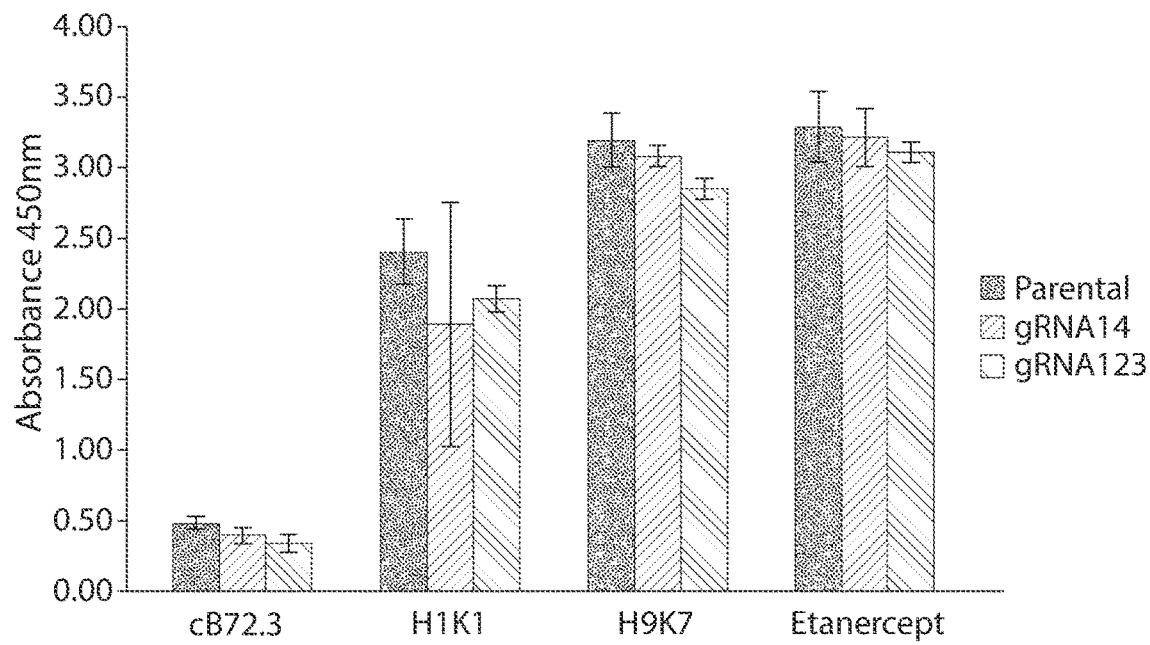
FIGS. 7A and 7B show the levels of recombinant protein aggregation of the proteins synthesised by the stable CHO pools containing the control circuits following transient transfection with expression vectors encoding for several difficult-to-express recombinant proteins, as described in FIGS. 6A-6C. The level of recombinant protein aggregation was determined from the cell culture supernatant samples by oligomer detection assay (ODA), as described in Obrezanova et al. MAbs. 2015; 7(2):352-63. Using this assay a decrease in protein aggregation is represented by a decrease in the absorbance at 450 nm.
Figure 7B:
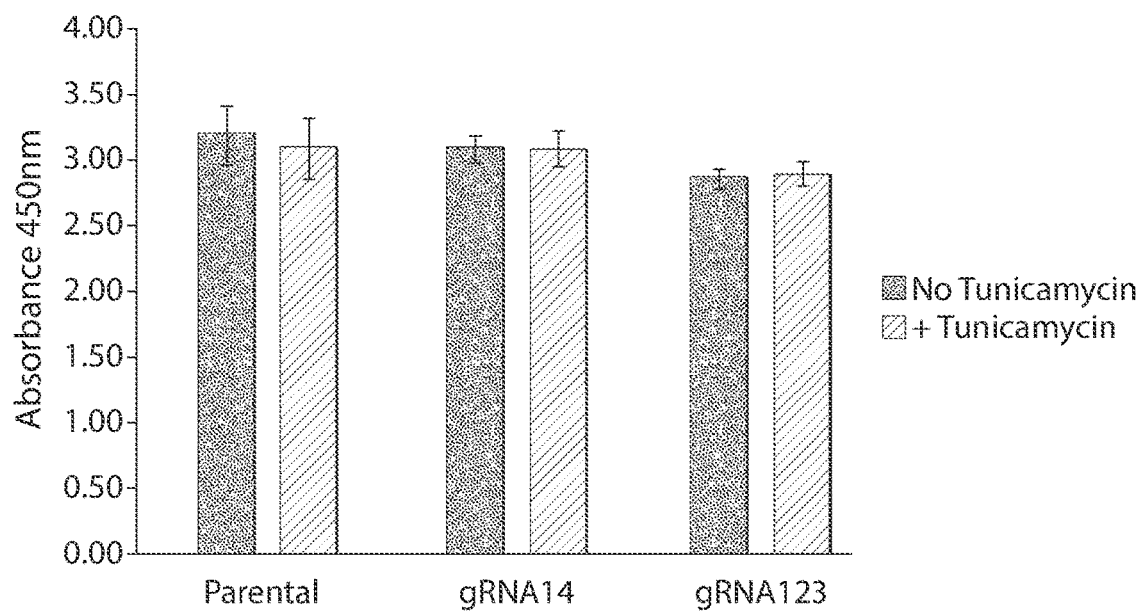

In the set of transfections described above the levels of protein aggregation in the cell culture supernatant were also determined by ODA assay (Obrezanova et al. MAbs. 2015; 7(2):352-63) (FIGS. 7A and 7B). In this assay cB723 is known to display low levels of aggregation, whereas H1K1, H9K7, and Etanercept are known to be highly aggregating in the parental cell line CHOK1SV-derived GS-KO (Xceed™), and therefore to show higher absorbance values at 450 nm (FIG. 7A). The control circuits were not expected to show any substantial benefit on reducing the aggregation of H9K7 and Etanercept as these are known to show high to severe levels of aggregation, and therefore may be beyond the dynamic range of control of the circuit for this parameter. However, H1K1 is known to show slightly lower levels of aggregation by comparison, albeit still high, and may be amenable to improvement (i.e., a reduction in aggregation). Indeed, in this assay both variants of the control circuit were associated with a reduction in mean H1K1 aggregation in comparison to the parental host cell line despite the increase in overall product concentration (compare FIGS. 6B and 7A). In the presence of tunicamycin no improvement (i.e. reduction) in aggregation of H9K7 was observed using the control circuits despite the increases in overall product concentration for the gRNA14 and gRNA 123 variants (compare FIGS. 6C with 7B), suggesting again that the aggregating behaviour of the H9K7 antibody is beyond the dynamic range of influence of the control circuits.

In the set of transfections described above it may be possible to measure other key product quality (PQ) attributes such as N-glycan micro-/macro-heterogeneity (e.g. by UPLC or LC-MS), with an expected improvement in PQ in cells containing the control circuit.

We claim:

1. A cell comprising:
a first control element operably linked to a sequence encoding an exogenous therapeutic polypeptide;
a second control element operably linked to a sequence encoding a repressor polypeptide; and
a third control element operably linked to a sequence encoding one or more gRNAs with homology to the sequence encoding an exogenous therapeutic polypeptide, or with homology to the first control element;
wherein
(i) the repressor polypeptide is a Cas9 molecule;
(ii) the repressor polypeptide in combination with the one or more gRNAs, inhibits expression of the therapeutic polypeptide; and
(iii) the second control element or the third control element is:
(a) an endoplasmic reticulum response element (ERSE);
(b) activated by the unfolded protein response (UPR); or
(c) activated by accumulation of misfolded protein;
and wherein:
i) the second control element or the third control element have a first level of activity under a first condition and a second level of activity under a second condition; or
ii) both the second control element and the third control element have a first level of activity under a first condition and a second level of activity under a second condition, and
wherein the first condition and the second condition are (i) a lower level of unfolded or misfolded polypeptide in the endoplasmic reticulum (ER) and a higher level of unfolded or misfolded polypeptide in the ER, respectively; (ii) a lower level of activation of the unfolded protein response (UPR) and a higher level of activation of the UPR, respectively; or (iii) a lower level of protein aggregation and a higher level of protein aggregation, respectively; and
wherein in the presence of the second condition, the repressor polypeptide in combination with the one or more gRNAs, is expressed and inhibits expression of the therapeutic polypeptide.

2. The cell of claim 1, wherein:
(a) the first control element and sequence encoding an exogenous therapeutic polypeptide are disposed on a first nucleic acid and the second control element and sequence encoding a repressor polypeptide are disposed on a second nucleic acid, wherein:
(i) the third control element and sequence encoding one or more gRNAs are disposed on the first nucleic acid,
(ii) the third control element and sequence encoding one or more gRNAs are disposed on the second nucleic acid, or
(iii) the third control element and sequence encoding one or more gRNAs are disposed on a third nucleic acid; or
(b) the first control element, the sequence encoding an exogenous therapeutic polypeptide, the second control element, and the sequence encoding a repressor polypeptide are disposed on the same nucleic acid, wherein:
(i) the third control element and sequence encoding one or more gRNAs are disposed on the same nucleic acid as the first control element, the sequence encoding an exogenous therapeutic polypeptide, the second control element, and the sequence encoding a repressor polypeptide, or
(ii) the third control element and sequence encoding one or more gRNAs are disposed on a separate nucleic acid from the first control element, the sequence encoding an exogenous therapeutic polypeptide, the second control element, and the sequence encoding a repressor polypeptide.

3. The cell of claim 1, wherein the first control element is selected from cytomegalovirus (CMV) major immediate early promoters, SV40 promoter, Rous sarcoma virus long terminal repeat (RSV-LTR), Moloney murine leukaemia virus (MoMLV) LTR, CHO specific Chinese hamster elongation factor 1-alpha (CHEF1α) promoter, thymidine kinase (TK) promoter, actin promoter, glyceraldehyde 3-phosphate dehydrogenase (GAPDH) promoter, cyclin T1 promoter, RNA polymerase III U3 promoter, cyclophilin promoter, Autographa californica nuclear polyhedrosis virus (AcNPV) P10 promoter, β3-galactosyltransferase 5 (β3GAL-T5) promoter, or CAG promoter.

4. The cell of claim 1, wherein the therapeutic polypeptide comprises:
a fusion protein;
a multi-domain polypeptide;
a bispecific antibody molecule;
a multispecific antibody molecule;
a multispecific molecule; and/or
a molecule comprising a ligand and an antibody molecule.

5. The cell of claim 1, wherein:
(a) the second control element comprises a second promoter element, and the second promoter element is constitutive, and wherein the third control element comprises a third promoter element which has a first level of activity under the first condition and a second level of activity under the second condition, or (b) the second control element comprises a second promoter element which has a first level of activity under the first condition and a second level of activity under the second condition, and wherein the third control element comprises a third promoter element, and the third promoter element is constitutive.

6. The cell of claim 5, wherein the constitutive promoter is selected from:

cytomegalovirus (CMV) major immediate early promoters, SV40 promoter, *Rous sarcoma* virus long terminal repeat (RSV-LTR), Moloney murine leukaemia virus (MoMLV) LTR, CHO specific Chinese hamster elongation factor 1-alpha (CHEF1α) promoter, thymidine kinase (TK) promoter, actin promoter, glyceraldehyde 3-phosphate dehydrogenase (GAPDH) promoter, cyclin T1 promoter, RNA polymerase III U3 promoter, cyclophilin promoter, *Autographa californica* nuclear polyhedrosis virus (AcNPV) P10 promoter, β3-galactosyltransferase 5 (β3GAL-T5) promoter, or CAG promoter.

7. The cell of claim 1, wherein the second control element or third control element comprises a Grp78 promoter element.

8. The cell of claim 1, wherein the Cas9 molecule is selected from:

(a) a Cas9 molecule with a modified cleavage activity as compared to a naturally occurring Cas9;

(b) a Cas9 molecule lacking cleavage activity in one or both of the HNH and RuvC domains;

(c) a dCas9 molecule; or (d) a Cas9 molecule that further comprises a heterologous repressor domain that enhances repression of the exogenous therapeutic polypeptide, optionally wherein the heterologous repressor domain is selected from the group consisting of: the KRAB (Krupel-associated box) domain of Kox1, the CS (chromoshadow) domain of HP1α, the WPRW domain of Hes1, and four concatenated copies of the mSin3 interaction domain (SID4X).

9. The cell of claim 1, which is a mammalian cell line.

10. A kit for making a cell for expression of a therapeutic polypeptide, the kit comprising:

a first nucleic acid comprising a first control element operably linked to an insertion site suitable for introducing an exogenous sequence encoding the therapeutic polypeptide such that the exogenous sequence is operably linked to the first control element;

a second nucleic acid comprising a second control element operably linked to a sequence encoding a repressor polypeptide; and a third nucleic acid comprising a third control element operably linked to a sequence encoding one or more gRNAs with homology to the sequence encoding an exogenous therapeutic polypeptide, or with homology to the first control element, wherein (i) the repressor polypeptide is a Cas9 molecule;

(ii) the repressor polypeptide in combination with the one or more gRNAs, inhibits expression of the therapeutic polypeptide; and (iii) the second control element or the third control element is:

(a) an endoplasmic reticulum response element (ERSE);

(b) activated by the unfolded protein response (UPR); or (c) activated by accumulation of misfolded protein;

wherein:

i) the second control element or the third control element have a first level of activity under a first condition and a second level of activity under a second condition; or ii) both the second control element and the third control element have a first level of activity under a first condition and a second level of activity under a second condition, and wherein the first condition and the second condition are (i) a lower level of unfolded or misfolded polypeptide in the endoplasmic reticulum (ER) and a higher level of unfolded or misfolded polypeptide in the ER, respectively; (ii) a lower level of activation of the unfolded protein response (UPR) and a higher level of activation of the UPR, respectively; or (iii) a lower level of protein aggregation and a higher level of protein aggregation, respectively; and wherein in the presence of the second condition, the repressor polypeptide in combination with the one or more gRNAs, is expressed and inhibits expression of the therapeutic polypeptide.

11. A method of making a therapeutic polypeptide, comprising culturing the cell of claim 1 under conditions that allow for making of the therapeutic polypeptide, thereby making the therapeutic polypeptide.

12. The cell of claim 1, wherein the second control element or the third control element comprises:

(a) a promoter that comprises a sequence selected from SEQ ID NOs: 8-14; or (b) a promoter that comprises a sequence with 0, 1, 2, or 3 base substitutions as compared to a sequence selected from SEQ ID NOs: 8-14.

* * * * *

SEQUENCE LISTING

<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1
tgtcaacatg gcggtaatgt tgg                                          23

<210> SEQ ID NO 2
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 2
taccgcccat tgcgtcaat ggg                                            23

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ctaccgccca tttgcgtcaa tgg                                           23

<210> SEQ ID NO 4
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
accgttaaca gcaccgcaac ggg                                           23

<210> SEQ ID NO 5
<211> LENGTH: 2108
<212> TYPE: DNA
<213> ORGANISM: Human betaherpesvirus 5

<400> SEQUENCE: 5
ctgcagtgaa taataaaatg tgtgtttgtc cgaaatacgc gttttgagat ttctgtcgcc    60
gactaaattc atgtcgcgcg atagtggtgt ttatcgccga tagagatggc gatattggaa   120
aaatcgatat ttgaaaatat ggcatattga aaatgtcgcc gatgtgagtt tctgtgtaac   180
tgatatcgcc atttttccaa aagtgatttt tgggcatacg cgatatctgg cgatagcgct   240
tatatcgttt acgggggatg cgatagacg  actttggtga cttgggcgat tctgtgtgtc   300
gcaaatatcg cagtttcgat ataggtgaca gacgatatga ggctatatcg ccgatagagg   360
cgacatcaag ctggcacatg gccaatgcat atcgatctat acattgaatc aatattggcc   420
attagccata ttattcattg gttatatagc ataaatcaat attggctatt ggccattgca   480
tacgttgtat ccatatcata atatgtacat ttatattggc tcatgtccaa cattaccgcc   540
atgttgacat tgattattga ctagttatta atagtaatca attacggggt cattagttca   600
tagcccatat atggagttcc gcgttacata acttacggta aatggcccgc ctggctgacc   660
gcccaacgac ccccgcccat tgacgtcaat aatgacgtat gttcccatag taacgccaat   720
agggactttc cattgacgtc aatgggtgga gtatttacgg taaactgccc acttggcagt   780
acatcaagtg tatcatatgc caagtacgcc ccctattgac gtcaatgacg gtaaatggcc   840
cgcctggcat tatgcccagt acatgacctt atgggacttt cctacttggc agtacatcta   900
cgtattagtc atcgctatta ccatggtgat gcggttttgg cagtacatca atgggcgtgg   960
atagcggttt gactcacggg gatttccaag tctccacccc attgacgtca atgggagttt  1020
gttttggcac caaaatcaac gggactttcc aaaatgtcgt aacaactccg ccccattgac  1080
```

| | |
|---|---|
| gcaaatgggc ggtaggcgtg tacggtggga ggtctatata agcagagctc gtttagtgaa | 1140 |
| ccgtcagatc gcctggagac gccatccacg ctgttttgac ctccatagaa gacaccggga | 1200 |
| ccgatccagc ctccgcggcc gggaacggtg cattggaacg cggattcccc gtgccaagag | 1260 |
| tgacgtaagt accgcctata gagtctatag gcccaccccc ttggcttctt atgcatgcta | 1320 |
| tactgttttt ggcttggggt ctatacaccc ccgcttcctc atgttatagg tgatggtata | 1380 |
| gcttagccta taggtgtggg ttattgacca ttattgacca ctcccctatt ggtgacgata | 1440 |
| cttttccatta ctaatccata acatggctct tgccacaac tctctttatt ggctatatgc | 1500 |
| caatacactg tccttcagag actgacacgg actctgtatt tttacaggat ggggtctcat | 1560 |
| ttattattta caaattcaca tatacaacac caccgtcccc agtgcccgca gtttttatta | 1620 |
| aacataacgt gggatctcca cgcgaatctc gggtacgtgt tccggacatg ggctcttctc | 1680 |
| cggtagcggc ggagcttcta catccgagcc ctgctcccat gcctccagcg actcatggtc | 1740 |
| gctcggcagc tccttgctcc taacagtgga ggccagactt aggcacagca cgatgcccac | 1800 |
| caccaccagt gtgccgcaca aggccgtggc ggtagggtat gtgtctgaaa atgagctcgg | 1860 |
| ggagcgggct tgcaccgctg acgcatttgg aagacttaag gcagcggcag aagaagatgc | 1920 |
| aggcagctga gttgttgtgt tctgataaga gtcagaggta actcccgttg cggtgctgtt | 1980 |
| aacggtggag ggcagtgtag tctgagcagt actcgttgct gccgcgcgcg ccaccagaca | 2040 |
| taatagctga cagactaaca gactgttcct ttccatgggt cttttctgca gtcaccgtcc | 2100 |
| ttgacacg | 2108 |

<210> SEQ ID NO 6
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

| | |
|---|---|
| tgtacaaaaa agcaggcttt aaaggaacca attcagtcga ctggatccgg taccaaggtc | 60 |
| gggcaggaag agggcctatt tcccatgatt ccttcatatt tgcatatacg atacaaggct | 120 |
| gttagagaga taattagaat taatttgact gtaaacacaa agatattagt acaaaatacg | 180 |
| tgacgtagaa agtaataatt tcttgggtag tttgcagttt taaaattatg ttttaaaatg | 240 |
| gactatcata tgcttaccgt aacttgaaag tatttcgatt tcttggcttt atatatcttg | 300 |
| tggaaaggac gaaacacc | 318 |

<210> SEQ ID NO 7
<211> LENGTH: 1494
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

| | |
|---|---|
| tagcataagc tacagatcaa ccaggttatc aattctacct gtaccactca ccagtgacta | 60 |
| ttctatttag ccaccccccc cccaatgatc tcttctggaa aatgggaaac atctaccaag | 120 |
| aattaatcaa aggactaaat gacacatgca aaaaaaaaa aaccttagaa cagtgtttta | 180 |
| agcaggataa gtagttcaag accagtttgg accatgtctc aaaactaaag gaacaacgaa | 240 |

```
gtacatttag tatttttgc aacatgttat tattacatag catcaggaag acaatttttt      300
ctttgtctgc taaatgcctt tgtcatatca gacctatttc aagagtcagg atagaatggt      360
gtcaagaagg gatgaggaag gacttgtaaa ttataaccaa gccacaaatg aaaatgatag      420
acaaggatcg ggaacattat ggggcgacaa gctagaaaa aaaaatgata tattccaggg       480
tggaaagtgc tcgcttgact attcatagaa cagaatagcc acagcatagc gggggggctca    540 gtactaggtt gcaaatggcc aggccaattc tgggacttaa ccccaagaaa agaaaaattg     600
gcaaggccag gatagacaaa tgcagctggc ctaggggtga agggaaaaca gttggctgag     660
aagagccacg attcgcagag aggcagaaca cagactagga cccagctcga gacgtgcagg    720
ccgggtgggt aacatagagc ccgggcgctc ggctacccga gaacgtgagg gaggctggga    780
agggcagaga tgcgttccca ggcgaccaca gcatctatgc tgaggctgag cagctcggga     840
cccgagggga cttaggagga gaaaaggccg catactgctt cggggtaagg gacagaccgg     900
ggaaggaccc aagtcccacc gcccagaggg aactgacacg cagaccccgc agcagtcccc    960
gggggccggg tgacgggagg acctggacgg ttaccggcgg aaacggtctc gggttgagag    1020
gtcacctgag atgctgcctc tcattggcgg ccgttgagag taaccagtag ccaatgagtc    1080
agcccggggg gcgtagcggt gacgtaagtt gcggaggagg ccgcttcgaa tcggcagcgg    1140
ccagcttggt ggcatggacc aatcagcgtc ctccaacgag aagcgccttc accaatcgga    1200
ggcctccacg acgggctgg ggggagggta tataagccaa gtcggcggcg gcgcgctcca     1260
cactggccaa gacaacagtg accggaggac ctgcctttgc ggctccgaga ggtaagcgcc    1320
gcggcctgct cttgccagac ctcctttgag cctgtctcgt ggctcctcct gacccggggg    1380
gcttctgtcg ccctcagatc ggaacgccgc cgcgctccgg gactacagcc tgttgctgga    1440
cttcgagact gcagacggac cgaccgctga gcactggccc acagcgccgg caag          1494
```

<210> SEQ ID NO 8
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other

<400> SEQUENCE: 8 ngaanttcn ngaa                                                        14

<210> SEQ ID NO 9
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

```
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 9
ngaanngaan nttcn                                                      15

<210> SEQ ID NO 10
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 10
ngaanngaan ngaan                                                      15

<210> SEQ ID NO 11
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 11
nttcnngaan ngaan                                                      15
```

```
<210> SEQ ID NO 12
<211> LENGTH: 8
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12 tgacgtca                                                                   8

<210> SEQ ID NO 13
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(7)
<223> OTHER INFORMATION: a, c, t, g, unknown or other

<400> SEQUENCE: 13 tgasnnngc                                                                  9

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(14)
<223> OTHER INFORMATION: a, c, t, g, unknown or other

<400> SEQUENCE: 14
ccaatnnnnn nnnnccacg                                                      19

<210> SEQ ID NO 15
<211> LENGTH: 1368
<212> TYPE: PRT
<213> ORGANISM: Streptococcus pyogenes

<400> SEQUENCE: 15
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

```
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525
```

```
Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
```

-continued

```
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
```

Gly Leu Tyr Glu Thr Arg Ile Asp Leu Ser Gln Leu Gly Gly Asp
                1355                1360                1365

<210> SEQ ID NO 16
<211> LENGTH: 1368
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

```
Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
```

```
                   755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                    805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
            835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                    885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
```

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 17
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gaagttacta ttccgaagtt cctattctct agaaagtata ggaacttc            48

<210> SEQ ID NO 18
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
gaagttacta ttccgaagtt cctattctct agatagtata ggaacttc            48

<210> SEQ ID NO 19
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19

```
gaagttacta ttccgaagtt cctattctct acttagtata ggaacttc                48

<210> SEQ ID NO 20
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'WPRW' domain sequence"

<400> SEQUENCE: 20

Trp Pro Arg Trp
1
```